US010396297B2

(12) United States Patent
Voges et al.

(10) Patent No.: US 10,396,297 B2
(45) Date of Patent: Aug. 27, 2019

(54) MATERIALS FOR ELECTRONIC DEVICES

(71) Applicant: Merck Patent Gmbh, Darmstadt (DE)

(72) Inventors: Frank Voges, Bad Duerkheim (DE);
Frank Stieber, Einhausen (DE);
Philipp Stoessel, Frankfurt Am Main (DE); Teresa Mujica-Fernaud, Darmstadt (DE); Christof Pflumm, Darmstadt (DE); Joachim Kaiser, Darmstadt (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 15/521,026

(22) PCT Filed: Sep. 25, 2015

(86) PCT No.: PCT/EP2015/001910
§ 371 (c)(1),
(2) Date: Apr. 21, 2017

(87) PCT Pub. No.: WO2016/062368
PCT Pub. Date: Apr. 28, 2016

(65) Prior Publication Data
US 2017/0331053 A1 Nov. 16, 2017

(30) Foreign Application Priority Data

Oct. 24, 2014 (EP) .................................... 14003629

(51) Int. Cl.
*H01L 51/54* (2006.01)
*H01L 51/00* (2006.01)
*H01L 51/50* (2006.01)
*C07F 9/94* (2006.01)
*H01L 51/56* (2006.01)

(52) U.S. Cl.
CPC ............ *H01L 51/0077* (2013.01); *C07F 9/94* (2013.01); *H01L 51/005* (2013.01); *H01L 51/006* (2013.01); *H01L 51/0059* (2013.01); *H01L 51/0061* (2013.01); *H01L 51/506* (2013.01); *H01L 51/5012* (2013.01); *H01L 51/5036* (2013.01); *H01L 51/56* (2013.01); *H01L 51/5056* (2013.01); *Y02E 10/549* (2013.01); *Y02P 70/521* (2015.11)

(58) Field of Classification Search
CPC ....... C09K 11/06; C07F 9/94; H01L 51/0032; H01L 51/005; H01L 51/006; H01L 51/0061; H01L 51/0077; H01L 51/50; H01L 51/5012; H01L 51/5016; H01L 51/5036; H01L 51/5056; H01L 51/56
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| 9,312,495 B2 | 4/2016 | Pflumm et al. |
| 9,768,391 B2 | 9/2017 | Mujica-Fernaud et al. |
| 2006/0003487 A1 | 1/2006 | Chung |
| 2007/0222376 A1 | 9/2007 | Ohsawa et al. |
| 2011/0266533 A1* | 11/2011 | Buesing ............... C07D 219/02 257/40 |
| 2013/0001472 A1 | 1/2013 | Ohshita et al. |
| 2013/0334517 A1* | 12/2013 | Hong ..................... C09K 11/06 257/40 |
| 2014/0027747 A1* | 1/2014 | Mun ...................... H01L 51/006 257/40 |
| 2014/0217392 A1* | 8/2014 | Hong ................... H01L 51/0052 257/40 |
| 2014/0264313 A1 | 9/2014 | Schmid et al. |
| 2014/0316134 A1* | 10/2014 | Stoessel ............... C07D 221/20 544/180 |
| 2015/0045529 A1* | 2/2015 | Stoessel ............... C07D 493/10 528/220 |
| 2015/0123047 A1* | 5/2015 | Maltenberger ...... H01L 51/0077 252/519.21 |
| 2016/0181540 A1 | 6/2016 | Kessler et al. |
| 2017/0098787 A1 | 4/2017 | Maltenberger et al. |

FOREIGN PATENT DOCUMENTS

| KR | 20070034016 A | 3/2007 | |
| KR | 20120009984 A * | 2/2012 | |
| WO | WO-2012034627 A1 | 3/2012 | |
| WO | WO-2012099376 A2 * | 7/2012 | ............. C09K 11/06 |
| WO | WO-2012134203 A2 * | 10/2012 | ........... H01L 51/006 |
| WO | WO-2013083216 A1 * | 6/2013 | ........... C07D 221/20 |
| WO | WO-2013129836 A1 * | 9/2013 | ......... H01L 51/0052 |
| WO | WO-2013139431 A1 * | 9/2013 | ........... C07D 493/10 |
| WO | WO-2013182389 A2 | 12/2013 | |
| WO | WO-2014015938 A1 | 1/2014 | |
| WO | WO-2015018539 A1 | 2/2015 | |

OTHER PUBLICATIONS

Machine translation of KR2012-0009984 (Year: 2012).*
Dikarev, E., et al., "Tuning the Properties at Heterobimetallic Core: Mixed-Ligand Bismuth-Rhodium Paddlewheel Carboxylates", Journal of the American Chemical Society, vol. 128, No. 9, (2006), pp. 2814-2815.
International Search Report for PCT/EP2015/001910 dated Jan. 18, 2016.
International Search Report for PCT/EP2015/001940 dated Jan. 12, 2016.
Schmid, G., et al., "Fluorinated Copper(I) Carboxylates as Advanced Tunable p-Dopants for Organic Light-Emitting Diodes", Advanced Materials, vol. 26, No. 6, (2014), pp. 878-885.

(Continued)

*Primary Examiner* — Andrew K Bohaty
(74) *Attorney, Agent, or Firm* — Drinker Biddle & Reath LLP

(57) ABSTRACT

The present application relates to a material comprising a monoarylamine of a defined formula and a p-dopant of a defined formula. The present application further relates to the use of said material in an organic layer of an electronic device, the device preferably being an organic electroluminescent device (OLED).

28 Claims, No Drawings

(56) References Cited

OTHER PUBLICATIONS

Written Opinion of the International Searching Authority for PCT/EP2015/001910 dated Jan. 18, 2016.
Written Opinion of the International Searching Authority for PCT/EP2015/001940 dated Jan. 12, 2016.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2015/001910, filed Sep. 25, 2015, which claims benefit of European Application Nos. 14003629.4, filed Oct. 24, 2014, and 15180258.4, filed Aug. 7, 2015, all of which are incorporated herein by reference in their entirety.

The present application relates to a material comprising a monoarylamine of a defined formula and a metal complex of a defined formula. The present application further relates to the use of said material in an organic layer of an electronic device, the device preferably being an organic electroluminescent device (OLED).

The term "comprising" is understood in the context of this application to mean that further constituents or steps may be present. The indefinite article "a" does not exclude the plural.

Electronic devices in the context of this application are understood to mean what are called organic electronic devices, which contain organic semiconductor materials as functional materials.

The structure of OLEDs in which organic compounds are used as functional materials is described, for example, in U.S. Pat. Nos. 4,539,507, 5,151,629, EP 0676461 and WO 98/27136. In general, the term OLEDs is understood to mean electronic devices which have one or more layers comprising organic compounds and emit light on application of electrical voltage.

A great influence on the performance data of electronic devices is possessed by layers having a hole-transporting function (hole-transporting layers), for example hole injection layers, hole transport layers and electron blocker layers.

The prior art discloses use of monoarylamines as materials for hole-transporting layers. Such monoarylamines are described, for example, in JP 1995/053955, WO 2006/123667, JP 2010/222268, WO 2012/034627, WO 2013/120577, WO 2014/015938 and WO 2014/015935.

In addition, the prior art discloses use of p-dopants in combination with hole transport materials in hole-transporting layers of OLEDs. A p-dopant is understood here to mean a compound which, when added as a minor component to a main component, significantly increases the conductivity thereof for holes.

p-Dopants known in the prior art are organic electron acceptor compounds, for example 7,7,8,8-tetracyano-2,3,5, 6-tetrafluoroquinodimethane (F4TCNQ). The prior art further discloses, as p-dopants, metal complexes of transition metal cations and main group metal cations, for example in WO 2011/33023 and WO 2013/182389.

The hole transport materials known in the prior art and the p-dopants known in the prior art result in a great variety of potentially possible combinations. Of these, only some are disclosed in the prior art. Mention may be made here by way of example of the combination of main group metal complexes as p-dopants with tetraamines, for example 2,2',7,7'-tetra(N, N-di-p-tolyl)amino-9,9-spirobifluorene in the hole transport layer of an OLED. This is disclosed in WO 2013/182389. A further example from the prior art is the combination of F4TCNQ with monoarylamines, for example tris-para-biphenylamine in the hole transport layer of an OLED. This is disclosed in WO 2013/135352.

However, OLEDs comprising these materials in the hole transport layer are in need of improvement in relation to lifetime and efficiency.

There is additionally a need for p-dopants capable of efficiently doping hole transport materials having a low-lying HOMO, especially those having a HOMO within the range from −5.2 to −5.7 eV, such that it is possible to obtain dopant-hole transport material combinations having both a suitable conductivity and a low HOMO energy level. Suitable and preferred conductivities here are in the range from $10^{-4}$ S/m to $10^{-3}$ S/m. The use of hole transport materials having a low-lying HOMO is highly desirable because this dispenses with the necessity of inserting a further layer having a low HOMO between hole transport layer and emitting layer. This enables a simpler construction of the OLED and hence a more efficient production process. If a further layer is inserted between hole transport layer and emitting layer, it is possible in the desired case of a hole transport layer having a low HOMO to avoid a hole barrier and hence a voltage drop between the hole transport layer and the emitting layer by virtue of the HOMO of the hole transport layer being no higher than the HOMO of the layer between the hole transport layer and emitting layer. This is possible, for example, through the use of the same material in the hole transport layer and the further layer between the hole transport layer and emitting layer.

There is additionally a need for hole transport material-dopant combinations having only low absorption in the visible region (VIS region). The p-dopants known in the prior art, for example NDP-2 or molybdenum oxide dopants, in combination with the standard hole transport materials have absorptions in the VIS region. Low absorption bands in the VIS region are highly desirable since absorptions in the VIS region affect the emission characteristics of the OLEDs and worsen the efficiency thereof.

In studies of possible combinations of p-dopants and hole transport materials for use in hole transport layers, it has now been found that, unexpectedly, a material comprising a monoarylamine of a specific formula (A) and a bismuth complex gives excellent values compared to the prior art in relation to lifetime and efficiency. In addition, the inventive material has lower leakage currents when used in OLEDs than materials according to the prior art. Without being bound to this theory, this may be caused by a lower lateral conductivity of the doped layer of the OLED. With pixels in displays becoming ever smaller, leakage currents are a great problem since they can lead to crosstalk between the pixels. The avoidance thereof is therefore desirable. Yet another feature of the inventive material is no absorption band in the VIS region. Yet another feature is that it is possible with the inventive material, because of the low HOMO position of the monoarylamine, to produce OLEDs which need not have any additional layer between the hole transport layer comprising the inventive material and the emitting layer and can therefore be produced in a more efficient manner.

The present application therefore provides a material comprising a compound P which is a complex of bismuth and a compound A of a formula (A)

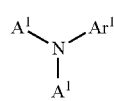

Formula (A)

where the variables that occur are:

$A^1$ is the same or different at each instance and is H, an alkyl group which has 1 to 20 carbon atoms and may be substituted by one or more $R^1$ radicals, or $Ar^1$;

$Ar^1$ is the same or different at each instance and is an aromatic ring system which has 6 to 60 aromatic ring atoms and may be substituted by one or more $R^1$ radicals, or a heteroaromatic ring system which has 5 to 60 aromatic ring atoms and may be substituted by one or more $R^1$ radicals; $Ar^1$ and/or $A^1$ groups here may be bonded to one another via $R^1$ radicals;

$R^1$ is the same or different at each instance and is selected from H, D, F, C(=O)$R^2$, CN, Si($R^2$)$_3$, P(=O)($R^2$)$_2$, O$R^2$, S(=O)$R^2$, S(=O)$_2R^2$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned may each be substituted by one or more $R^2$ radicals; and where one or more CH$_2$ groups in the alkyl, alkoxy, alkenyl and alkynyl groups mentioned may be replaced by —$R^2$C=C$R^2$—, —C≡C—, Si($R^2$)$_2$, C=O, C=N$R^2$, —C(=O)O—, —C(=O)N$R^2$—, P(=O)($R^2$), —O—, —S—, SO or SO$_2$;

$R^2$ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where two or more $R^2$ radicals may be joined to one another and may form a ring; and where the alkyl groups, aromatic ring systems and heteroaromatic ring systems mentioned may be substituted by F or CN;

where the scope of the formula (A) excludes compounds of the following formula (B)

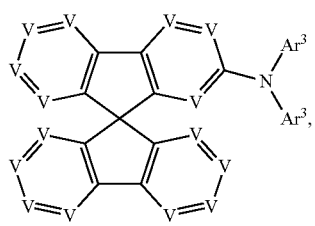

Formula (B)

in which the new variables that occur are:

V is $CR^1$;

$Ar^3$ is the same or different at each instance and is an aromatic ring system which has 6 to 30 aromatic ring atoms and may be substituted by one or more $R^1$ radicals, or a heteroaromatic ring system which has 5 to 30 aromatic ring atoms and may be substituted by one or more $R^1$ radicals; $Ar^1$ groups here may be bonded to one another via $R^1$ radicals.

An aromatic ring system in the context of this invention contains 6 to 60 carbon atoms in the ring system. It does not comprise any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the nonaromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also to be regarded as aromatic ring systems in the context of this invention, for example systems such as biphenyl and terphenyl.

A heteroaromatic ring system in the context of this invention contains 5 to 60 aromatic ring atoms, at least one of which is a heteroatom. The heteroatoms of the heteroaromatic ring system are preferably selected from N, O and/or S. A heteroaromatic ring system corresponds to the abovementioned definition of an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is understood to mean either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood to mean that the cycles share at least one edge with one another.

An aromatic ring system having 6 to 40 aromatic ring atoms or a heteroaromatic ring system having 5 to 40 aromatic ring atoms are especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In the context of the present invention, a straight-chain alkyl group having 1 to 20 carbon atoms and a branched or cyclic alkyl group having 3 to 20 carbon atoms and an alkenyl or alkynyl group having 2 to 20 carbon atoms in which individual hydrogen atoms or $CH_2$ groups may also be replaced by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

The compound A is preferably a monoarylamine. A monoarylamine is understood here to mean a compound having a single arylamino group and not more than one. Preferably, the compound is a monotriarylamino compound, meaning that it has a single triarylamino group. The term "triarylamino group" is preferably also understood to mean compounds containing heteroaryl groups bonded to the amino nitrogen. Further preferably, the compound A has a single amino group. It should be noted that, according to the definition of the present application, carbazole groups do not count as arylamino groups or amino groups.

According to a further preferred embodiment of the invention, the compound A does not contain a fused aryl group having more than 10 aromatic ring atoms nor a fused heteroaryl group having more than 14 aromatic ring atoms.

Preferably, $A^1$ is the same or different at each instance and is an alkyl group which has 1 to 20 carbon atoms and may be substituted by one or more $R^1$ radicals, or $Ar^1$. Preferably, at least one $A^1$ group in the compound A is $Ar^1$; more preferably, both $A^1$ groups in the compound A are $Ar^1$.

$Ar^1$ is preferably the same or different at each instance and is an aromatic ring system which has 6 to 40 aromatic ring atoms and may be substituted by one or more $R^1$ radicals, or a heteroaromatic ring system which has 5 to 40 aromatic ring atoms and may be substituted by one or more $R^1$ radicals.

Preferably, at least one $Ar^1$ group in the compound of the formula (A) is a group which is optionally substituted by one or more $R^1$ radicals and is selected from phenyl, biphenyl, terphenyl, quaterphenyl, naphthyl, phenanthryl, fluoranthenyl, fluorenyl, indenofluorenyl, spirobifluorenyl, furanyl, benzofuranyl, isobenzofuranyl, dibenzofuranyl, thiophenyl, benzothiophenyl, isobenzothiophenyl, dibenzothiophenyl, indolyl, isoindolyl, carbazolyl, indolocarbazolyl, indenocarbazolyl, pyridyl, quinolinyl, isoquinolinyl, acridyl, phenanthridyl, benzimidazolyl, pyrimidyl, pyrazinyl and triazinyl; particular preference among these is given to phenyl, biphenyl, terphenyl, quaterphenyl, naphthyl, phenanthryl, fluoranthenyl, fluorenyl, indenofluorenyl, spirobifluorenyl, dibenzofuranyl, dibenzothiophenyl, carbazolyl, acridyl and phenanthridyl.

$R^1$ is preferably the same or different at each instance and is selected from H, D, F, CN, $Si(R^2)_3$, straight-chain alkyl or alkoxy groups having 1 to 10 carbon atoms, branched or cyclic alkyl or alkoxy groups having 3 to 10 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned may each be substituted by one or more $R^2$ radicals; and where one or more $CH_2$ groups in the alkyl or alkoxy groups mentioned may be replaced by —C≡C—, —$R^2$C═C$R^2$—, Si$(R^2)_2$, C═O, C═N$R^2$, —O—, —S—, —C(═O)O— or —C(═O)N$R^2$—.

Preferably, at least one $Ar^1$ group, more preferably all the $Ar^1$ groups, in the compound of the formula (A) are the same or different at each instance and are selected from the following groups, each of which may be substituted by one or more $R^1$ radicals at any of the unsubstituted positions shown:

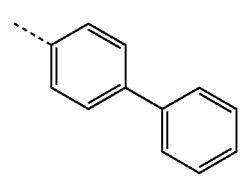

(Ar¹-1)

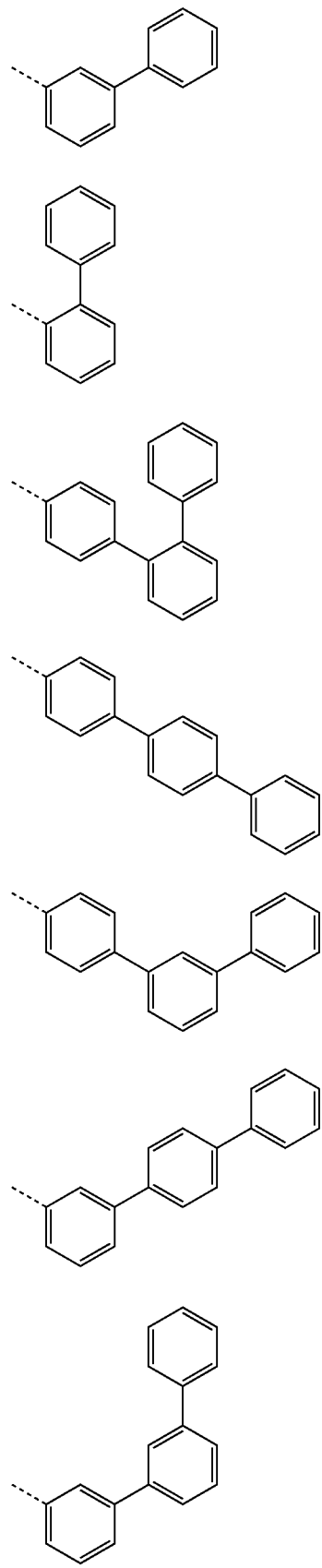
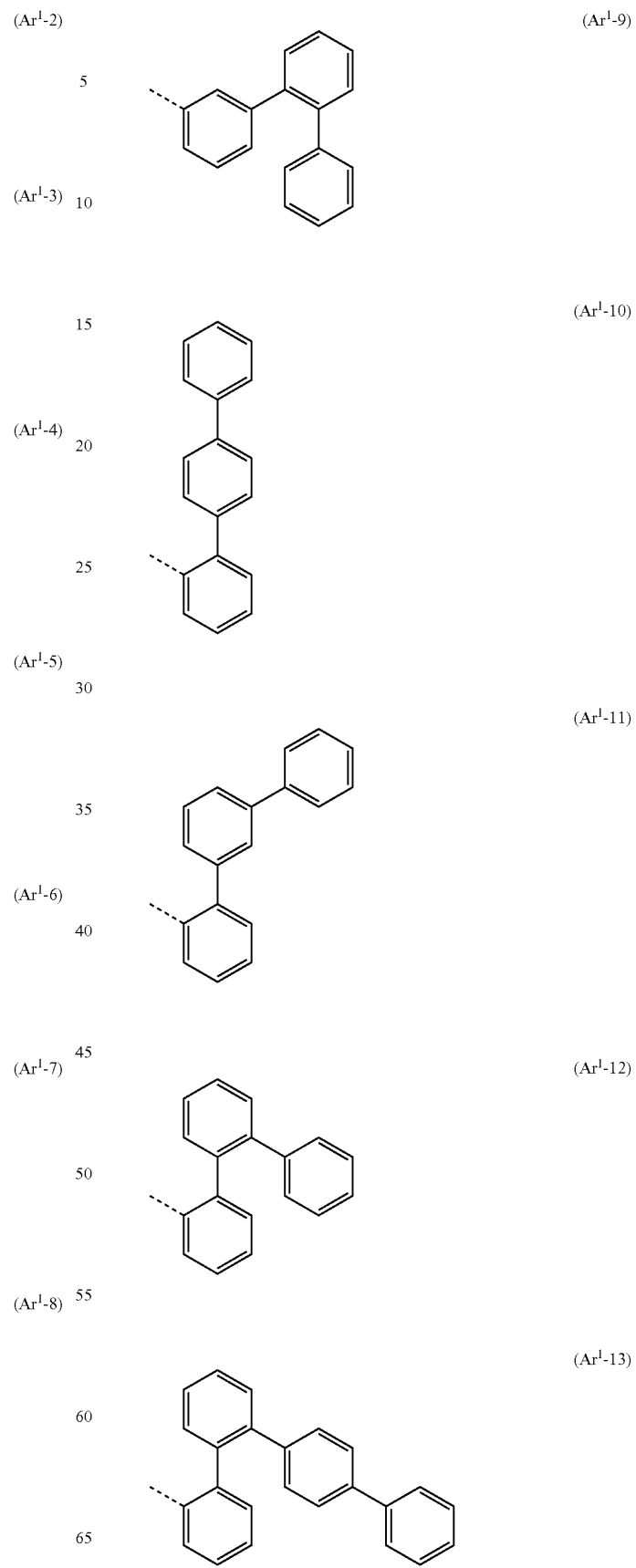

-continued
(Ar¹-14)
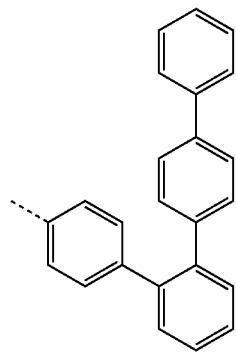
(Ar¹-15)
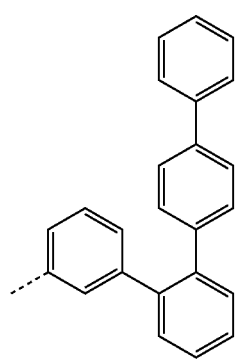
(Ar¹-16)
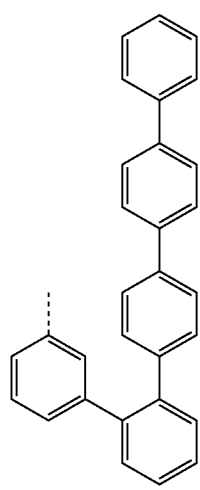
(Ar¹-17)
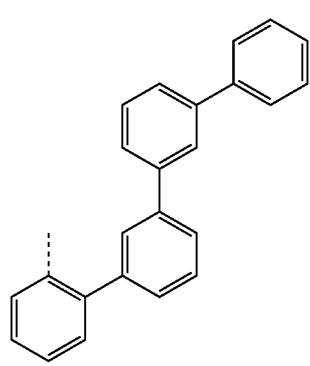
(Ar¹-18)
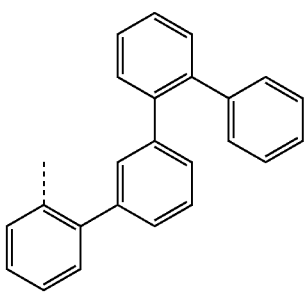
(Ar¹-19)
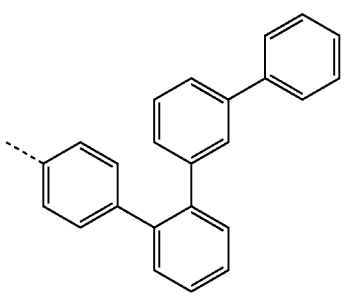
(Ar¹-20)
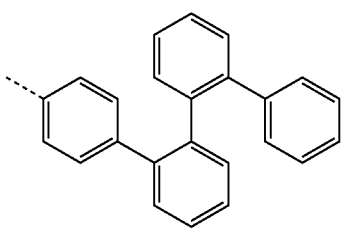
(Ar¹-21)
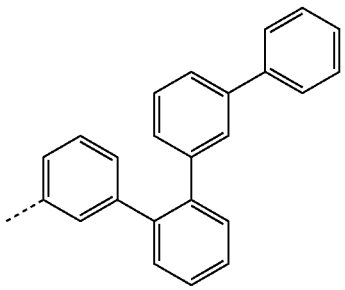
(Ar¹-22)

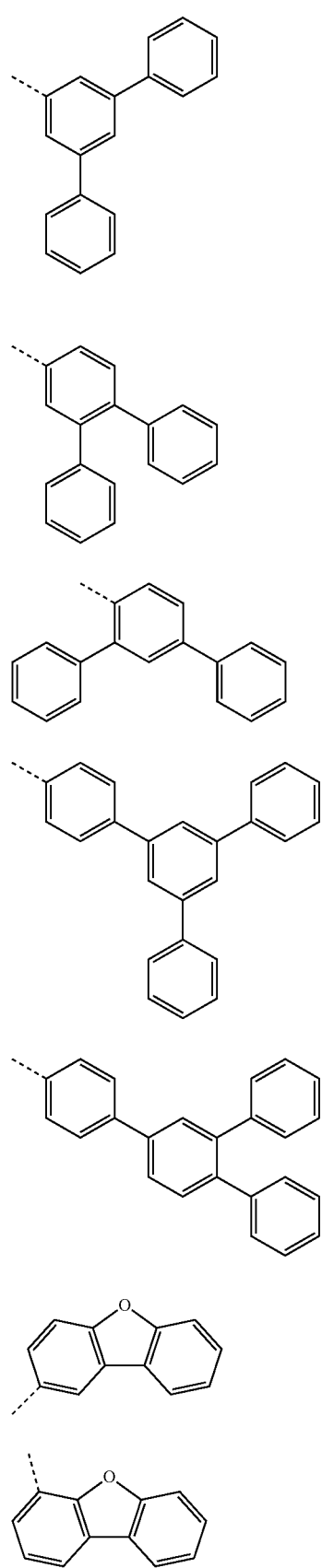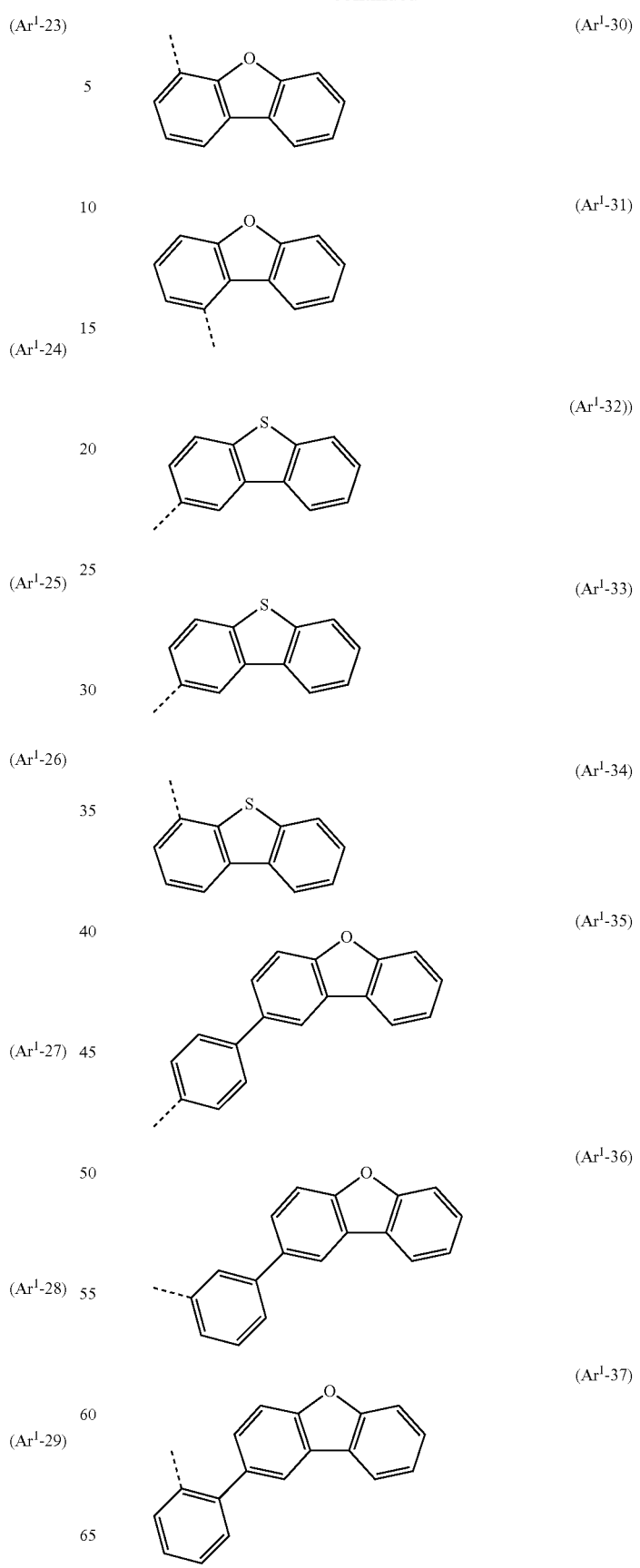

(Ar¹-38) 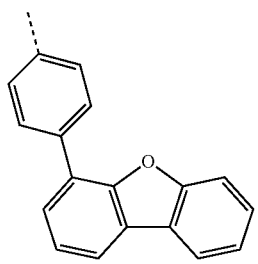
(Ar¹-39) 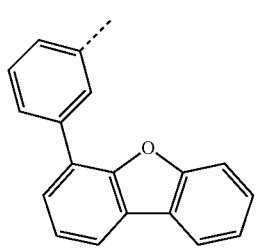
(Ar¹-40) 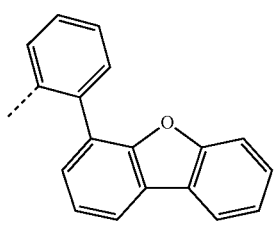
(Ar¹-41) 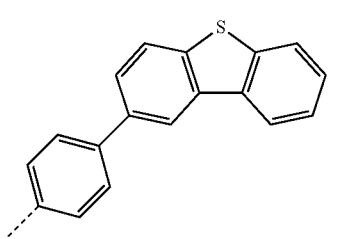
(Ar¹-42) 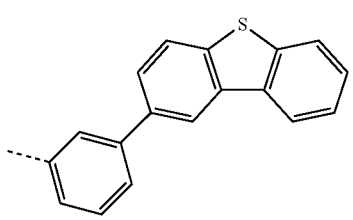
(Ar¹-43) 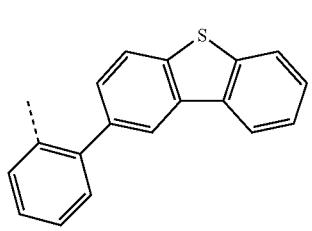
(Ar¹-44) 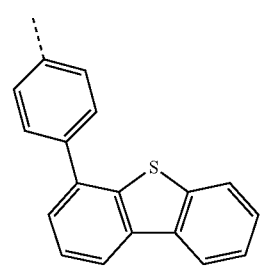
(Ar¹-45) 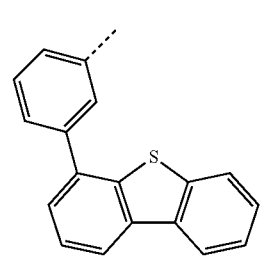
(Ar¹-46) 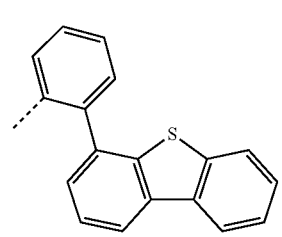
(Ar¹-47) 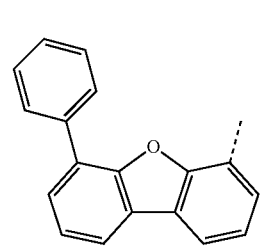
(Ar¹-48) 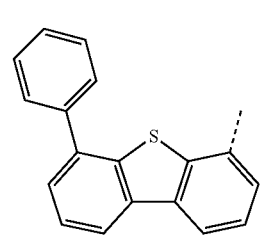
(Ar¹-49) 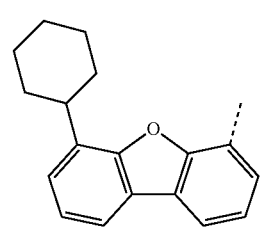

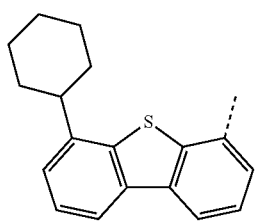 (Ar¹-50)
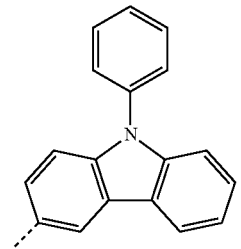 (Ar¹-51)
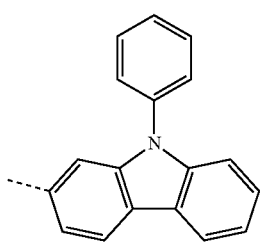 (Ar¹-52)
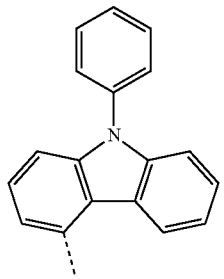 (Ar¹-53)
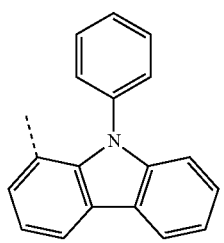 (Ar¹-54)
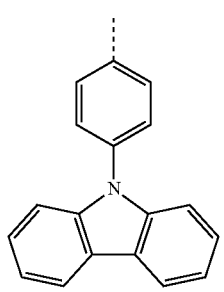 (Ar¹-55)
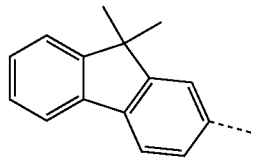 (Ar¹-56)
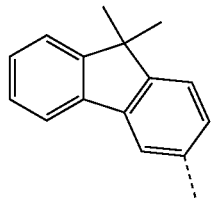 (Ar¹-57)
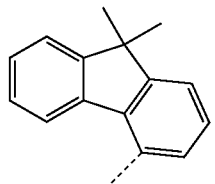 (Ar¹-58)
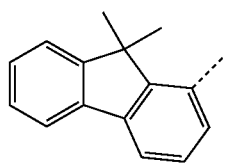 (Ar¹-59)
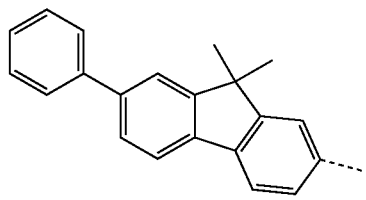 (Ar¹-60)
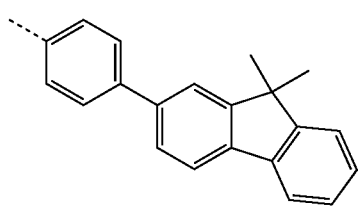 (Ar¹-61)
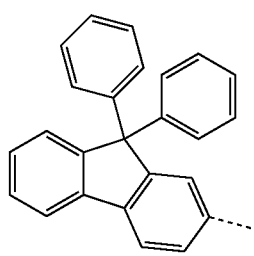 (Ar¹-62)

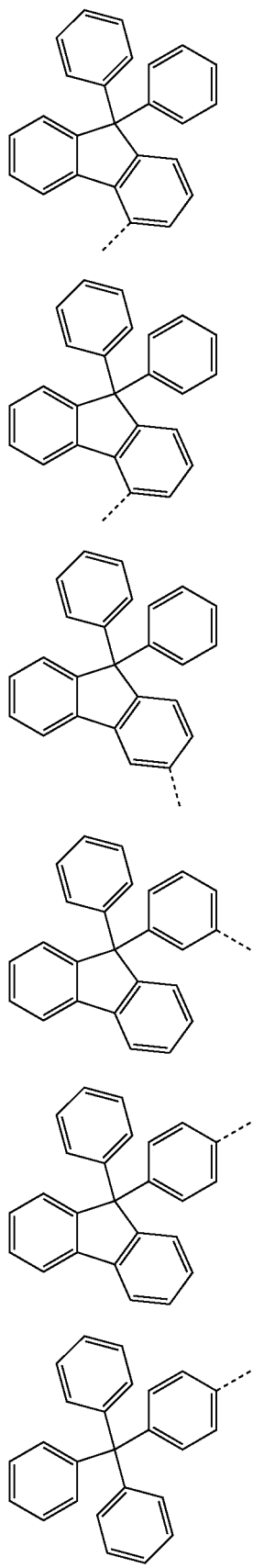
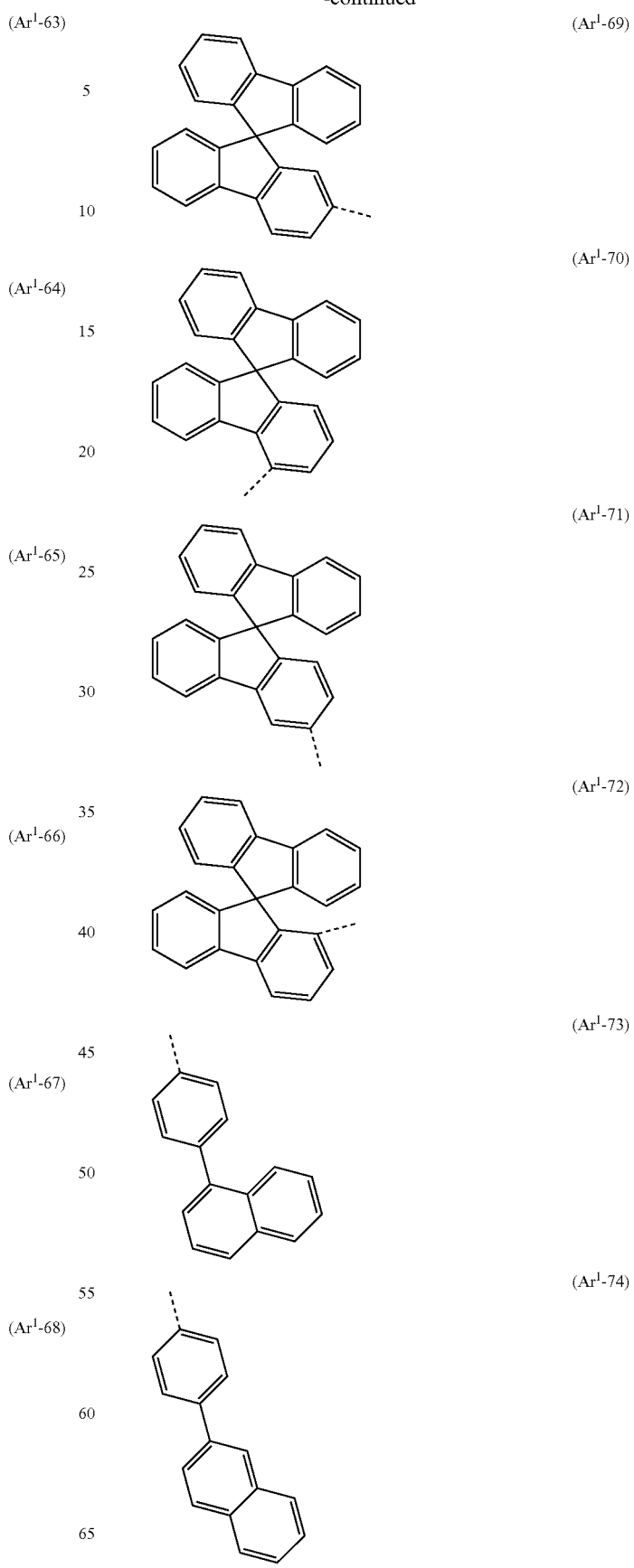

(Ar¹-75) 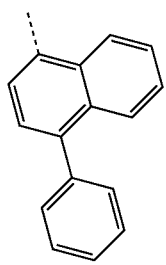
(Ar¹-76) 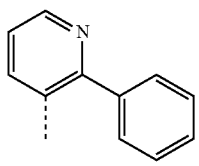
(Ar¹-77) 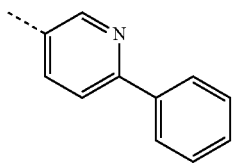
(Ar¹-78) 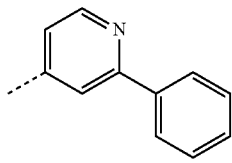
(Ar¹-79) 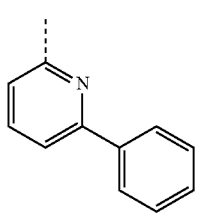
(Ar¹-80) 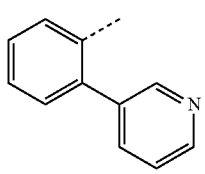
(Ar¹-81) 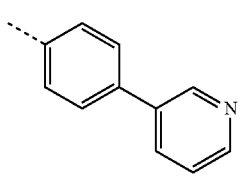
(Ar¹-82) 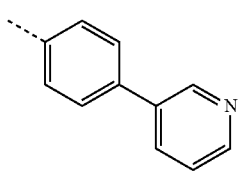
(Ar¹-83) 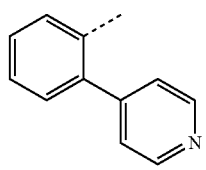
(Ar¹-84) 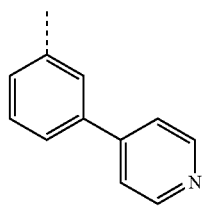
(Ar¹-85) 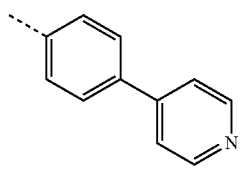
(Ar¹-86) 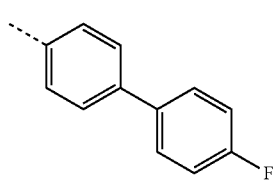
(Ar¹-87) 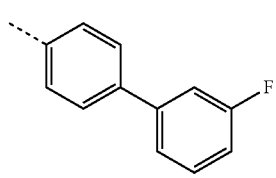
(Ar¹-88) 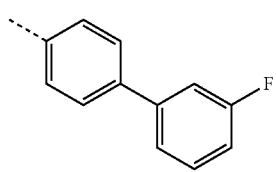
Preferably, compound A corresponds to one of the following formulae, excluding compounds of the formula (B) as defined above:
Formula (A-I)

-continued

Formula (A-II)
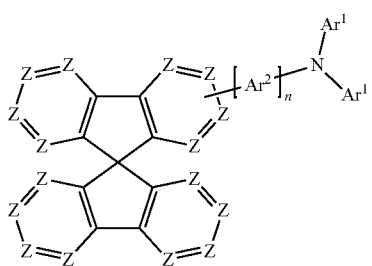

Formula (A-III)
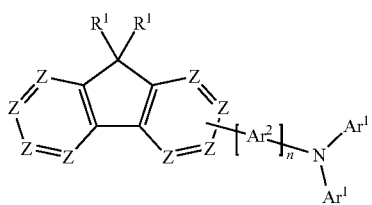

(Formula (A-IV)
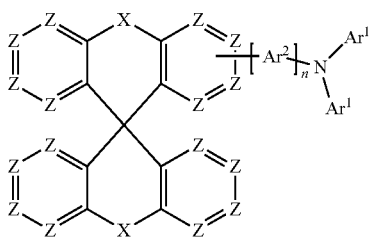

Formula (A-V)
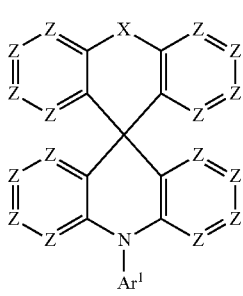

Formula (A-VI)
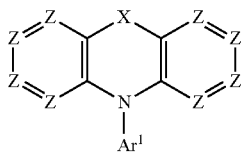

Formula (A-VII)
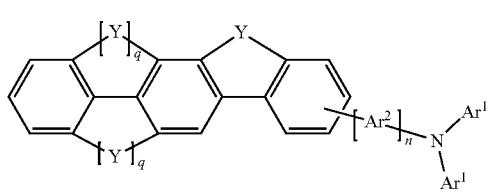

Formula (A-VIII)
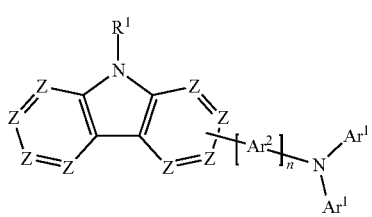

-continued

Formula (A-IX)
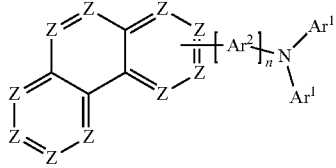

where one or more $R^1$ radicals may be bonded to any of the unsubstituted positions shown, and the variables that occur are as follows:

Z is the same or different at each instance and is $CR^1$ or N;

X is the same or different at each instance and is a single bond, O, S, $C(R^1)_2$, $Si(R^1)_2$, $PR^1$, $C(R^1)_2$—$C(R^1)_2$, or $CR^1$=$CR^1$;

Y is the same or different at each instance and is O, S, $C(R^1)_2$, $Si(R^1)_2$, $PR^1$, $NR^1$, $C(R^1)_2$—$C(R^1)_2$, or $CR^1$=$CR^1$;

$Ar^1$ is as defined above;

$Ar^2$ is an aromatic ring system which has 6 to 20 aromatic ring atoms and may be substituted by one or more $R^1$ radicals, or a heteroaromatic ring system which has 5 to 20 aromatic ring atoms and may be substituted by one or more $R^1$ radicals;

n, p, q are the same or different and are each 0 or 1.

It is preferable that not more than three Z groups in one ring are N. Preferably not more than 2 adjacent Z groups are N. More preferably, Z is $CR^1$.

It is preferable that X is the same or different at each instance and is a single bond, O, S or $(CR^1)_2$.

Preferably, at least one of the indices p and q is 1. Preferably, the sum total of the indices p and q is 1.

Preferably, $Ar^1$ in the abovementioned formulae is (A-I) to (A-IX) selected from the abovementioned preferred embodiments of $Ar^1$.

Preferably, $Ar^2$ comprises at least one group selected from benzene, naphthalene, phenanthrene, fluoranthene, biphenyl, terphenyl, quaterphenyl, fluorene, indenofluorene, spirobifluorene, furan, benzofuran, isobenzofuran, dibenzofuran, thiophene, benzothiophene, isobenzothiophene, dibenzothiophene, indole, isoindole, carbazole, indolocarbazole, indenocarbazole, pyridine, quinoline, isoquinoline, acridine, phenanthridine, benzimidazole, pyrimidine, pyrazine and triazine, where the groups mentioned may be substituted by one or more $R^1$ radicals. Preferably, $Ar^2$ consists exclusively of one of the abovementioned groups or of a combination of a plurality of the abovementioned groups.

Preferably, $Ar^2$ is the same or different at each instance and is selected from the following groups, each of which may be substituted by one or more $R^1$ radicals at any of the unsubstituted positions shown:

(Ar²-1)
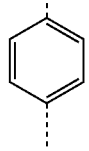

-continued
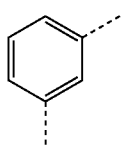 (Ar²-2)
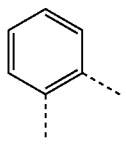 (Ar²-3)
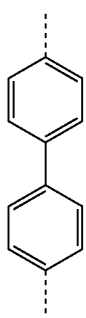 (Ar²-4)
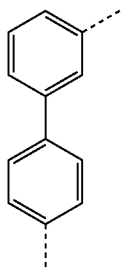 (Ar²-5)
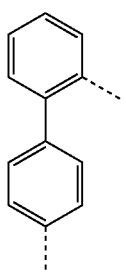 (Ar²-6)
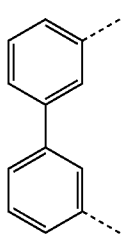 (Ar²-7)
-continued
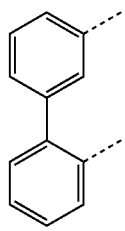 (Ar²-8)
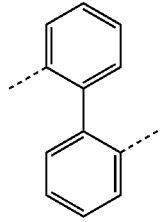 (Ar²-9)
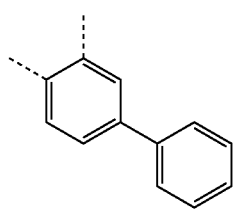 (Ar²-10)
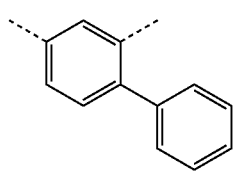 (Ar²-11)
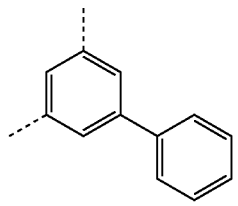 (Ar²-12)
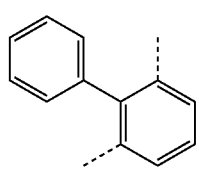 (Ar²-13)
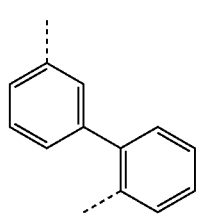 (Ar²-14)

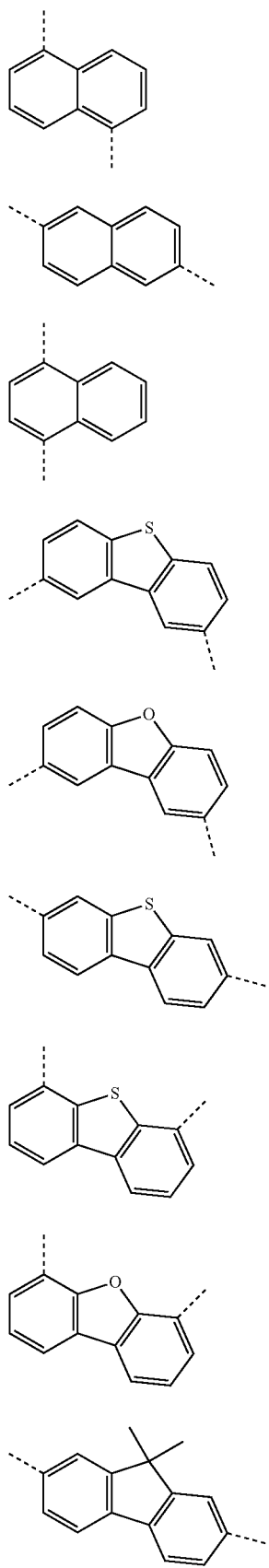
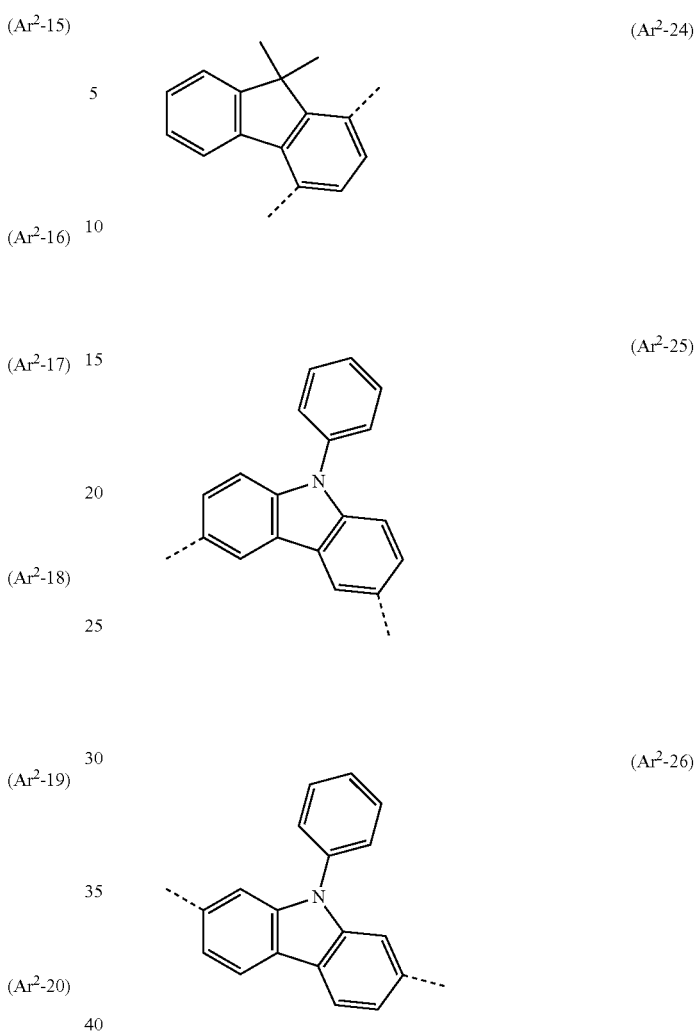
Preferred embodiments of compounds of the formula (A) are the following compounds:
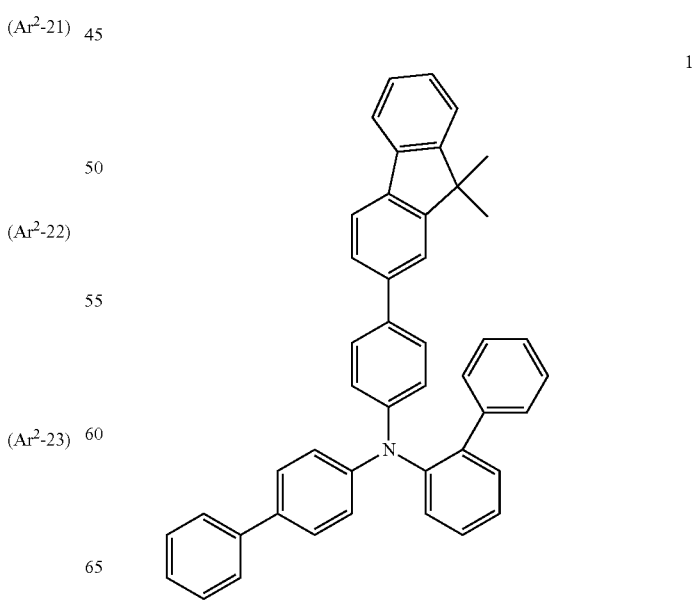

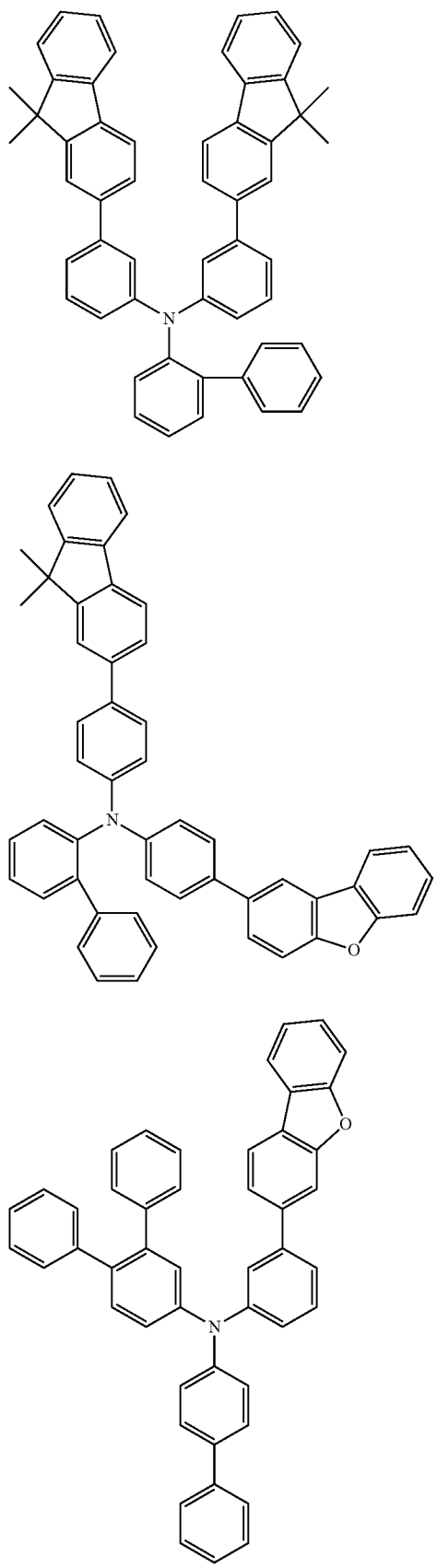
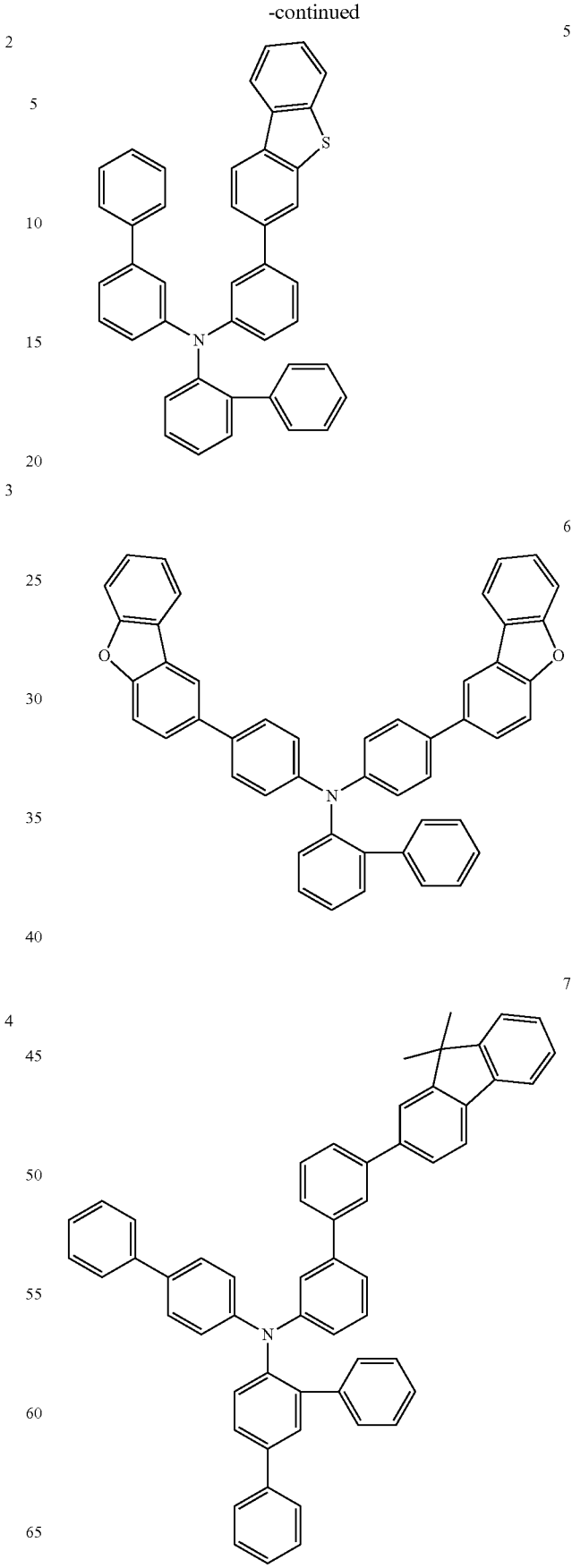

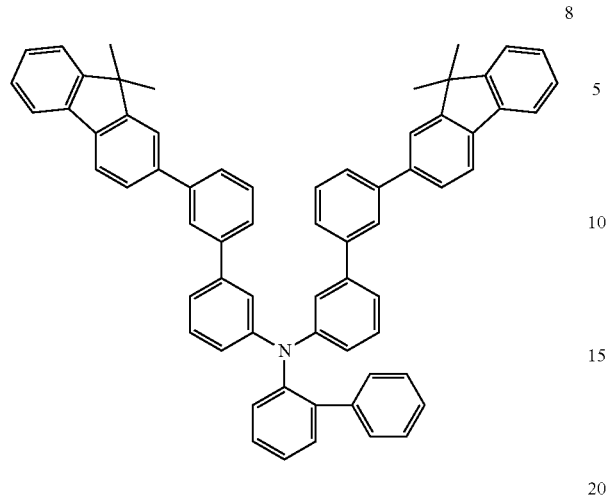
8
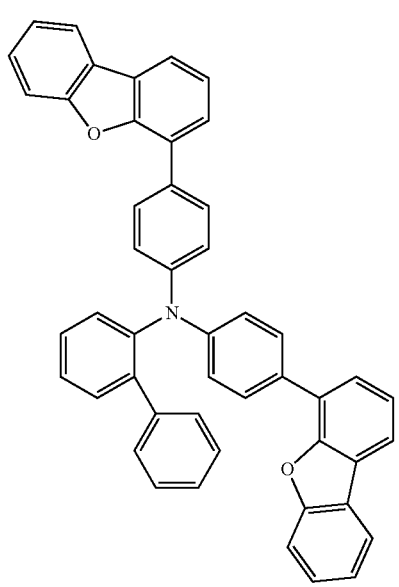
11
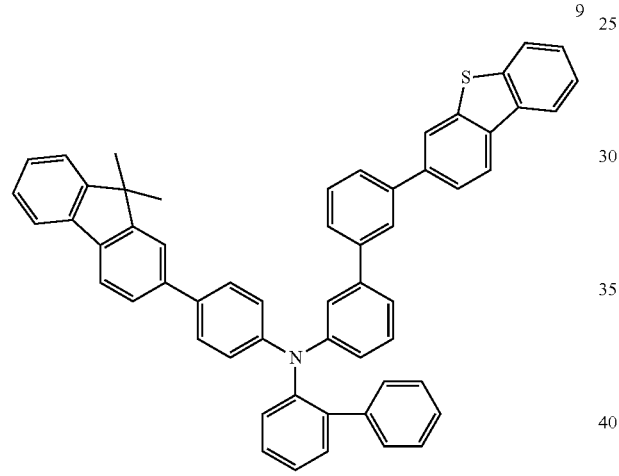
9
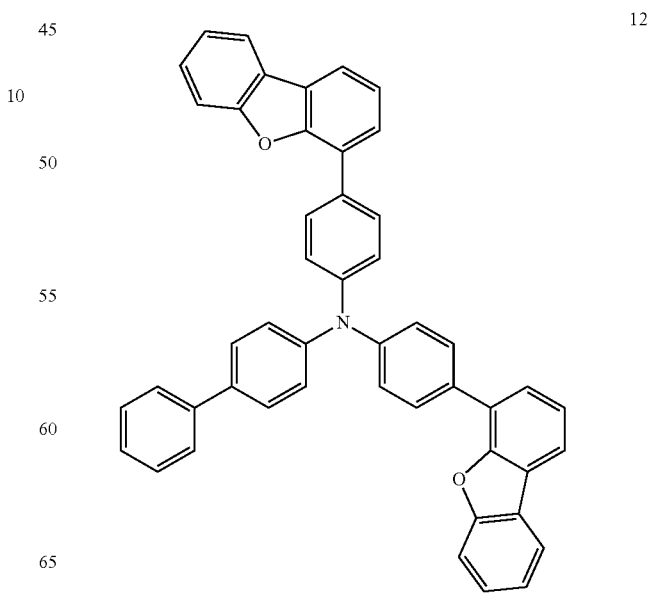
12
10

31
-continued
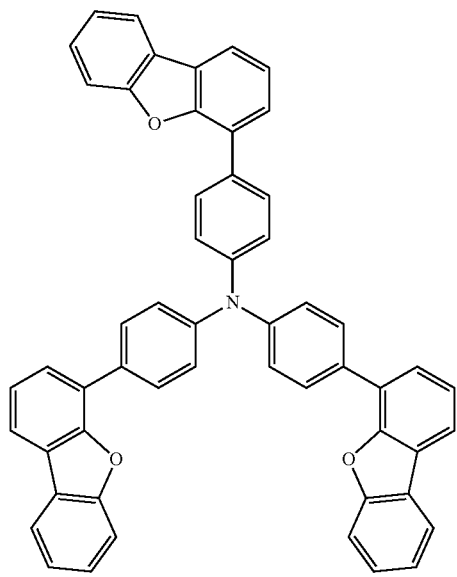
32
-continued
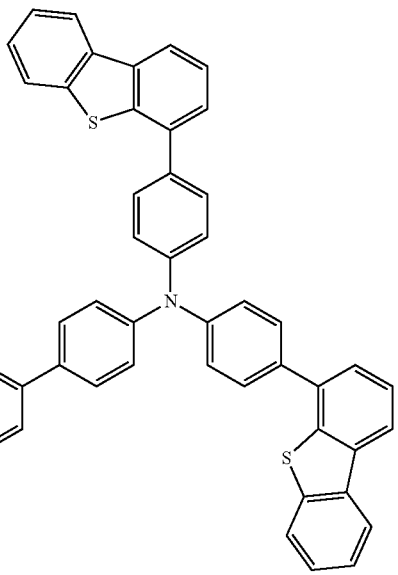
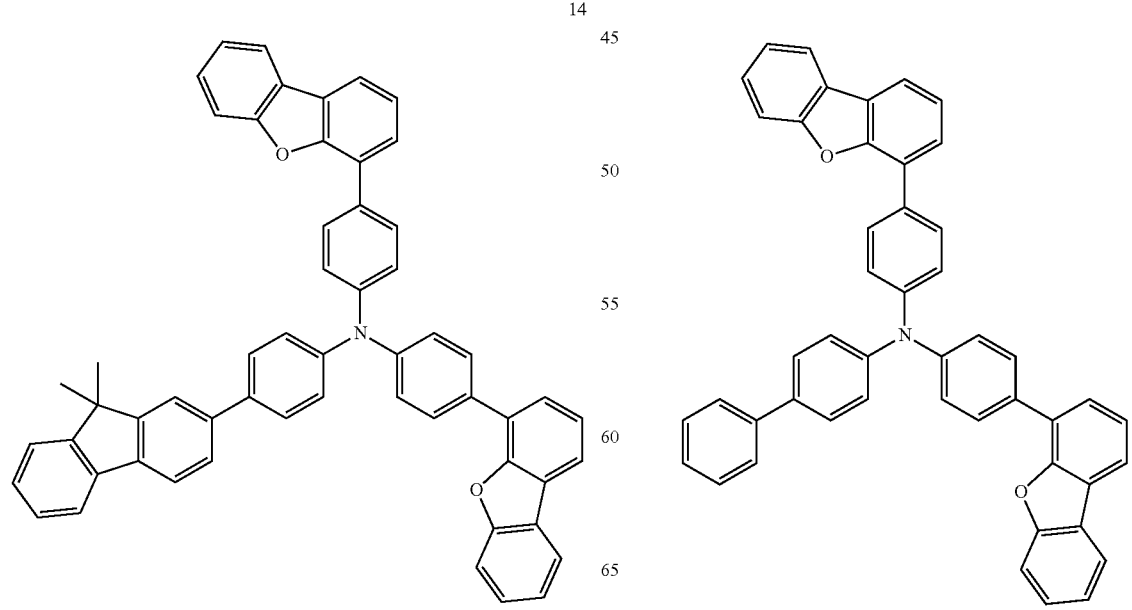

17
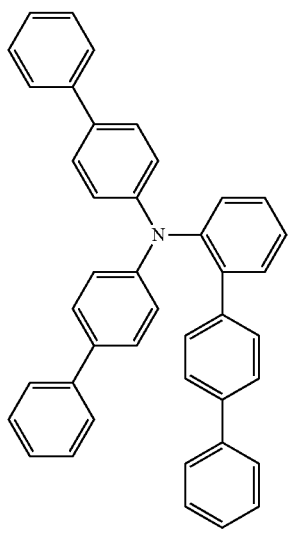
18
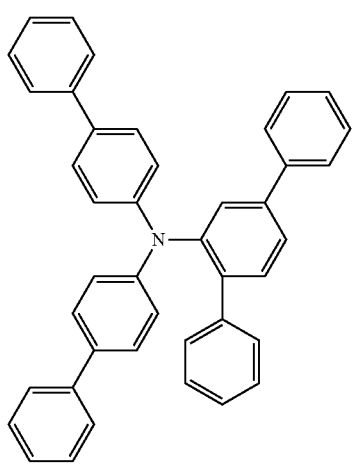
19
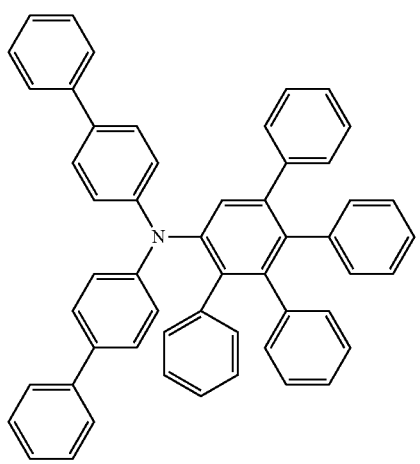
20
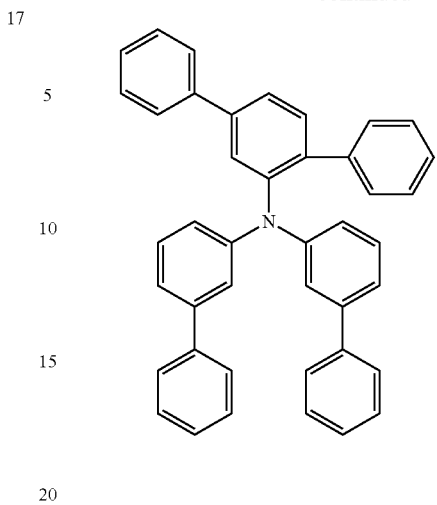
21
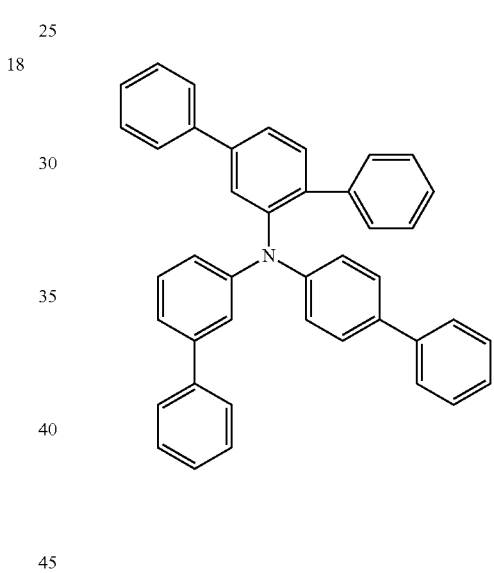
22
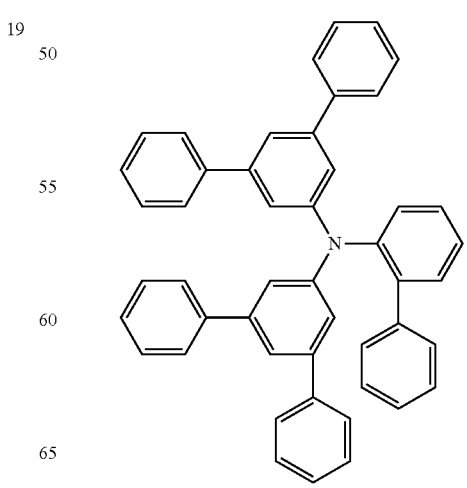

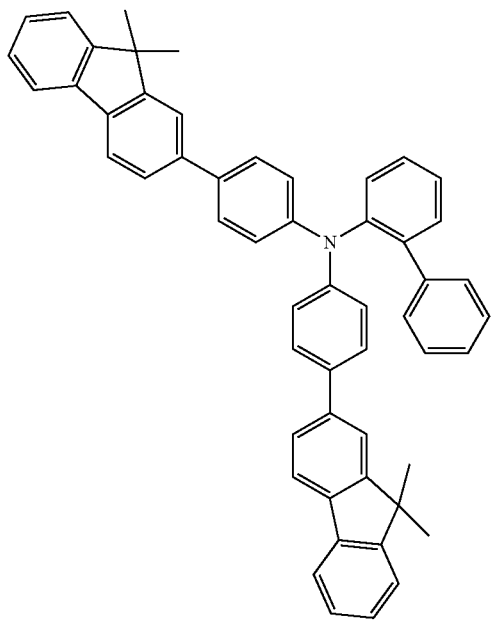
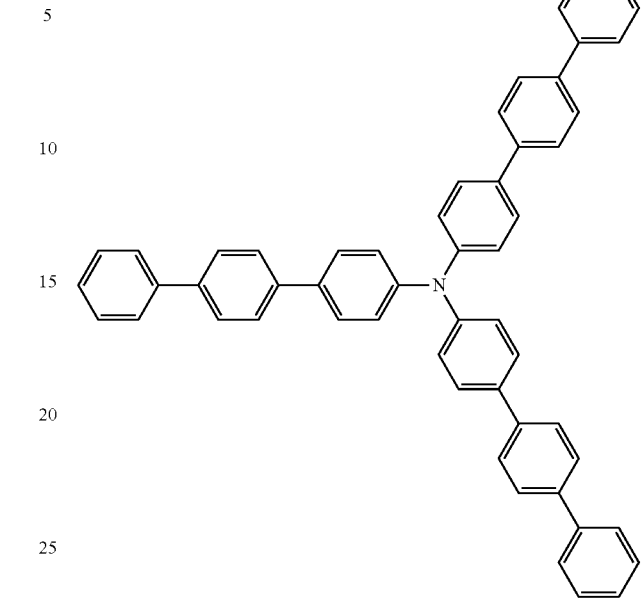
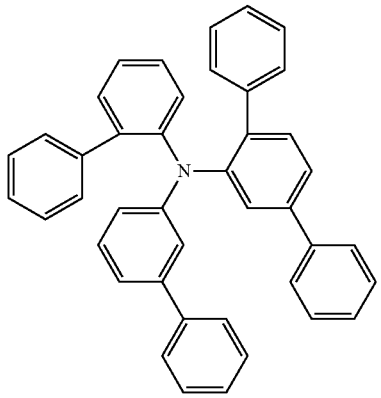
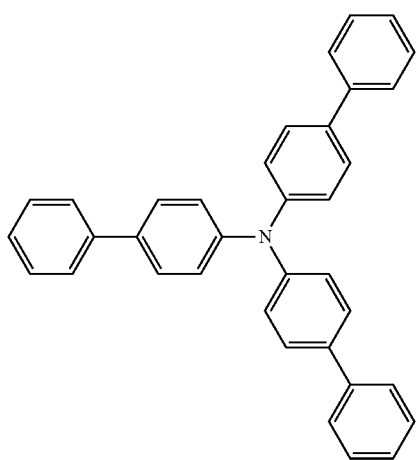
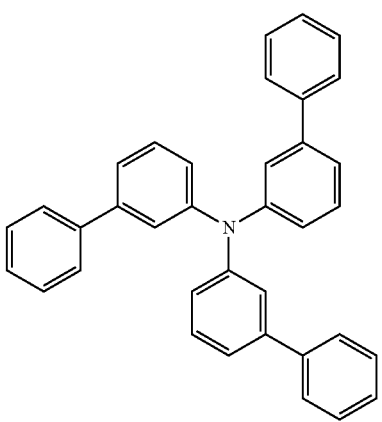

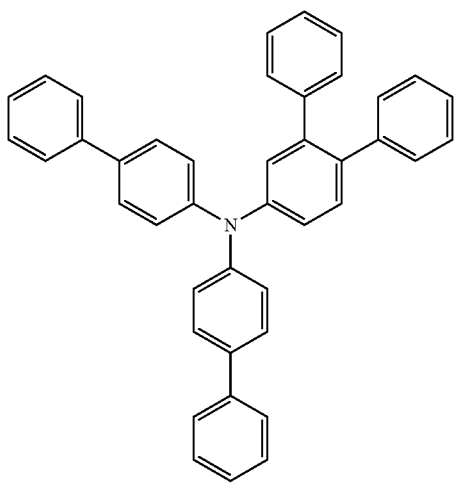
29
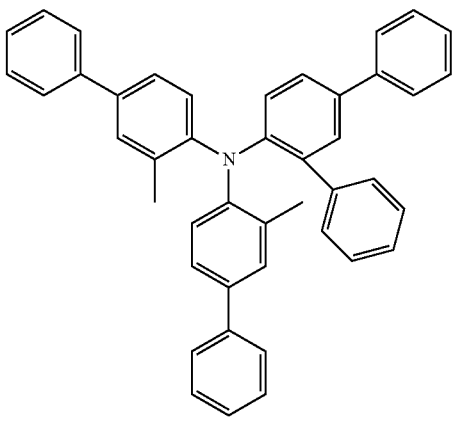
32
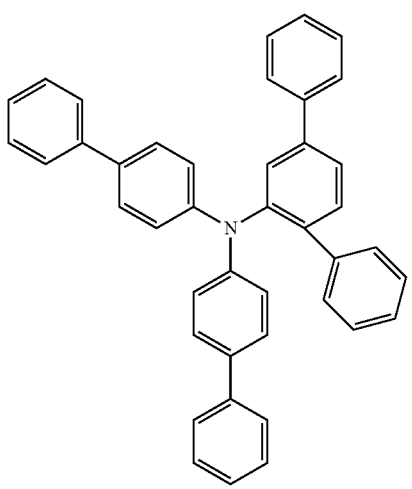
30
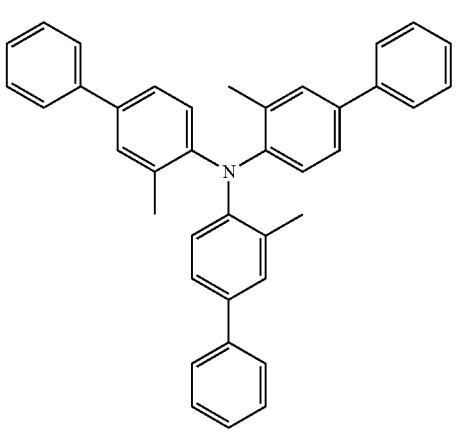
33
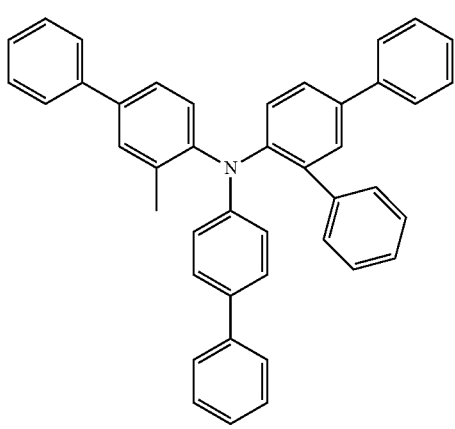
31
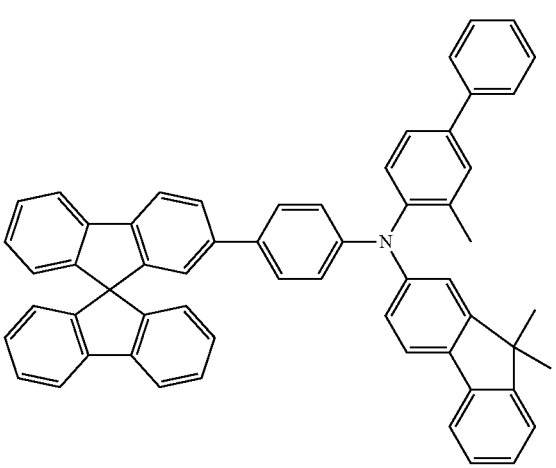
34

35
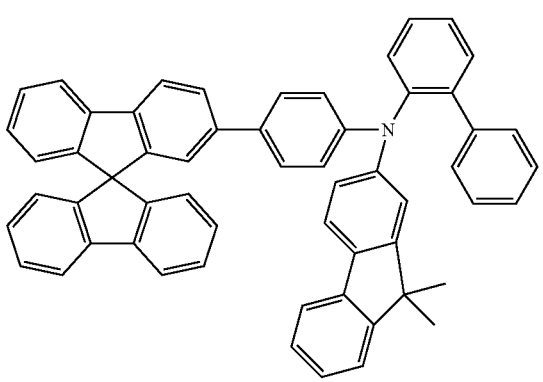
36
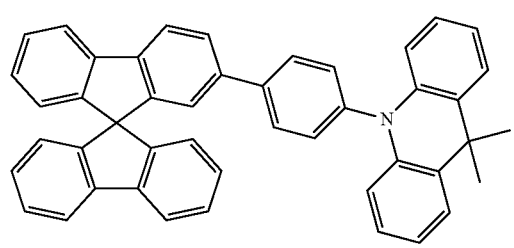
37
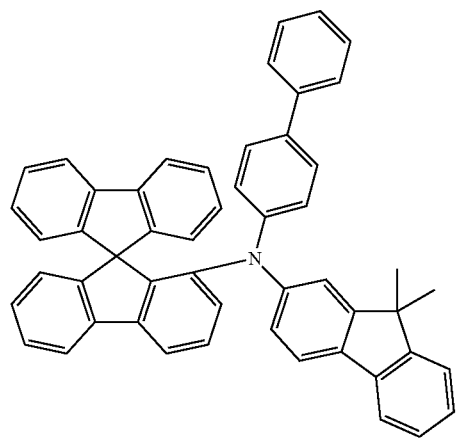
38
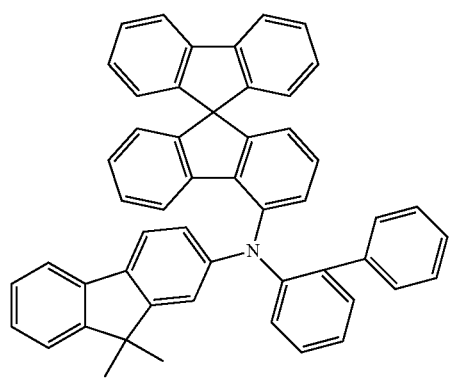
39
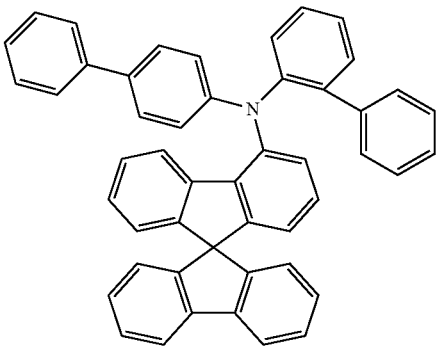
40
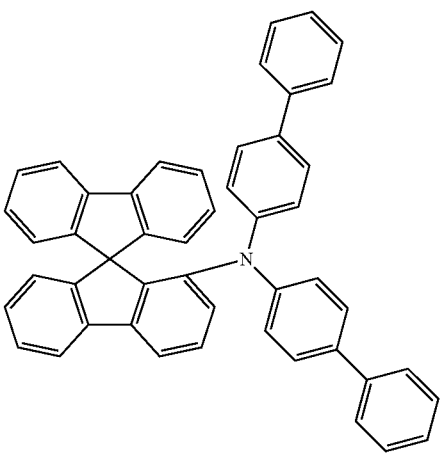
41
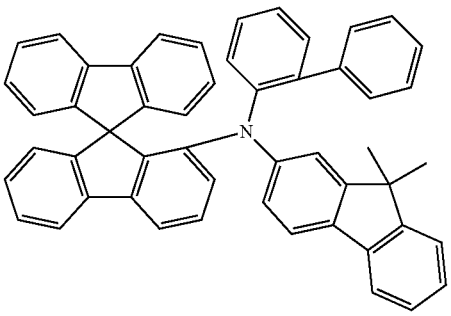
42
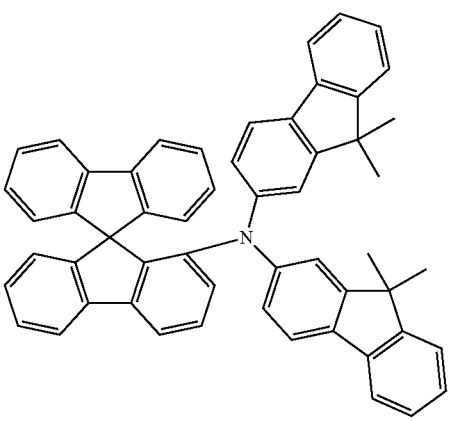

41
-continued
43
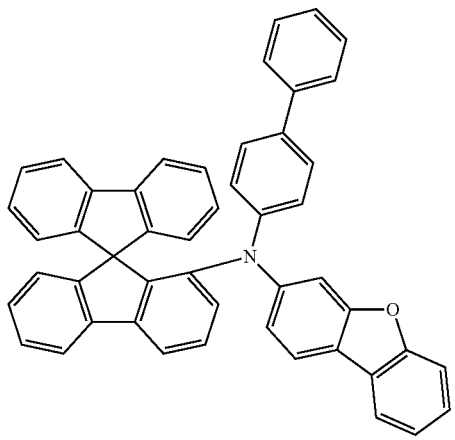
44
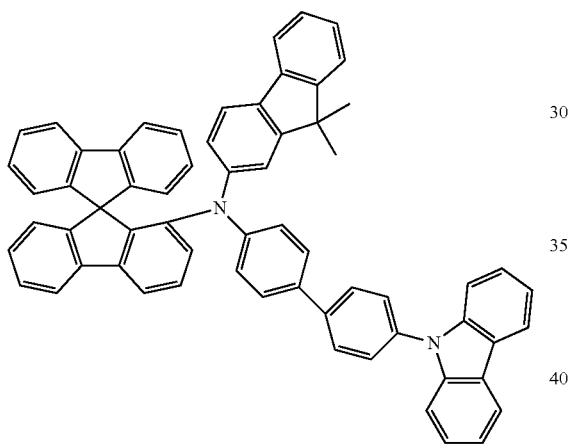
45
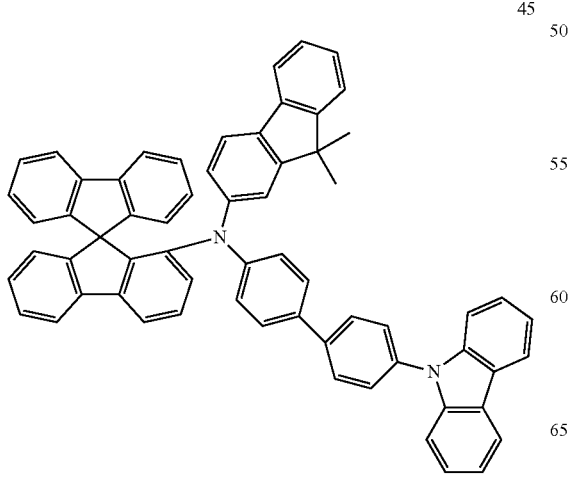
42
-continued
46
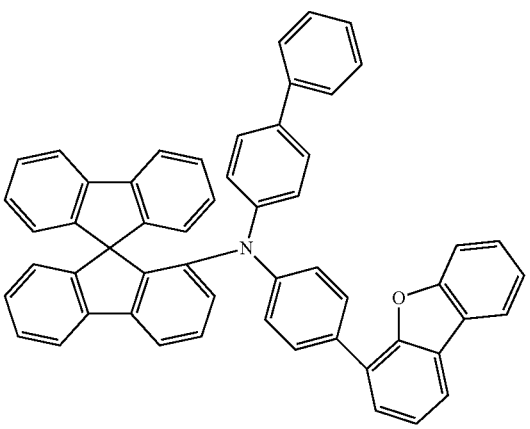
47
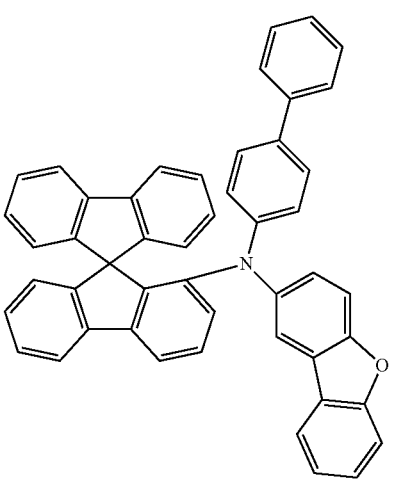
48
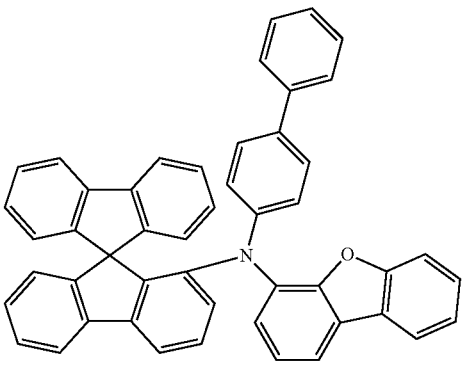

49
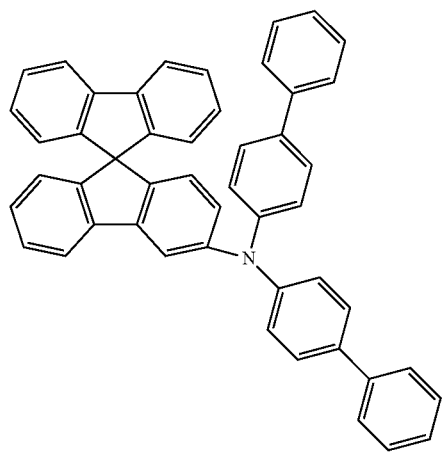
50
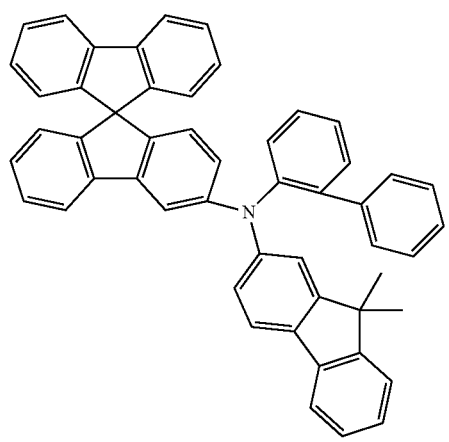
51
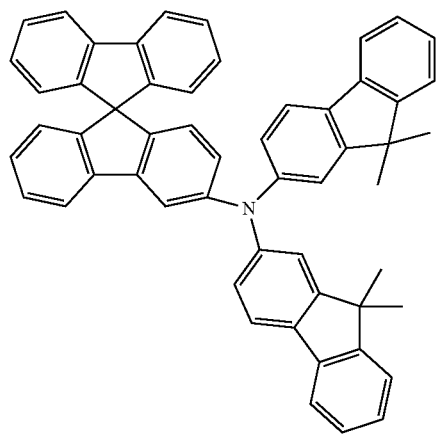
52
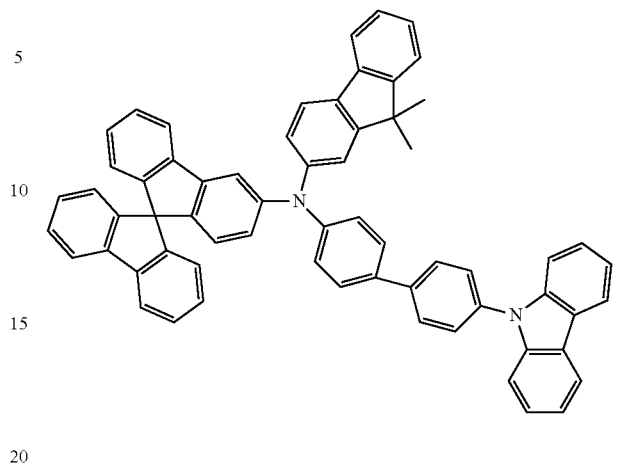
53
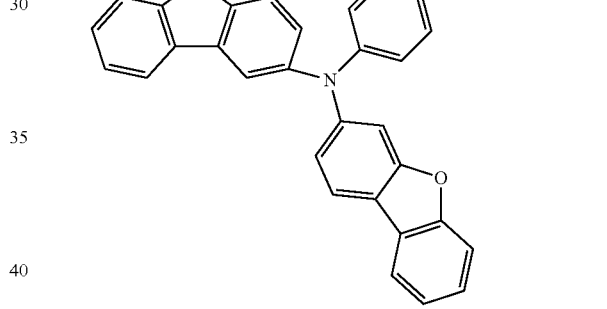
54
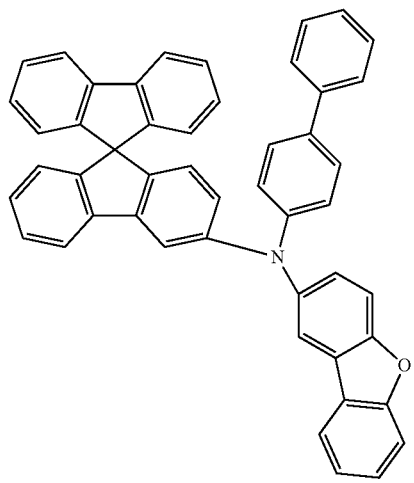

55
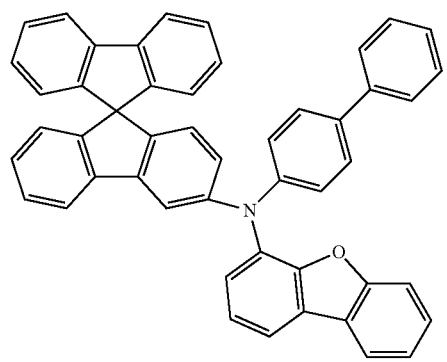
56
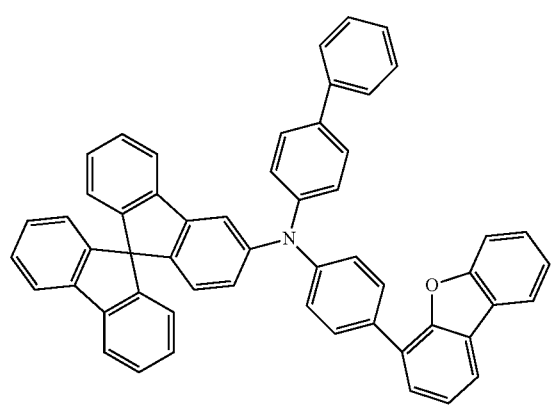
57
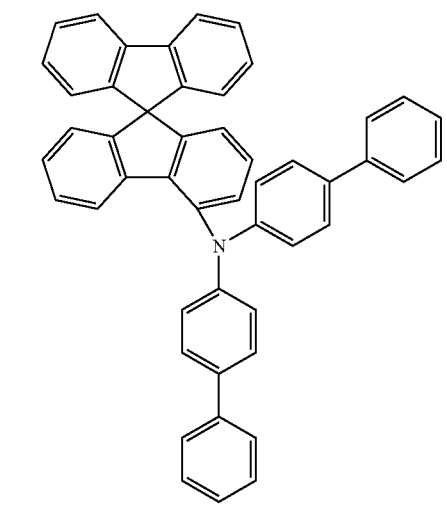
58
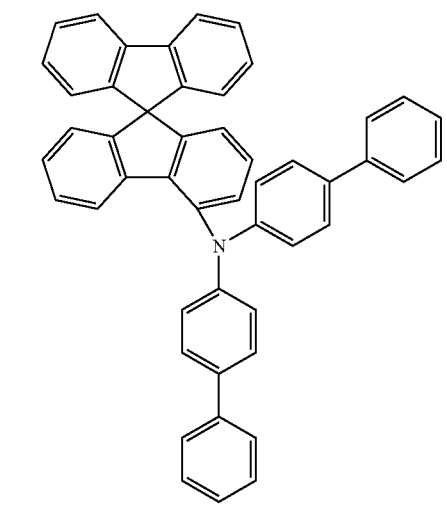
59
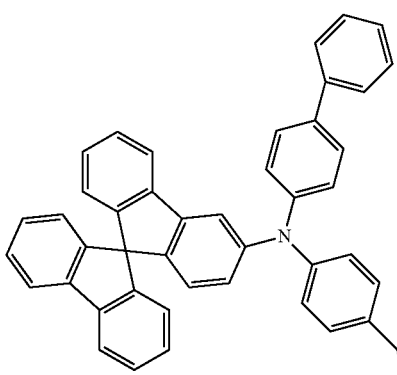
60
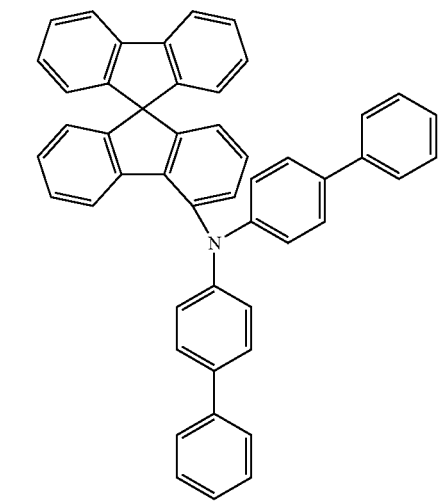
61
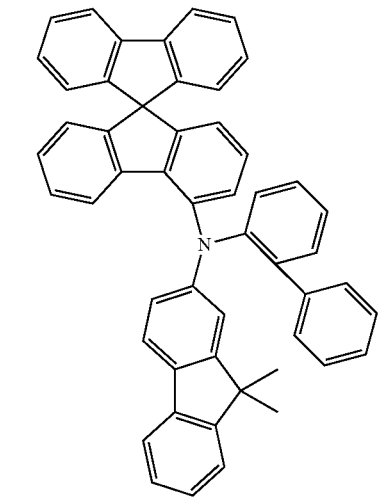

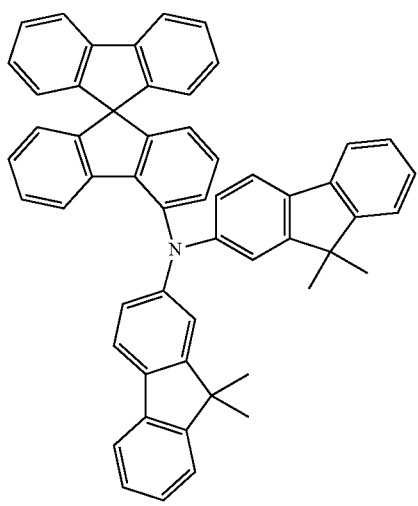
62
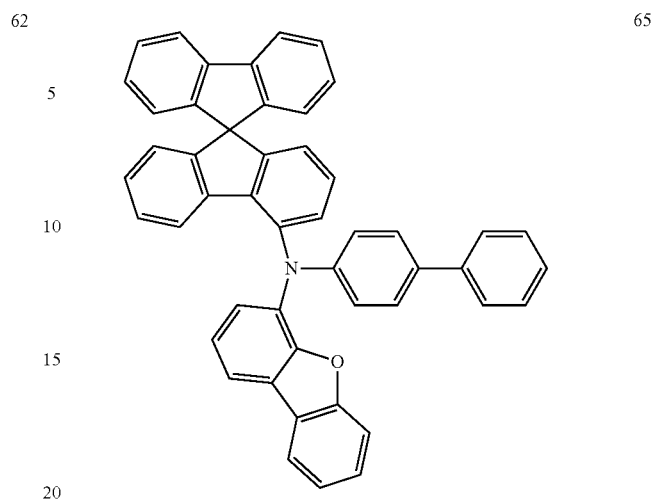
65
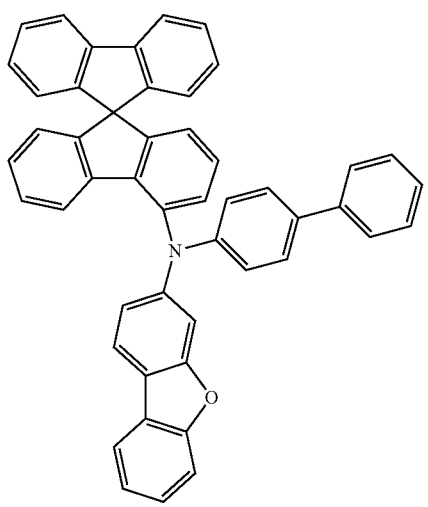
63
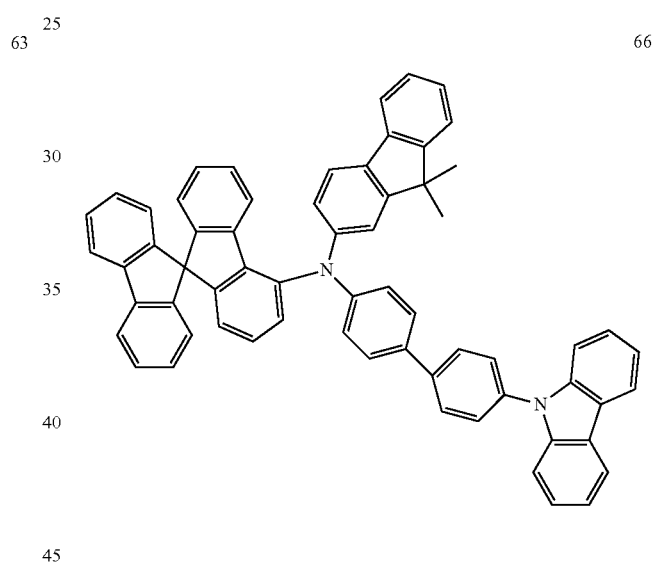
66
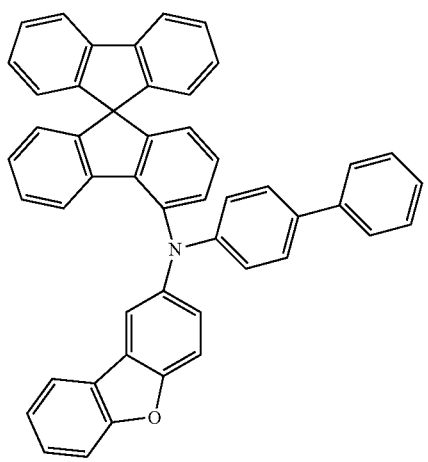
64
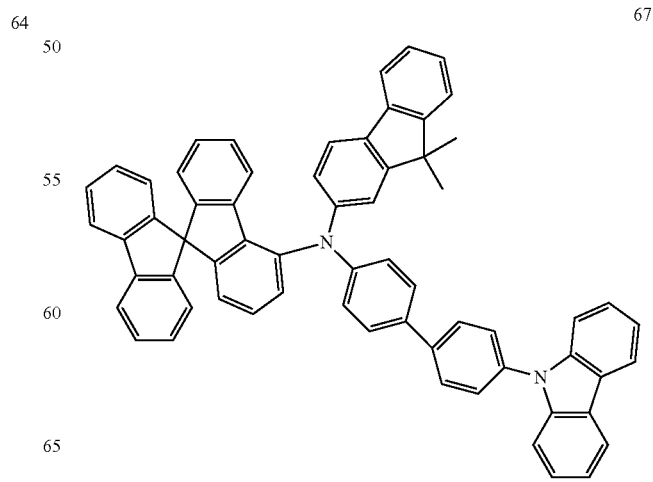
67

68
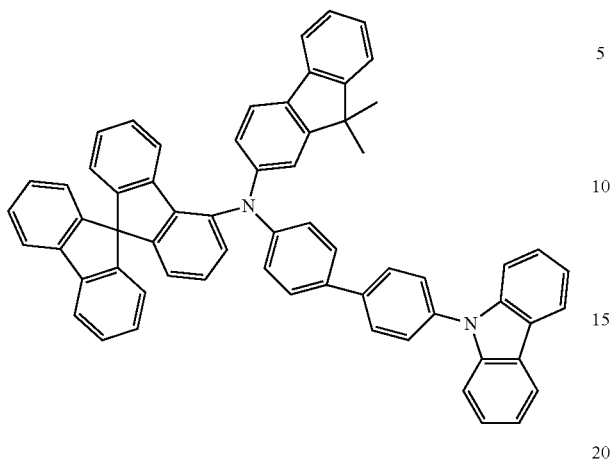
69
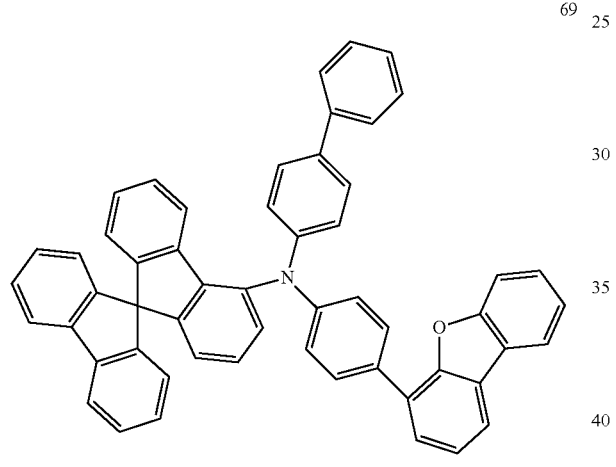
70
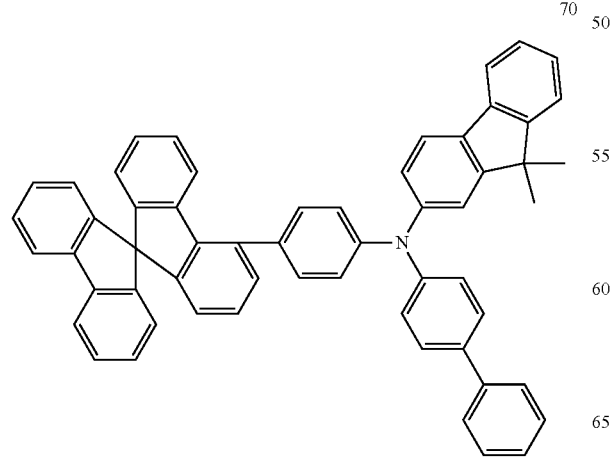
71
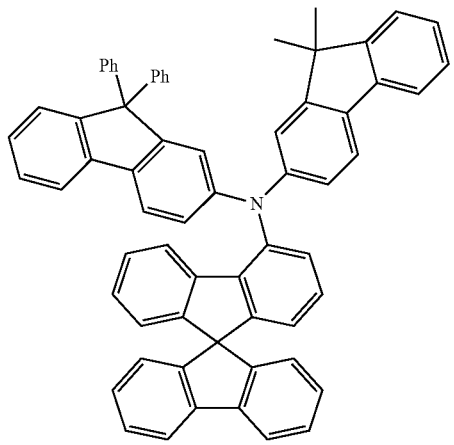
72
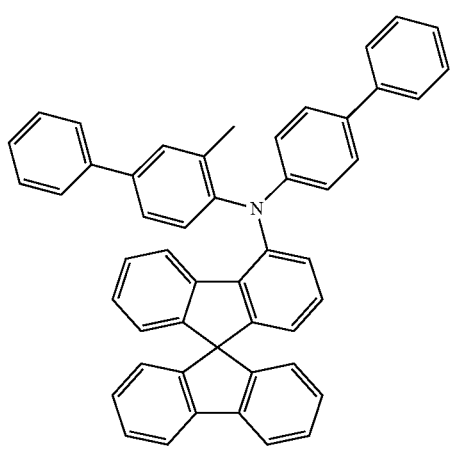
73
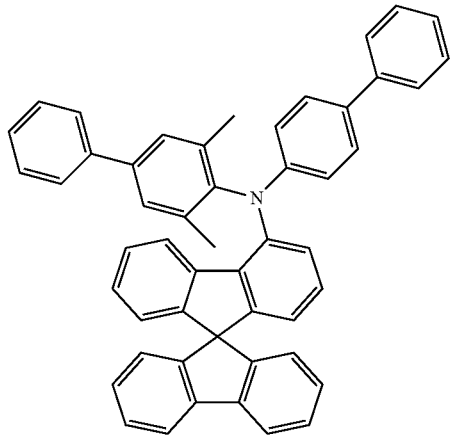

74
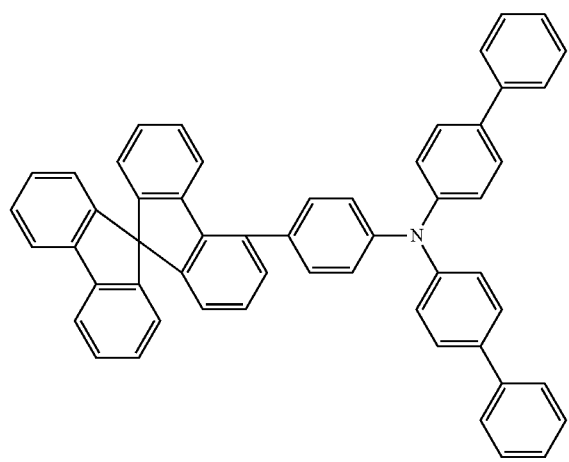
77
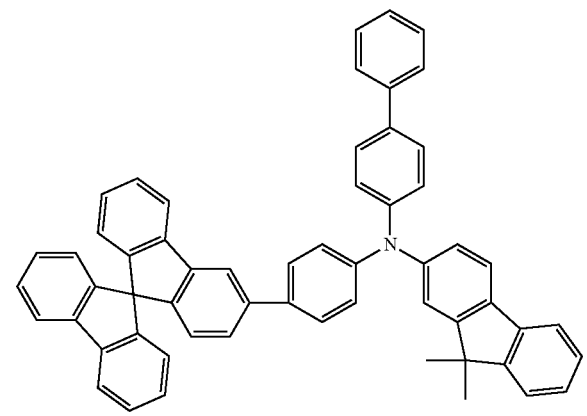
75
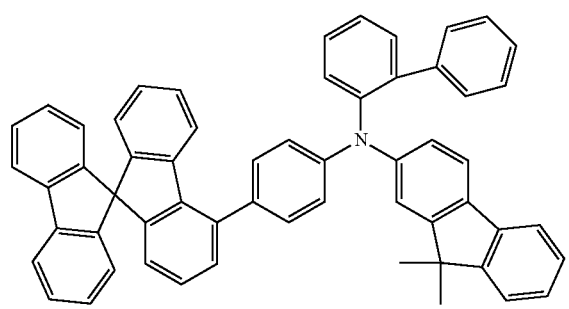
78
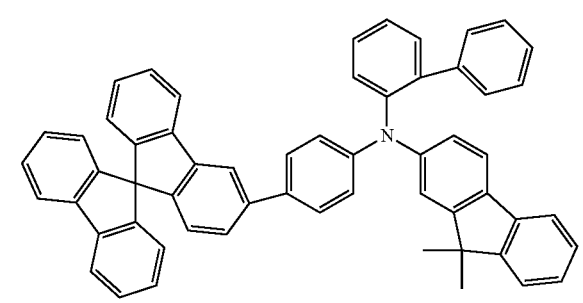
76
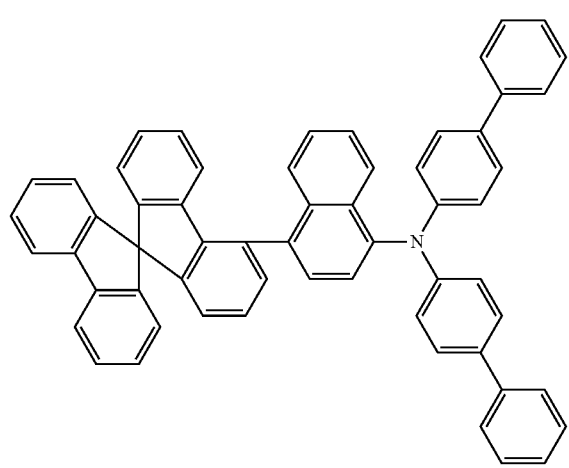
79
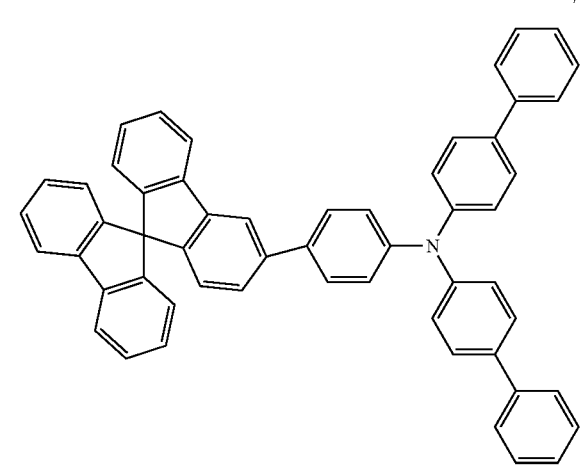

80
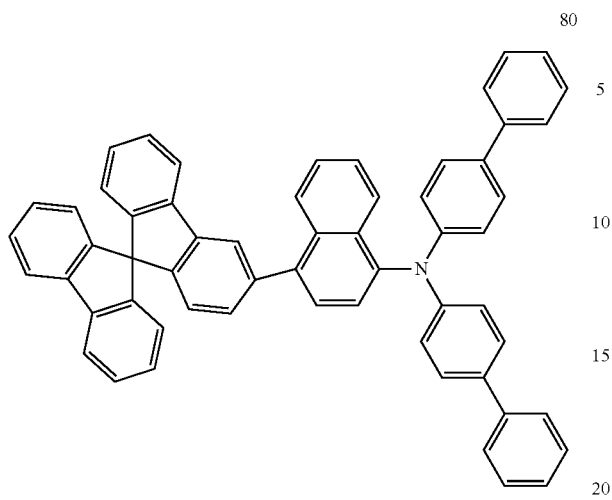
81
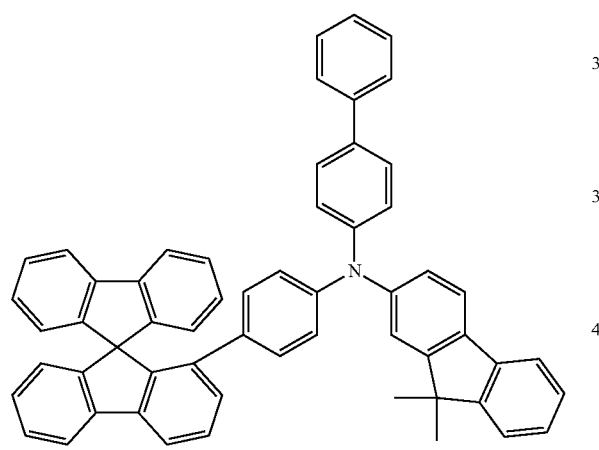
82
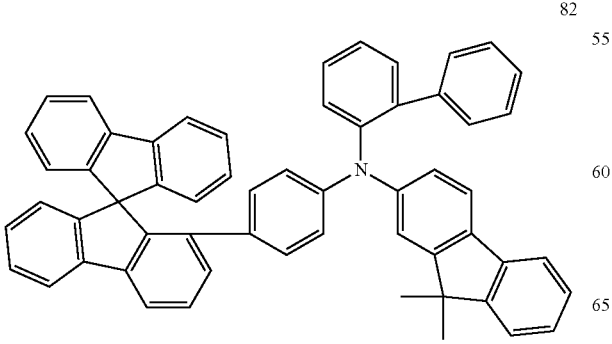
83
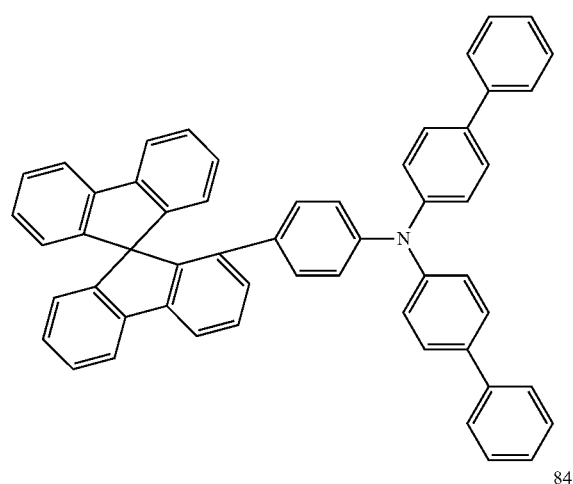
84
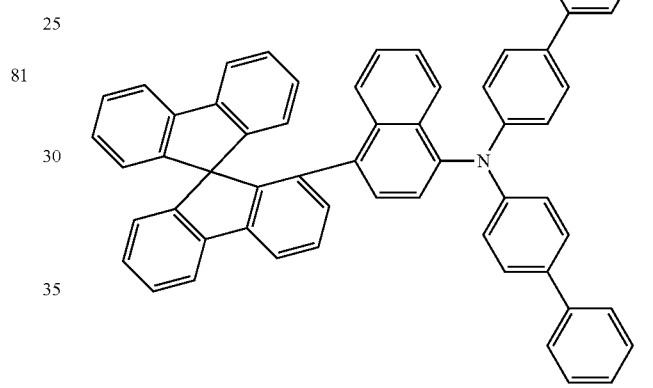
85
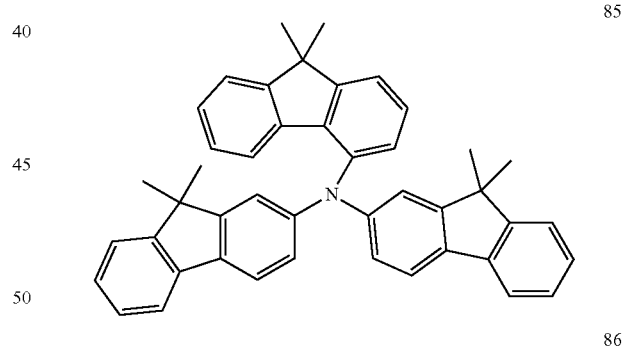
86
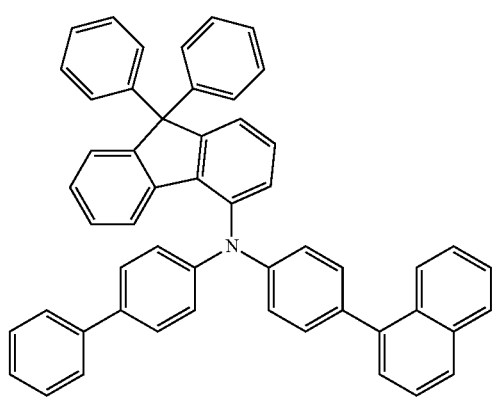

87
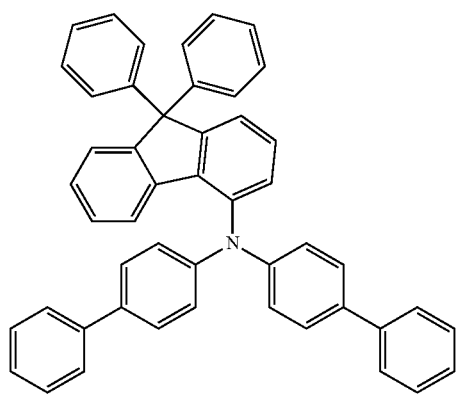
88
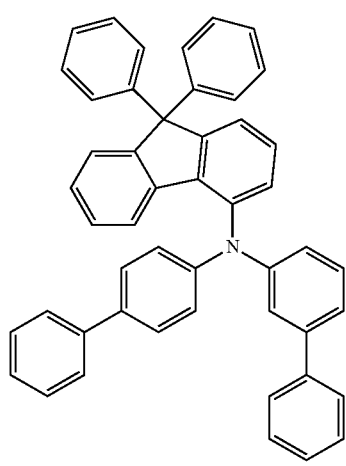
89
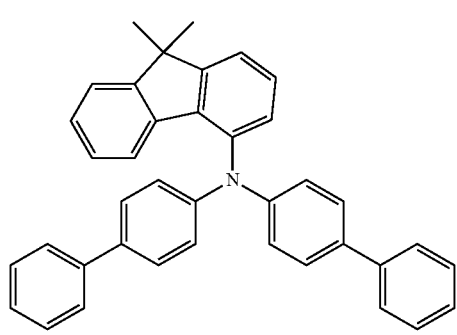
90
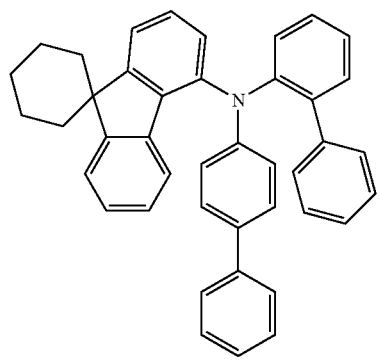
91
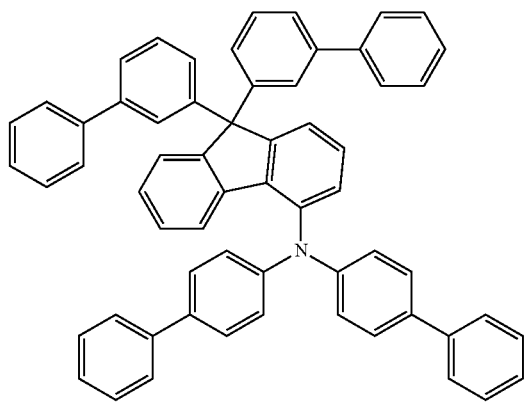
92
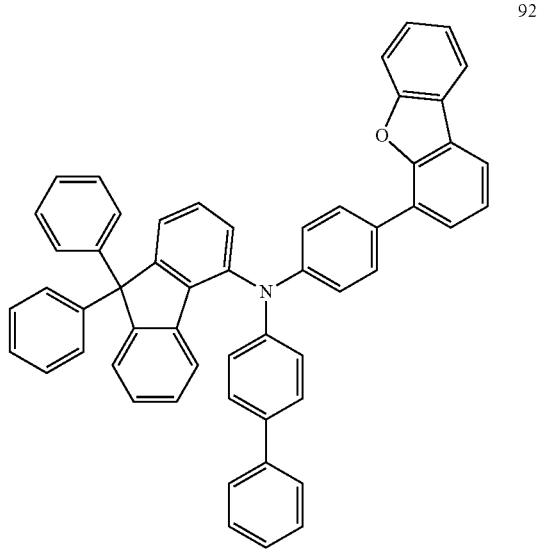
93
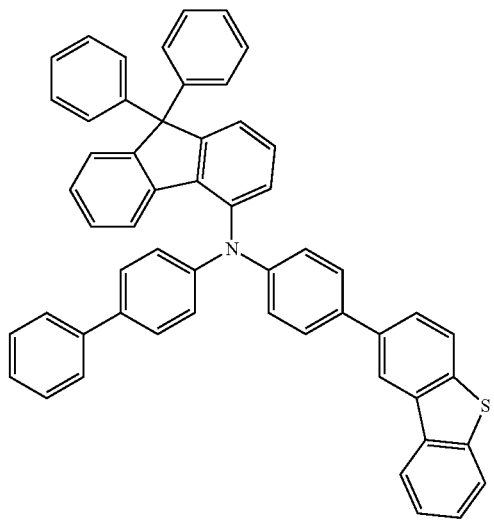

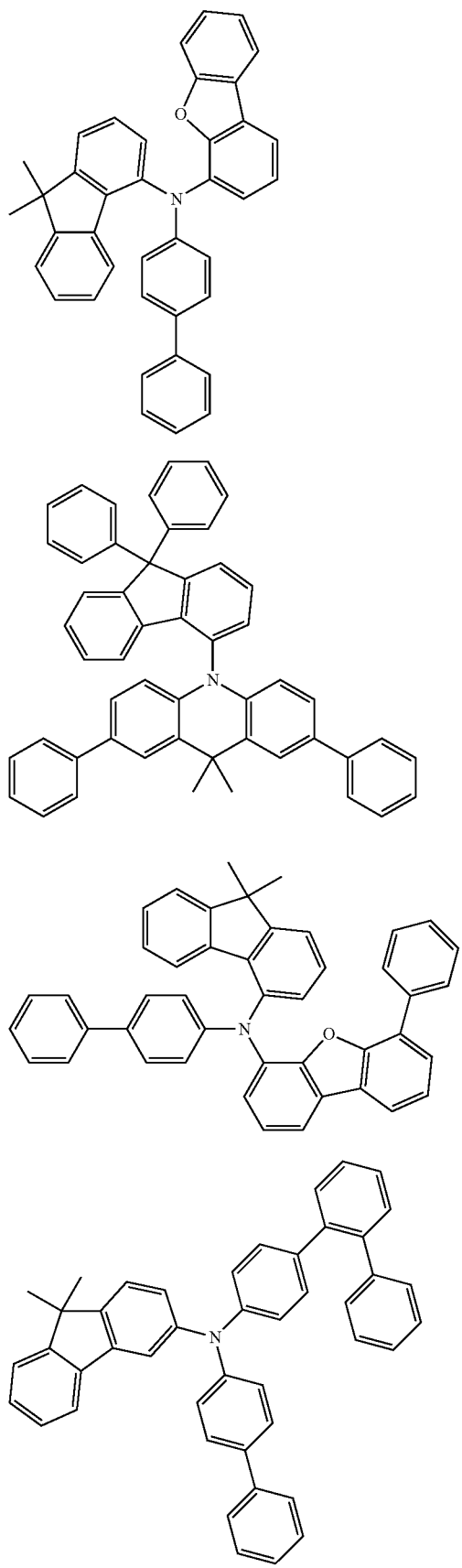
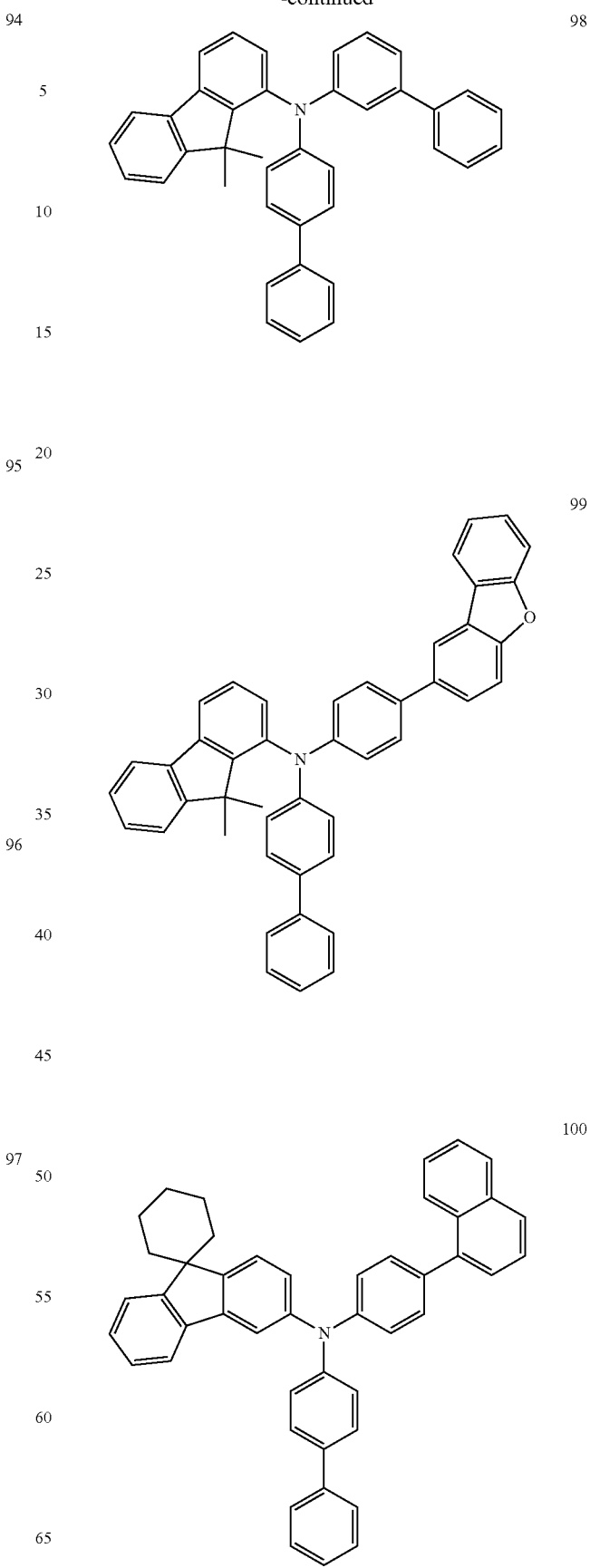

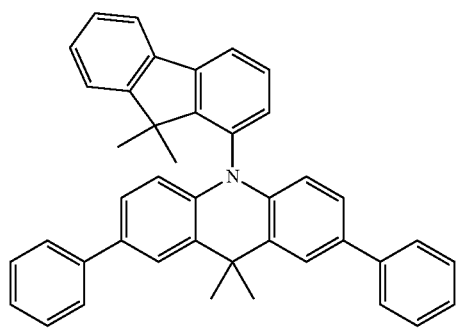
101
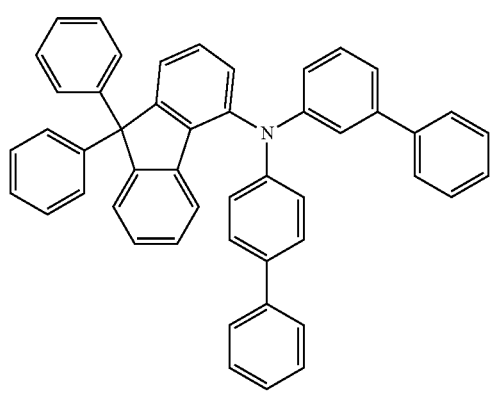
102
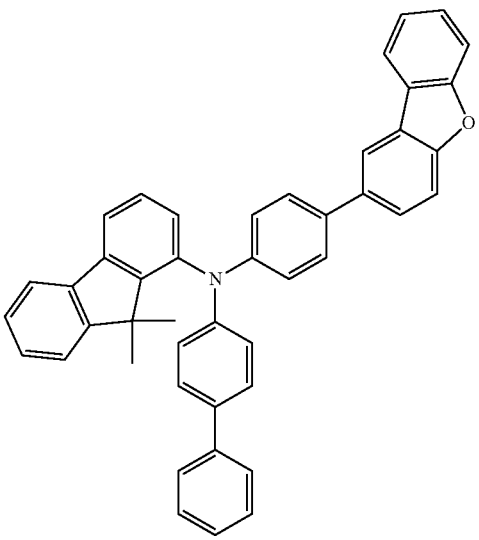
105
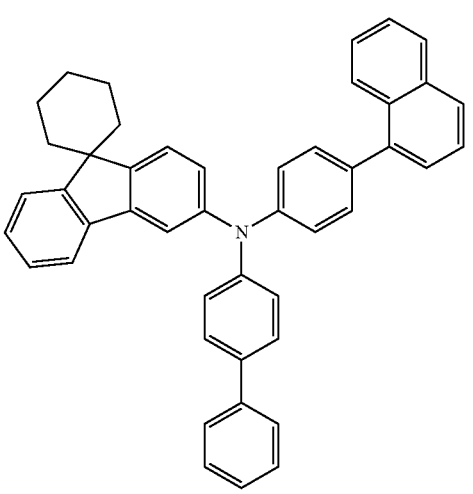
106
103
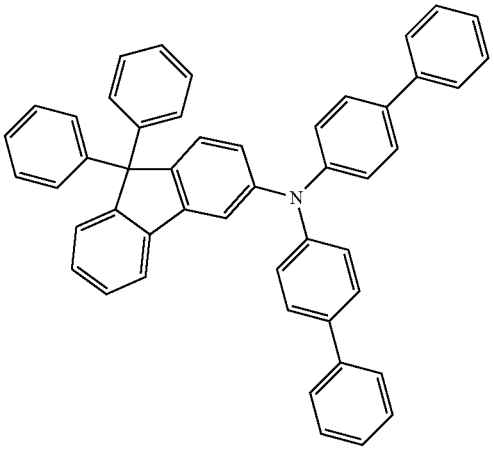
107
104

108
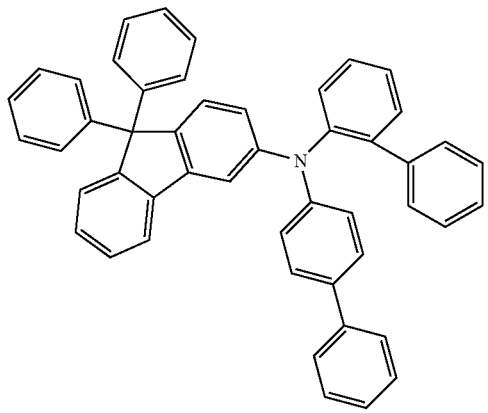
111
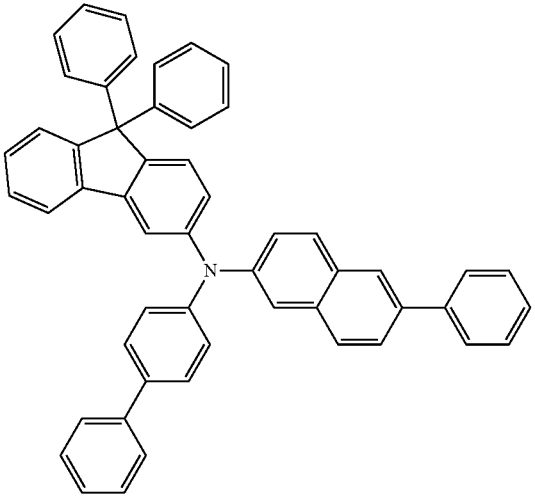
109
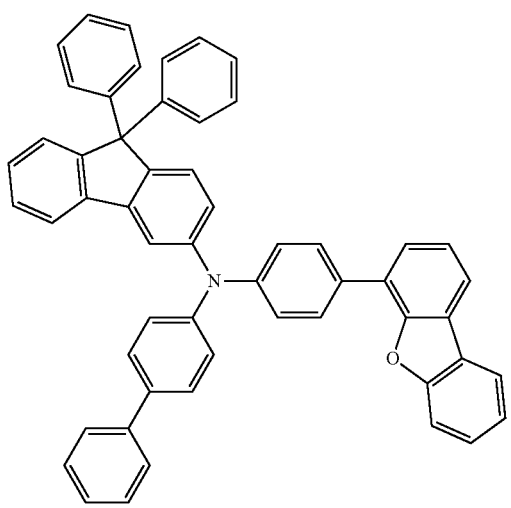
112
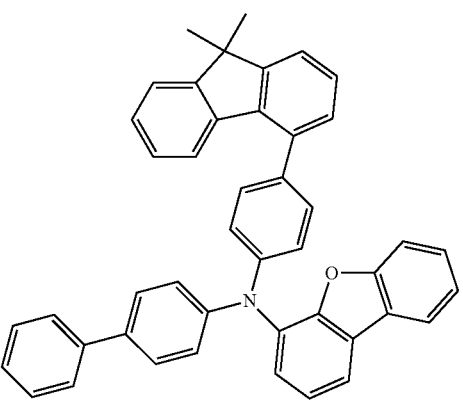
110
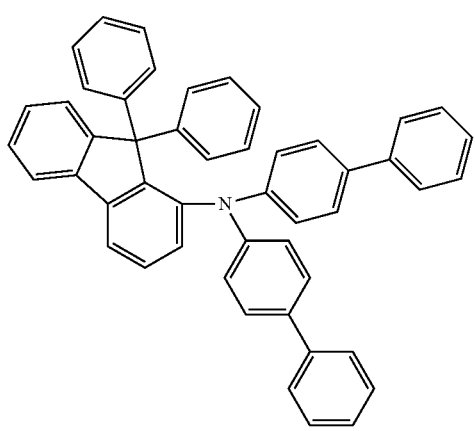
113
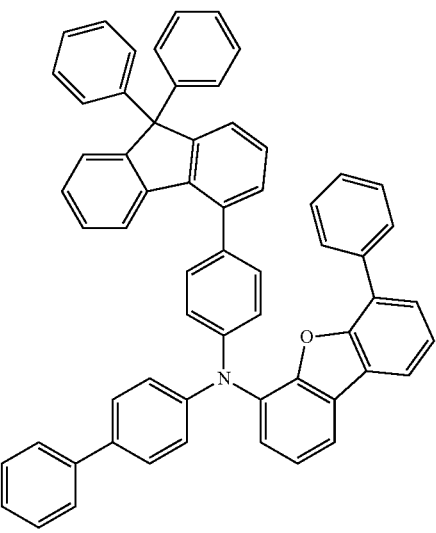

114
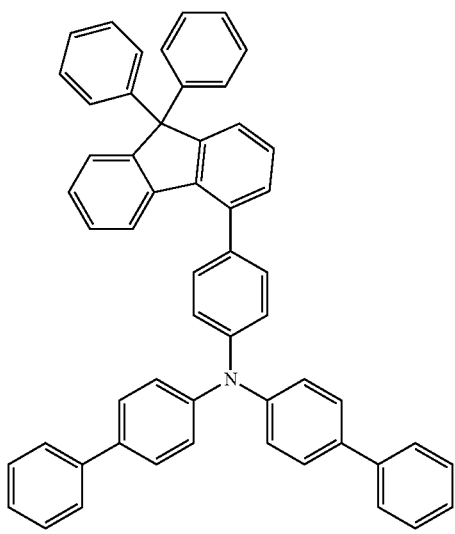
115
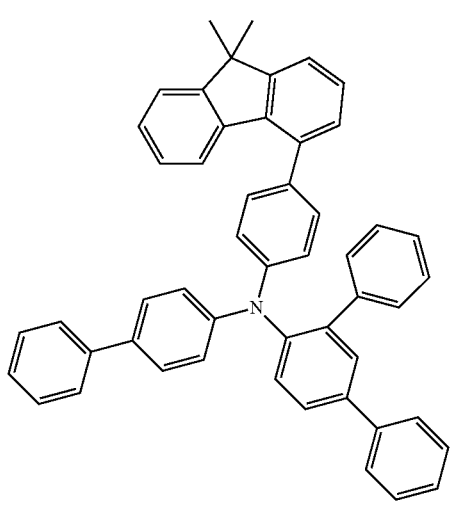
116
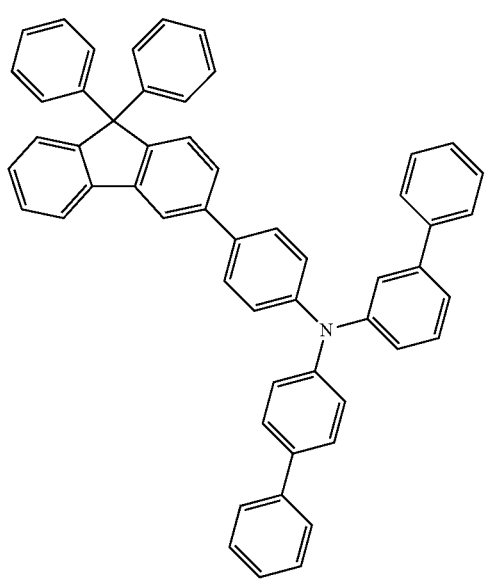
117
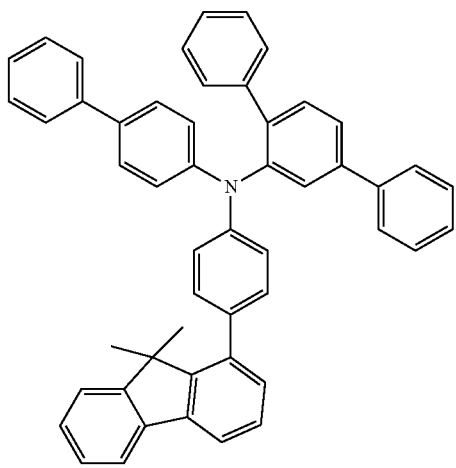
118
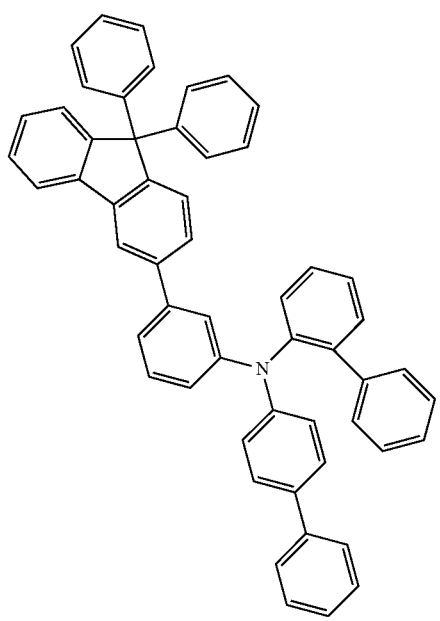

119
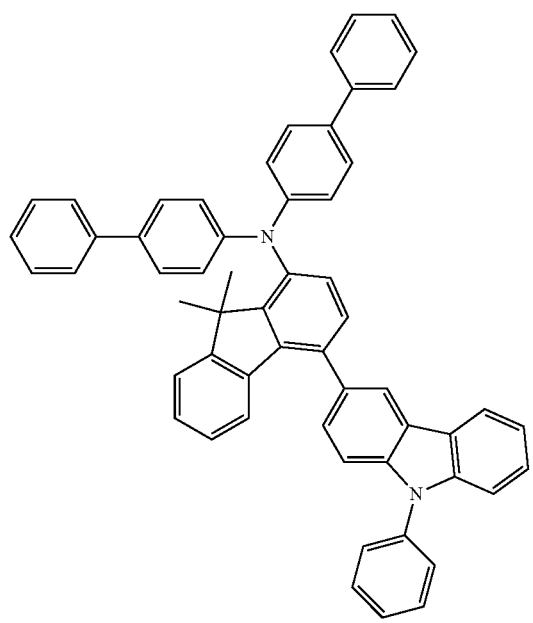
120
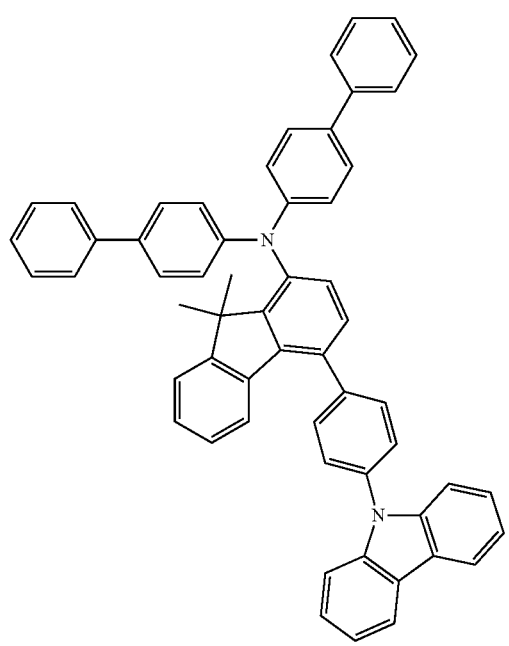
121
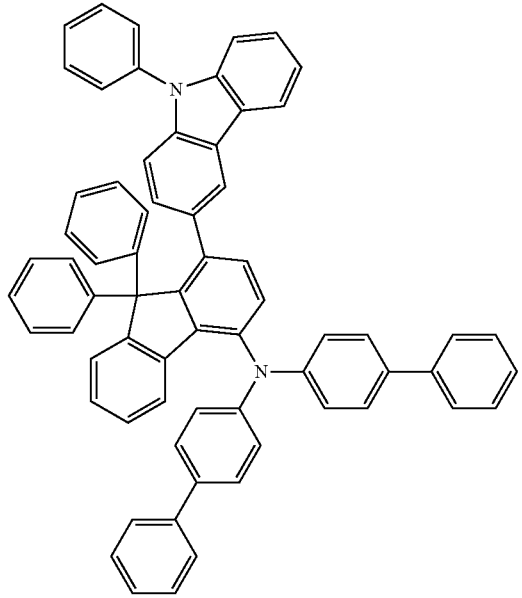
122
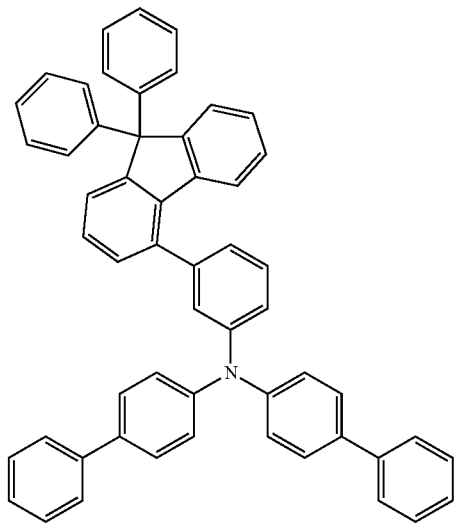
123

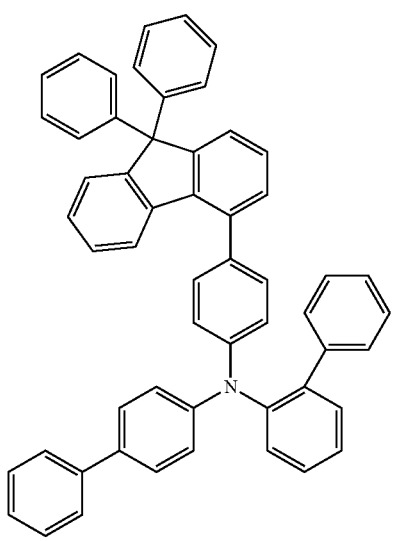
124
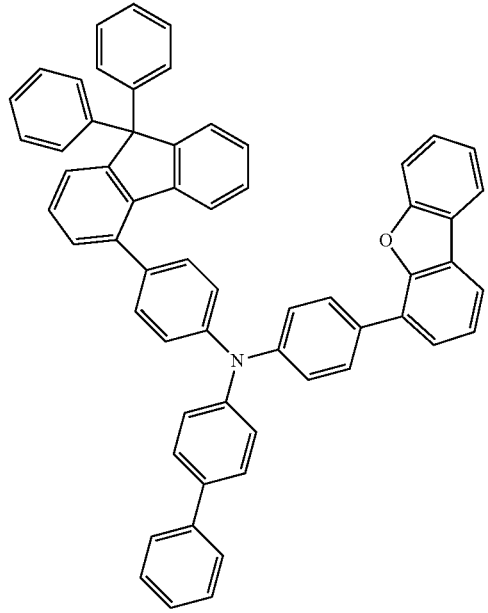
126
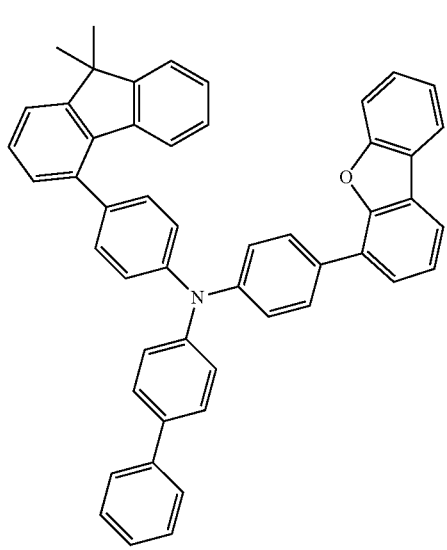
125
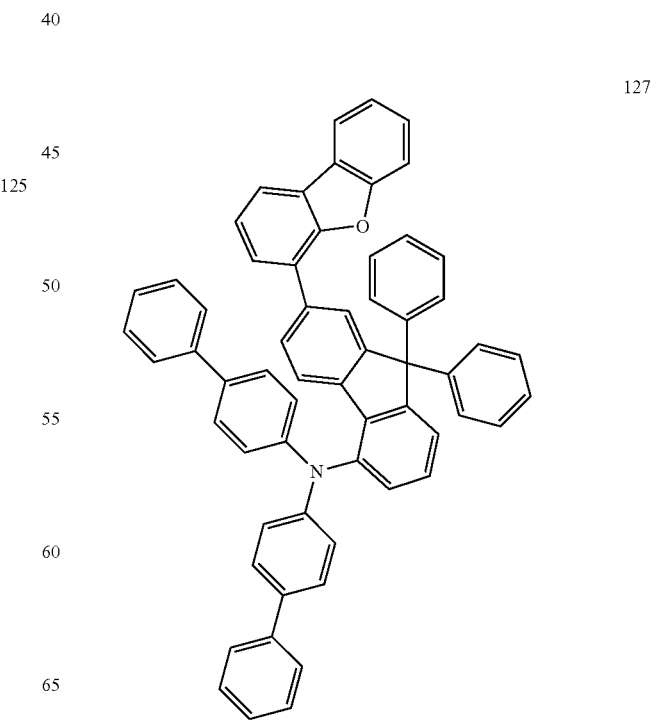
127

-continued
128 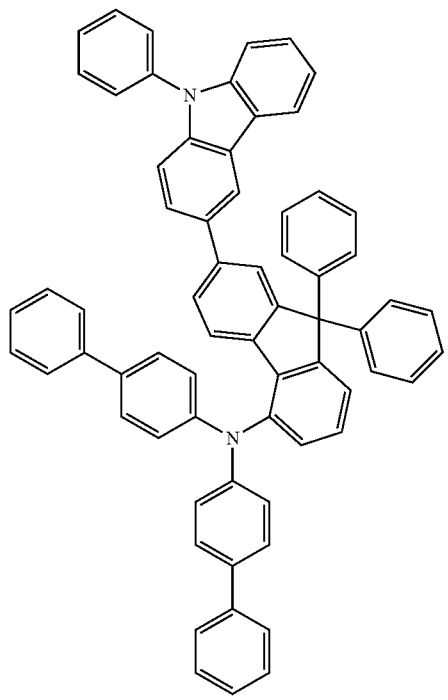
-continued
130 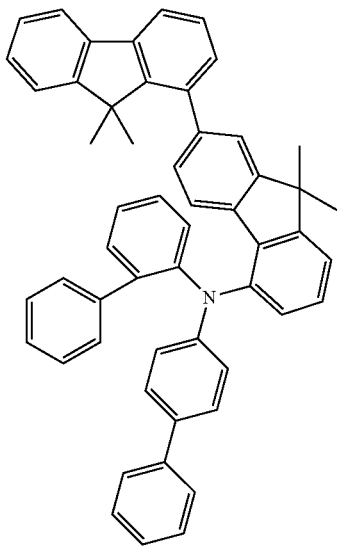
131 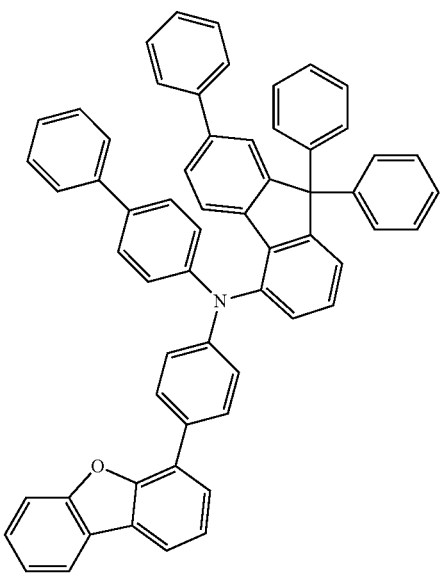
129 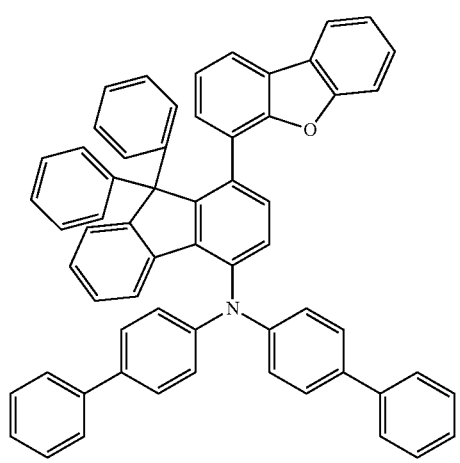
132

133
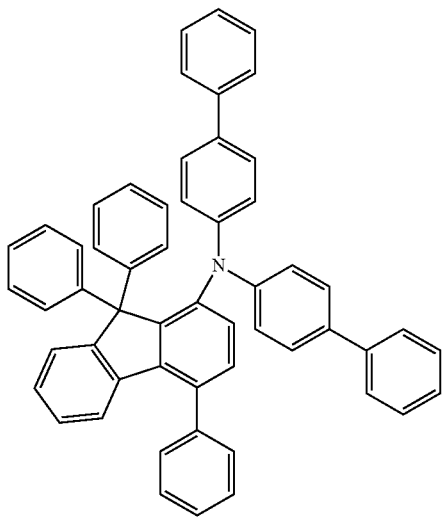
134
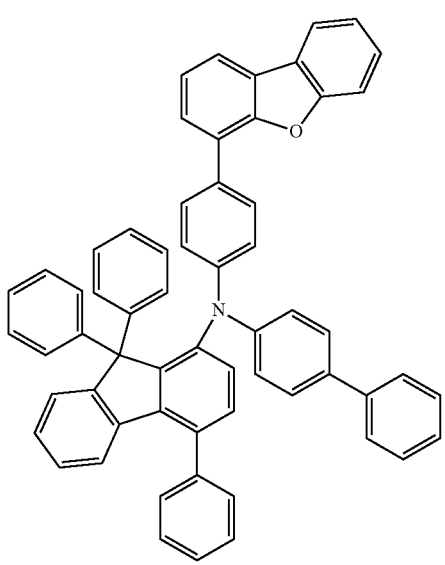
135
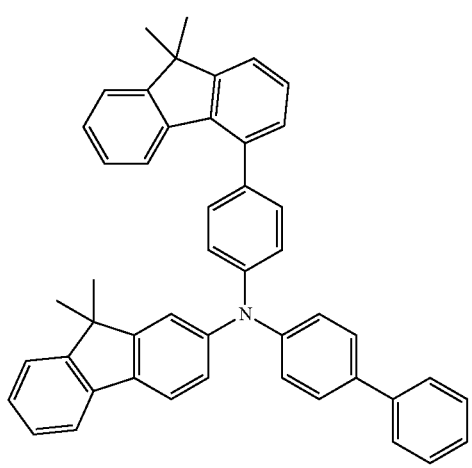
136
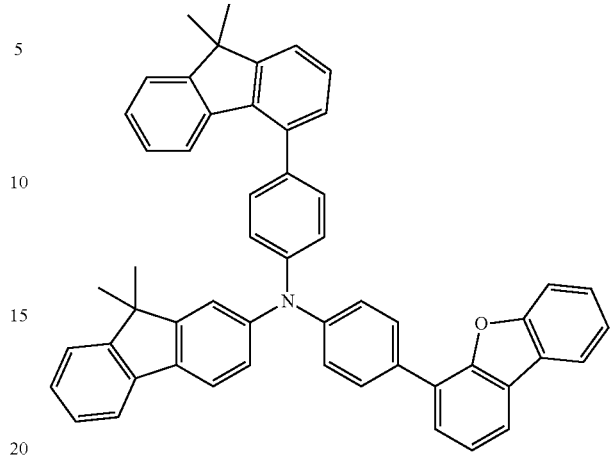
137
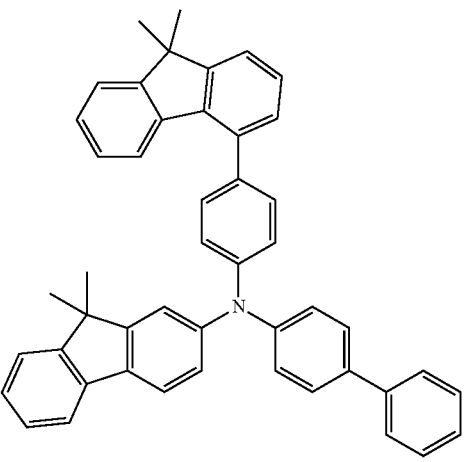
138
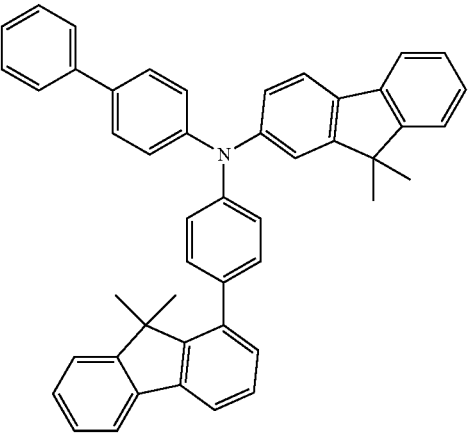

139
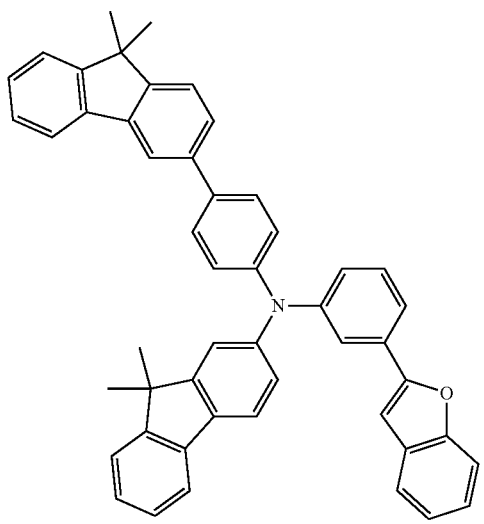
140
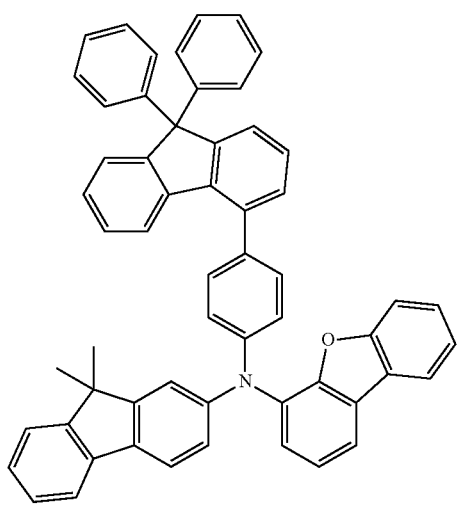
141
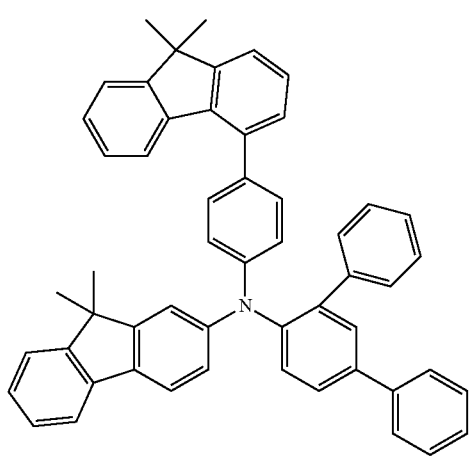
142
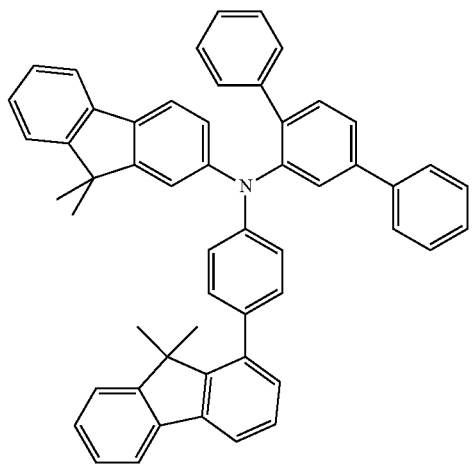
143
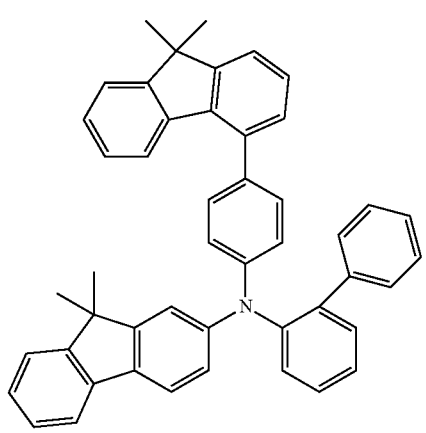
144
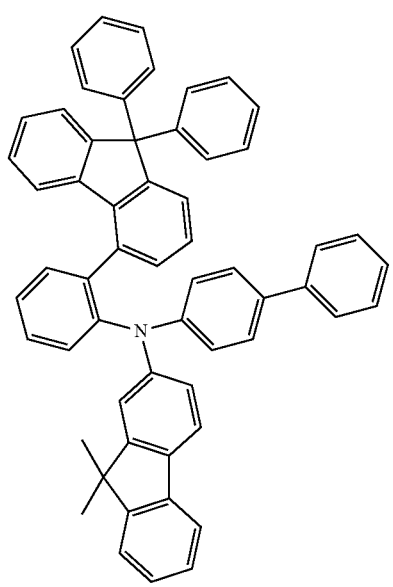

145
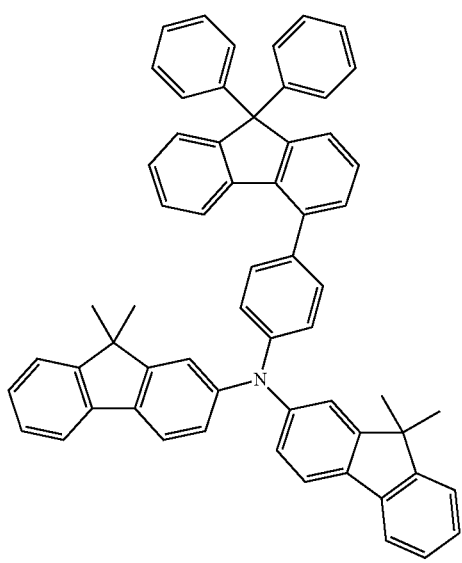
146
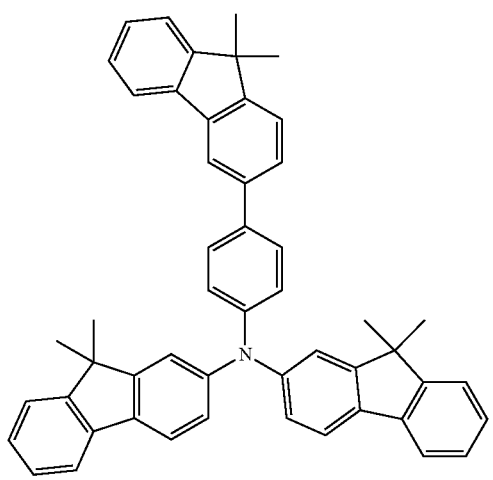
147
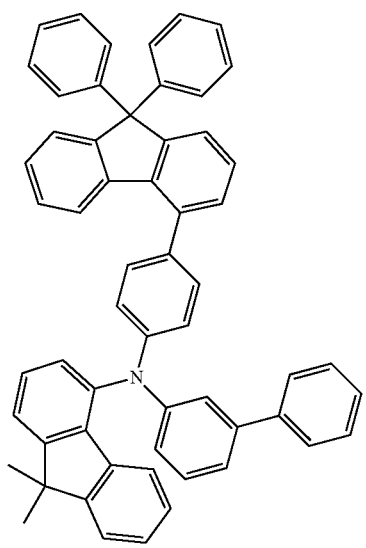
148
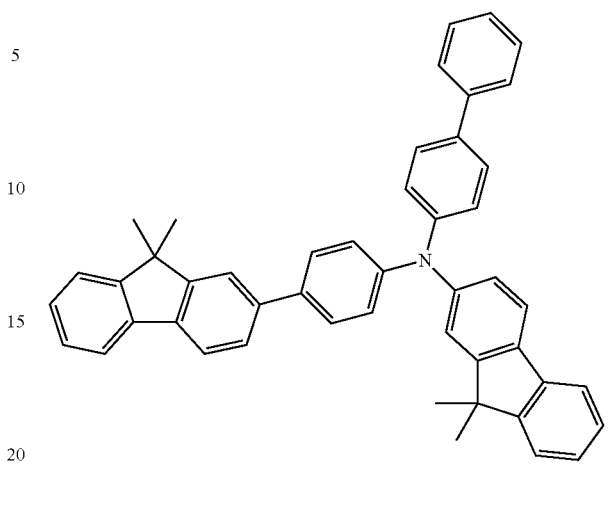
149
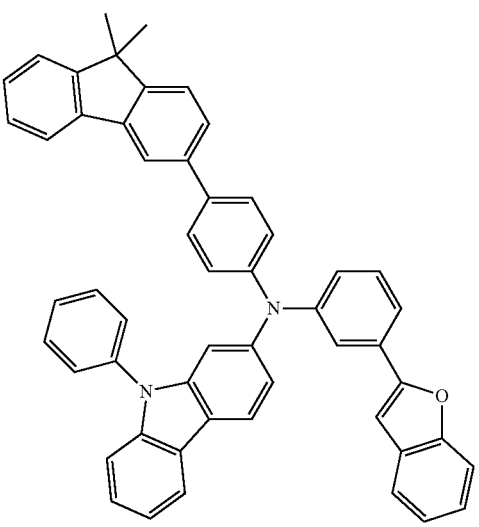
150

151
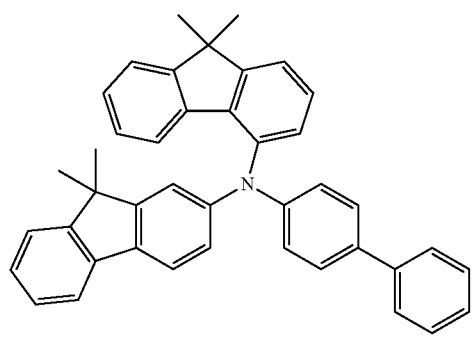
152
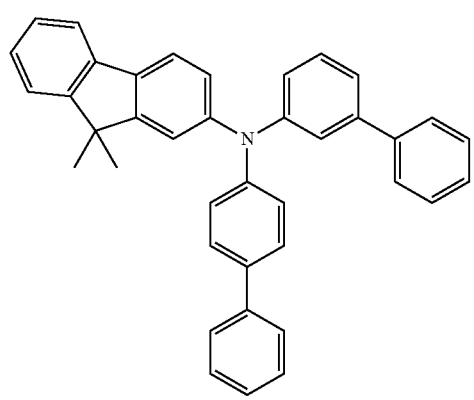
153
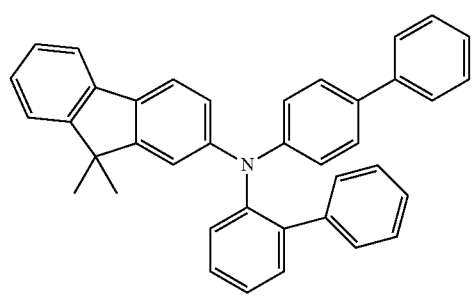
154
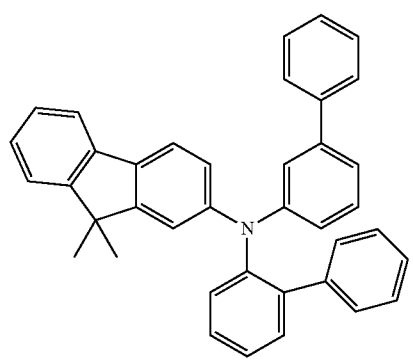
155
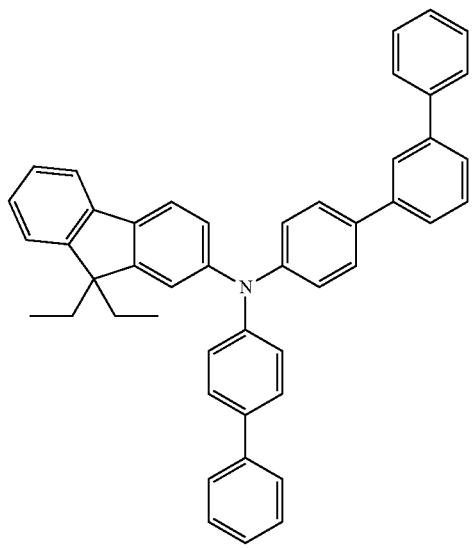
156
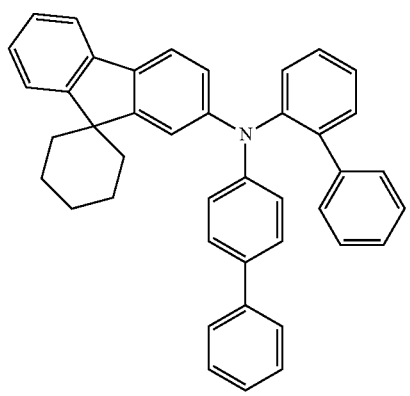
157
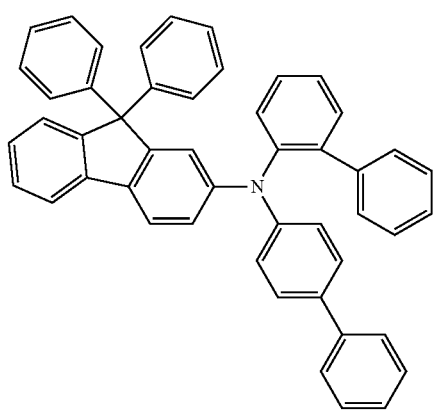

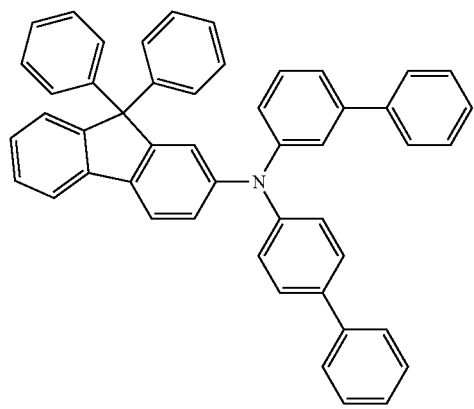
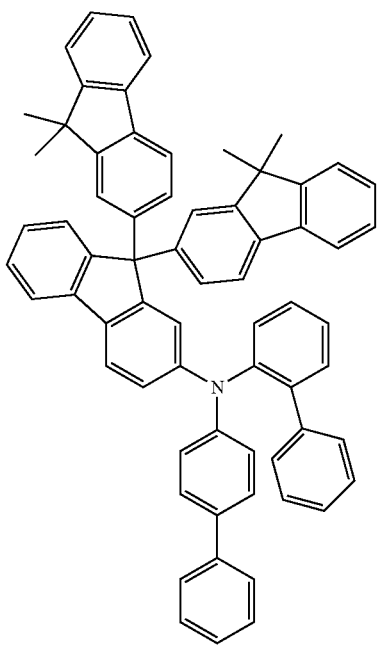
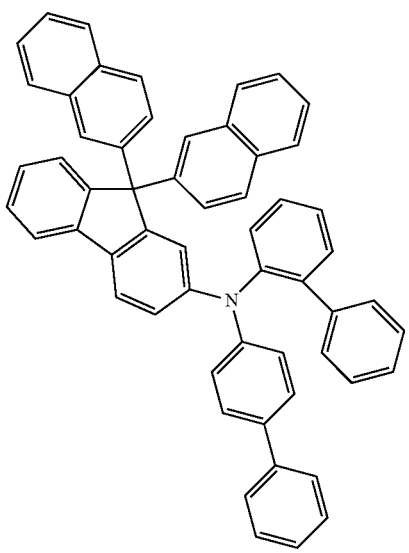
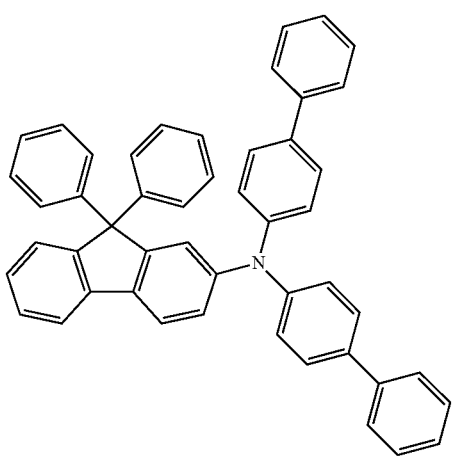

164
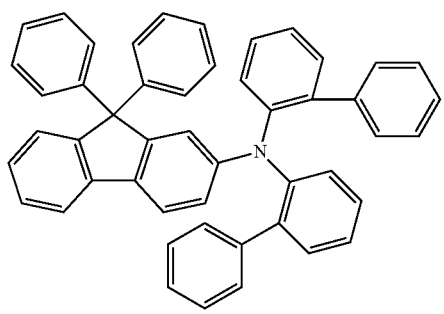
165
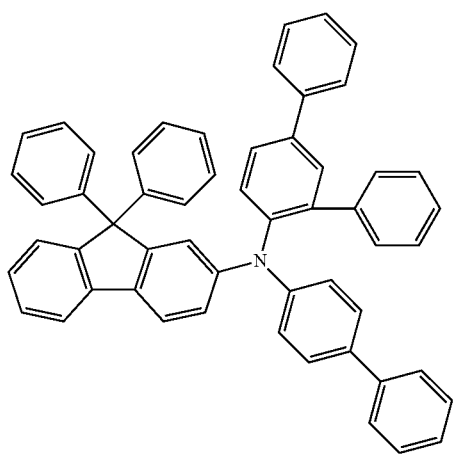
166
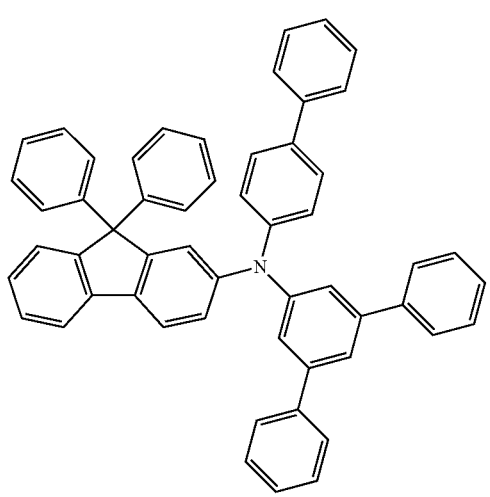
167
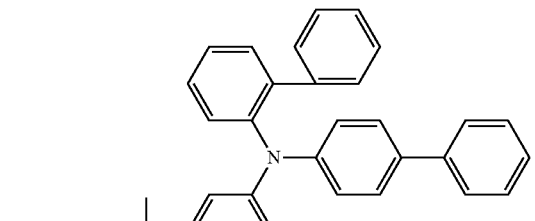
168
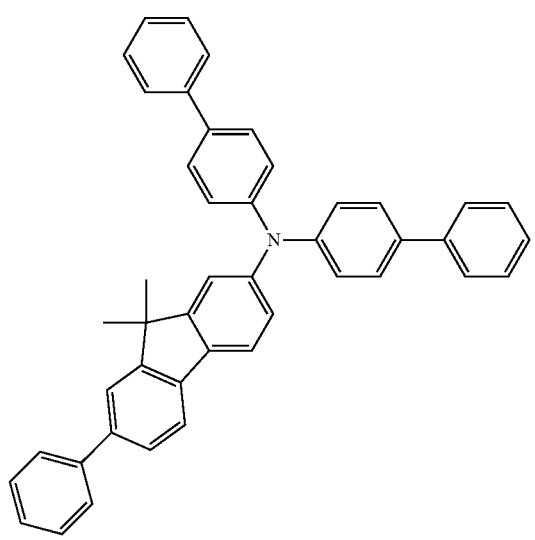
169
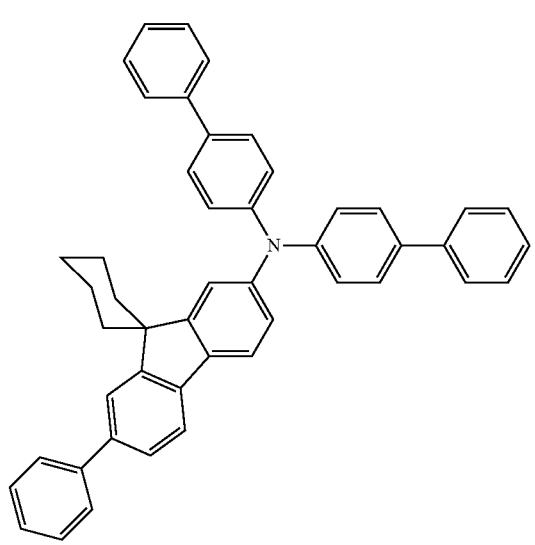

170
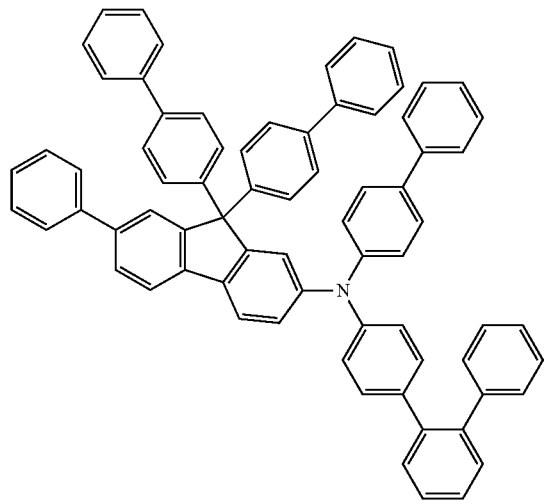
171
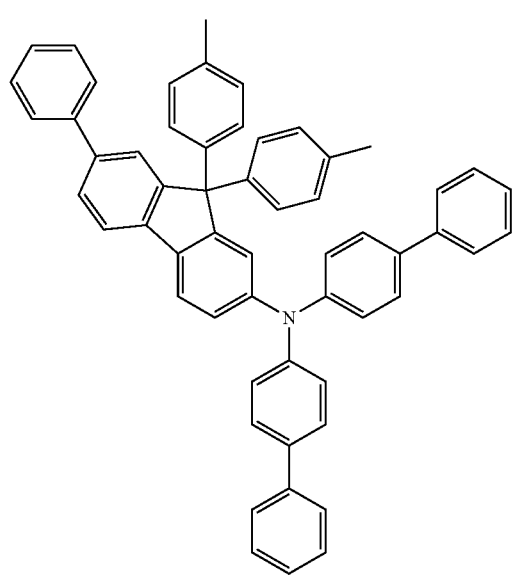
172
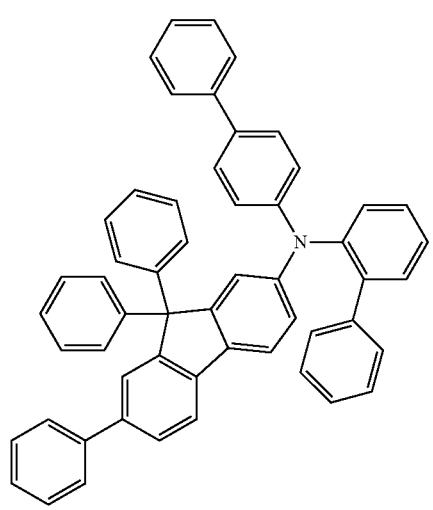
173
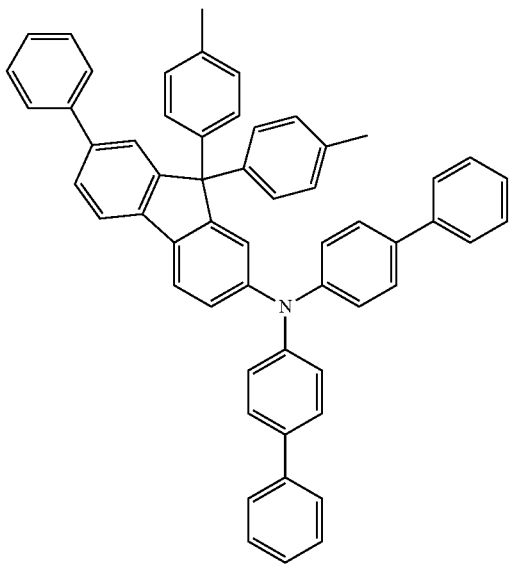
174
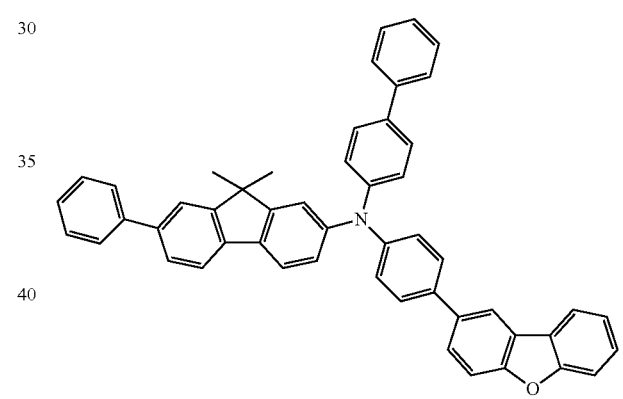
175
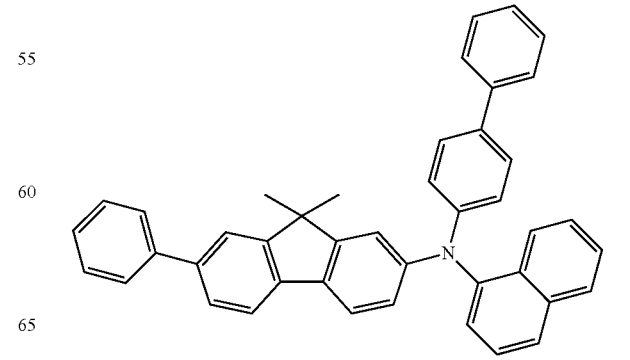

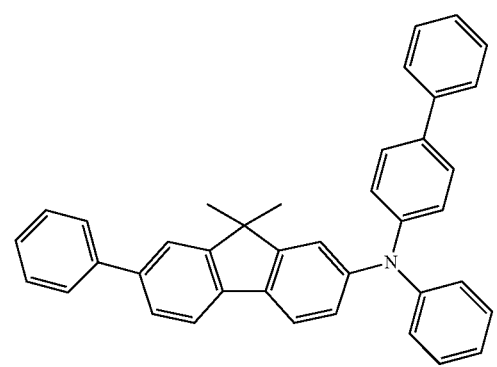
176
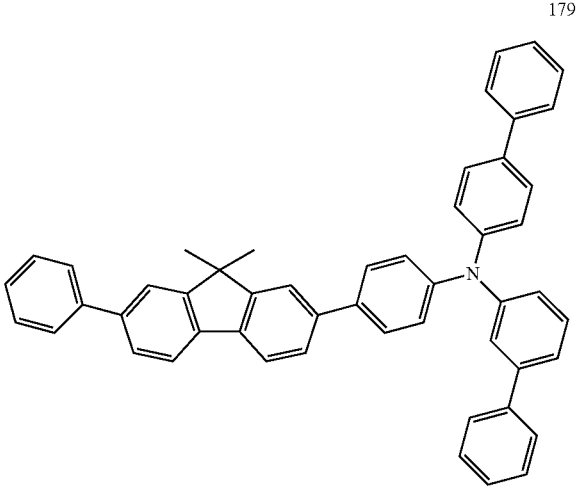
179
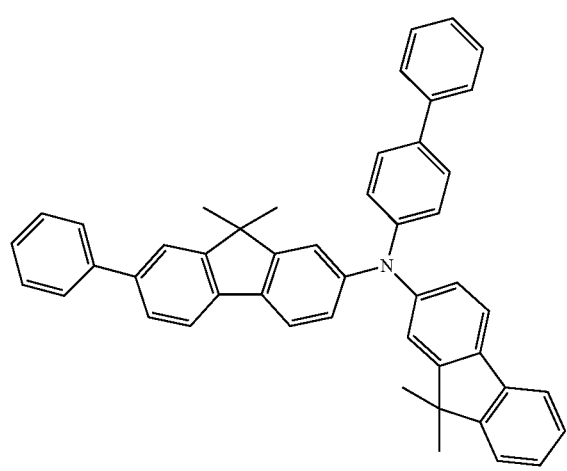
177
180
181
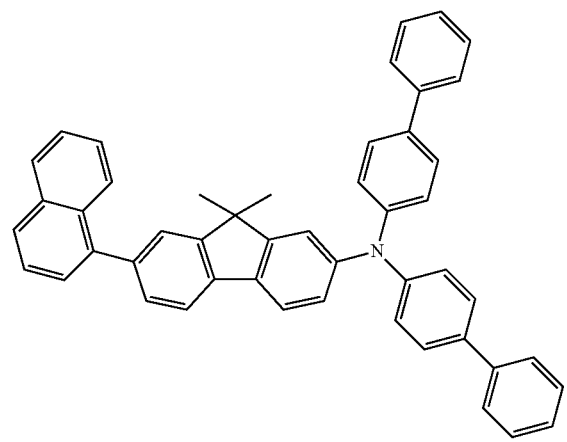
178
182

183
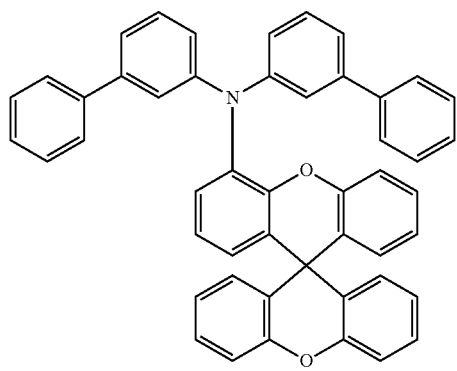
184
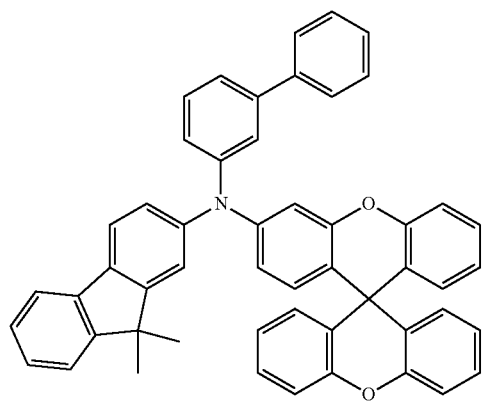
185
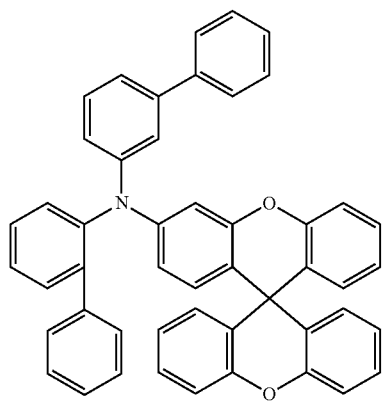
186
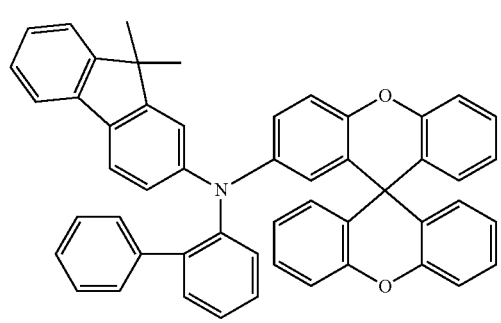
187
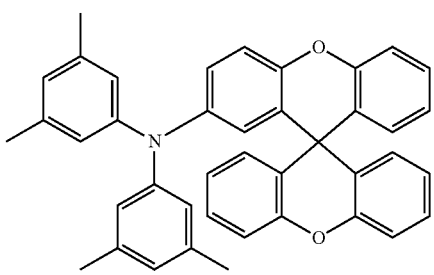
188
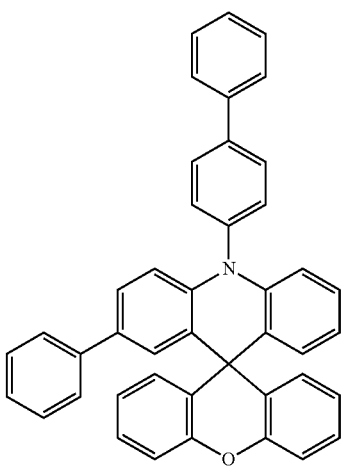
189
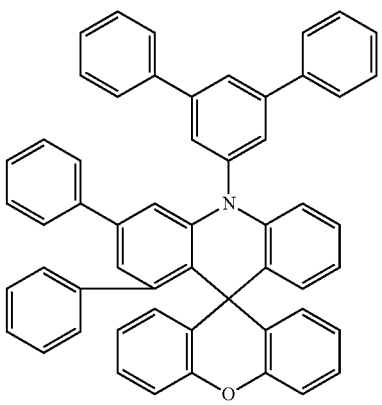
190
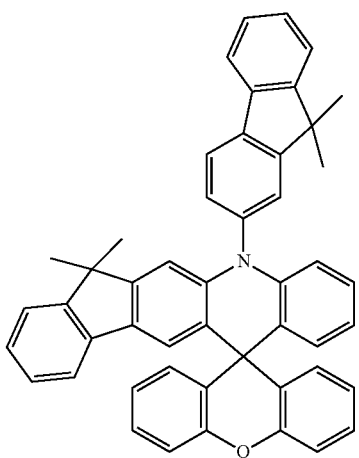

191 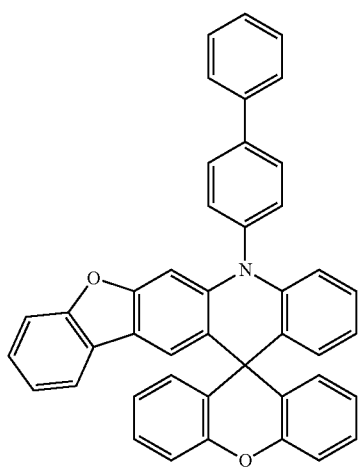
192 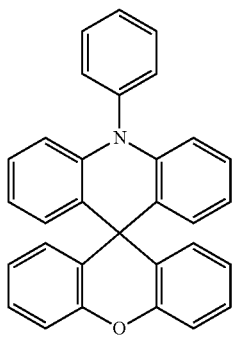
193 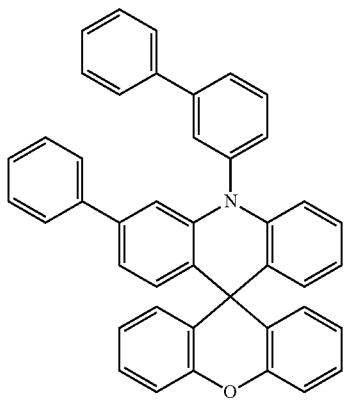
194 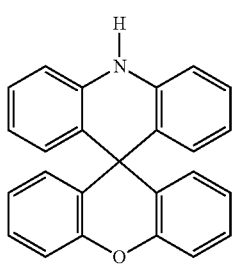
195 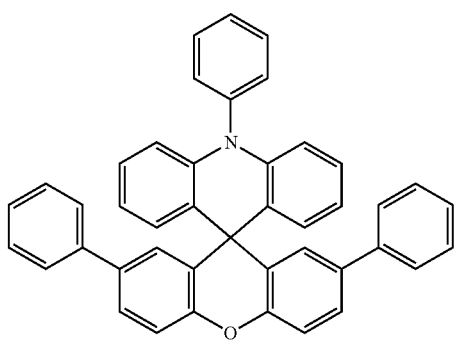
196 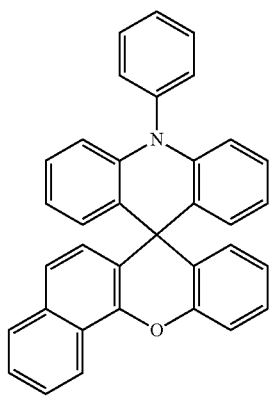
197 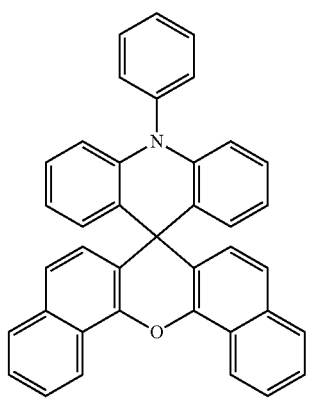
198 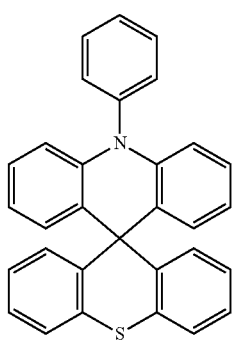

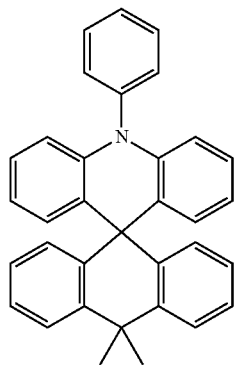
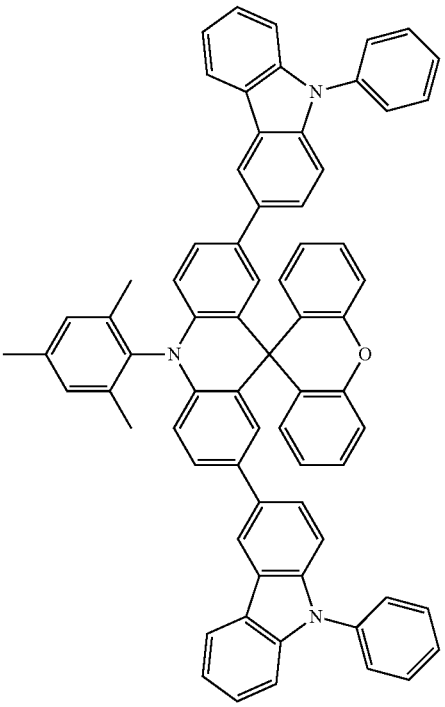
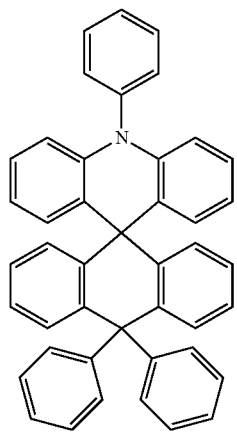
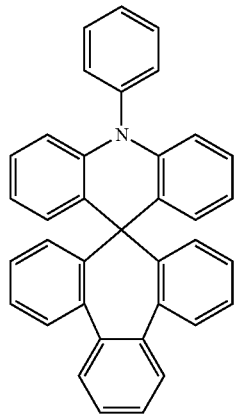
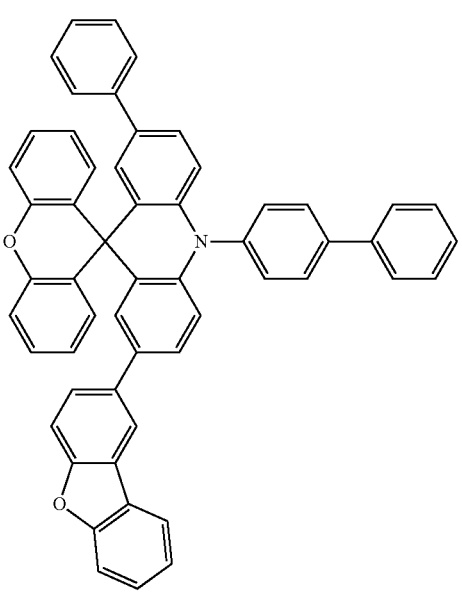
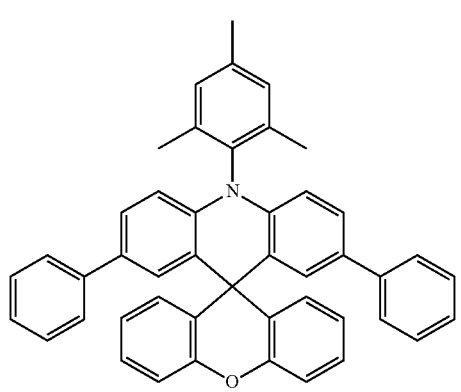

-continued
205
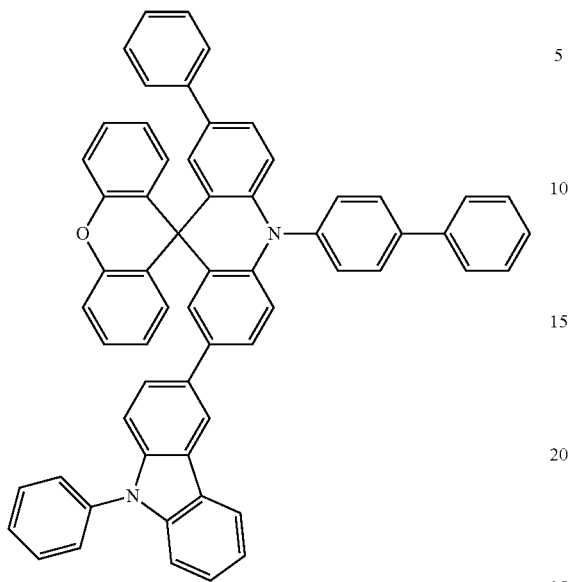
206
207
208
-continued
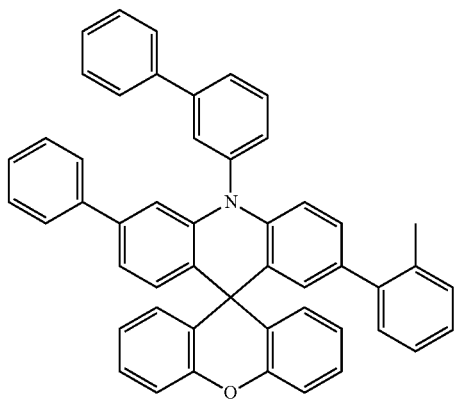
209
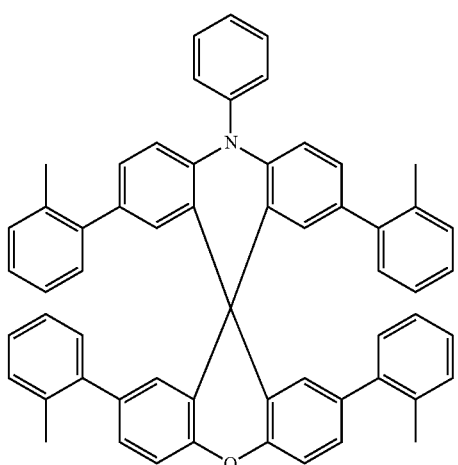
210
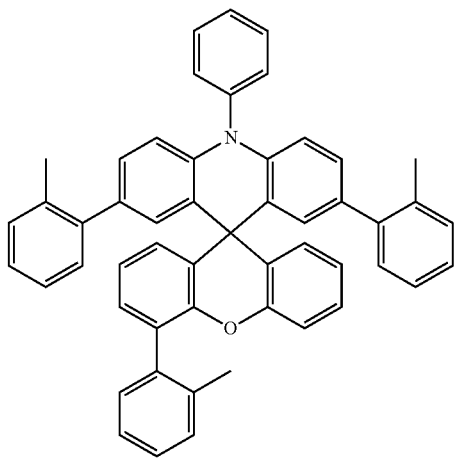

211 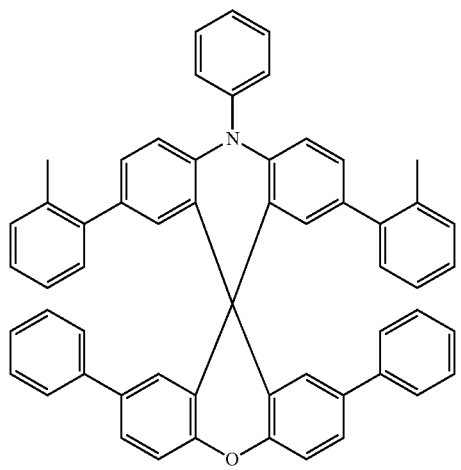
212 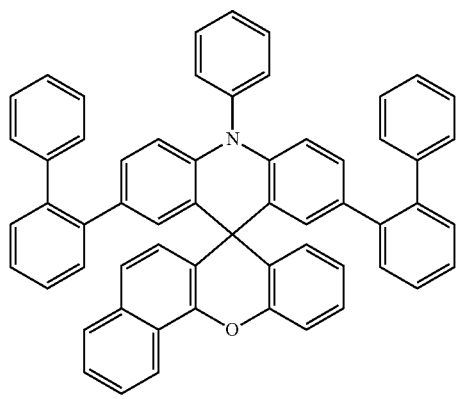
213 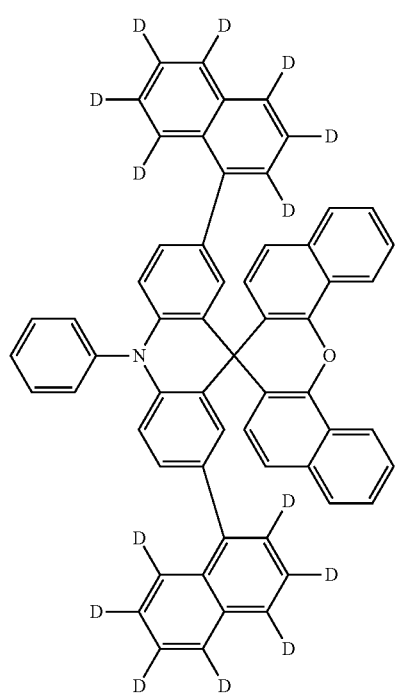
214 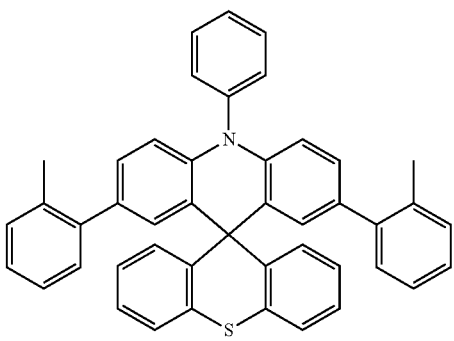
215 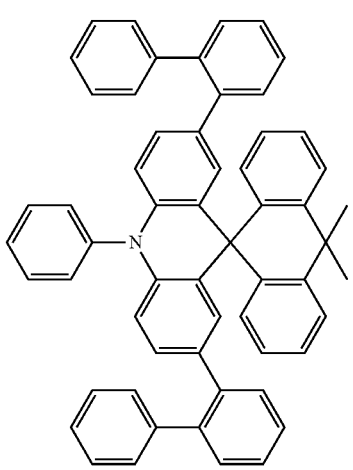
216 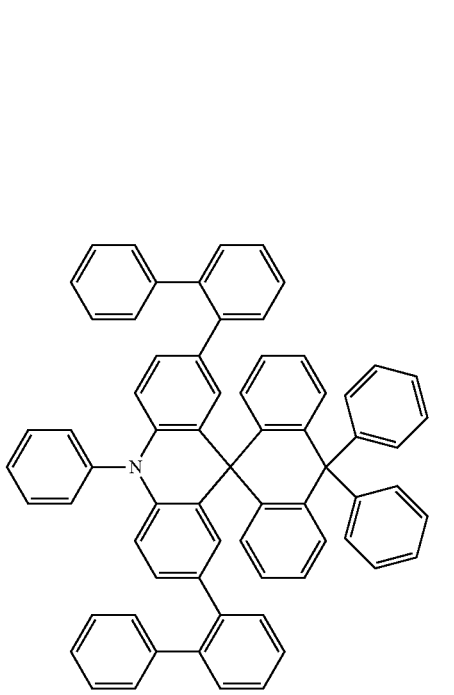

217
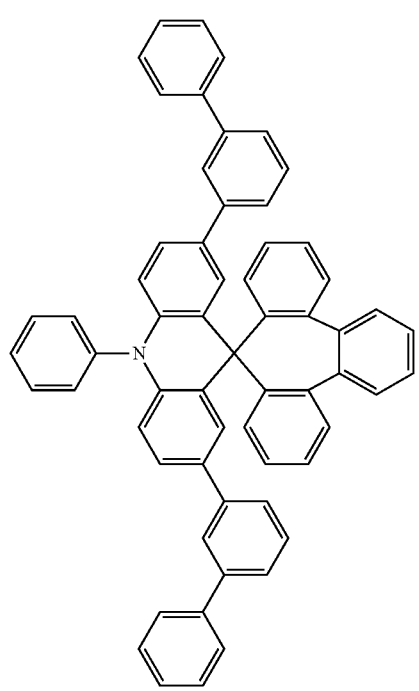
218
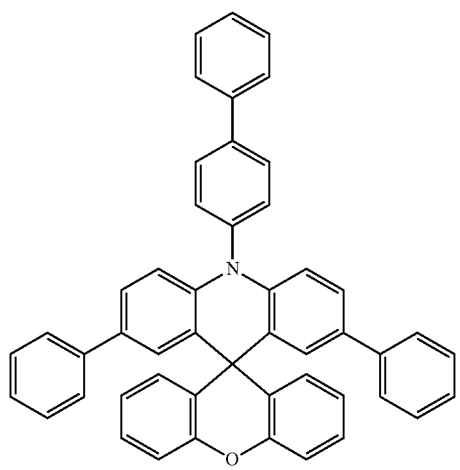
219
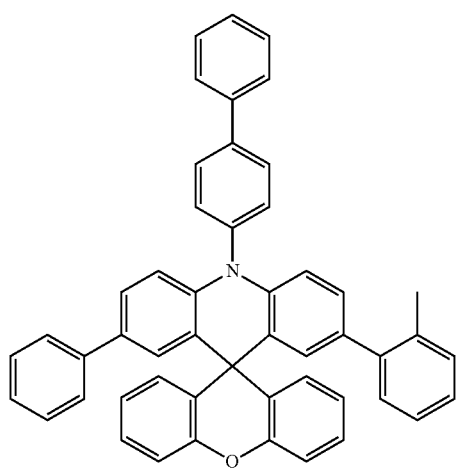
220
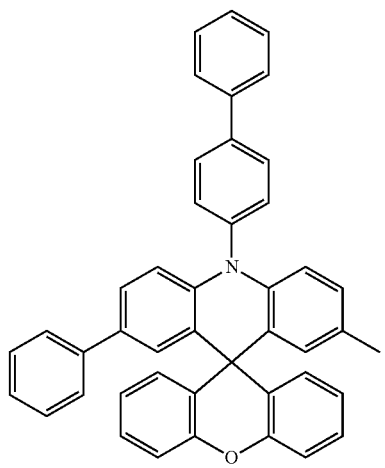
221
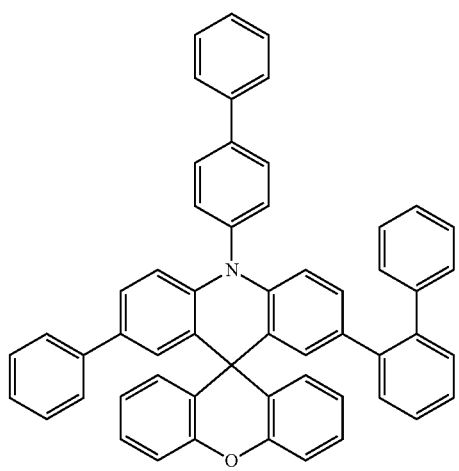
222
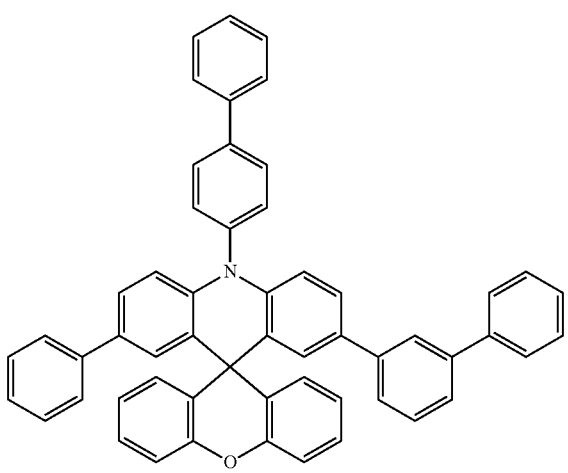

-continued
223
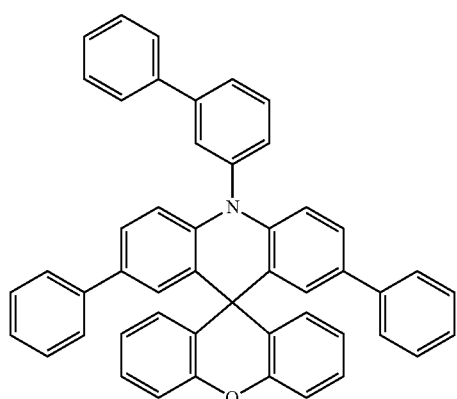
224
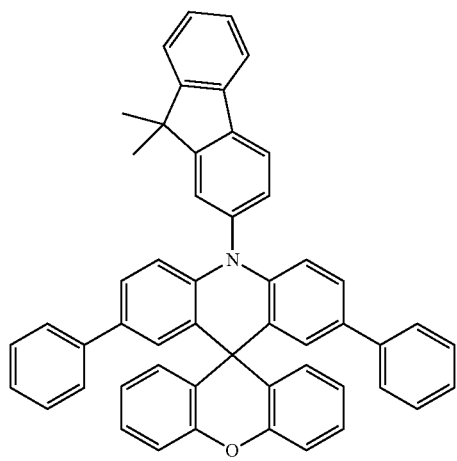
225
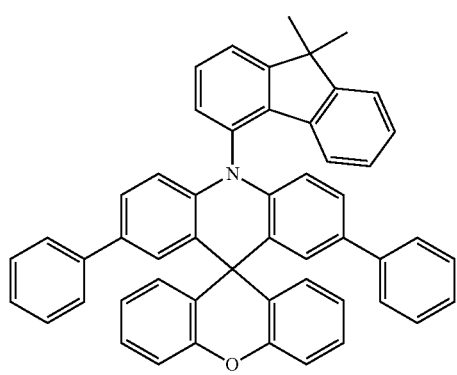
226
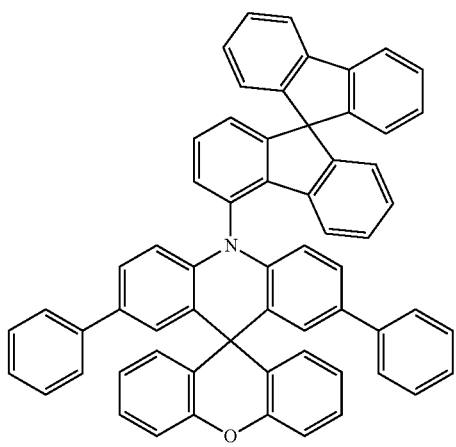
227
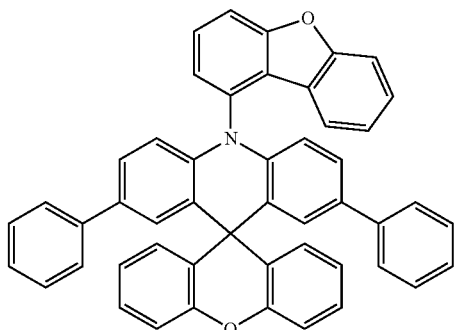
228
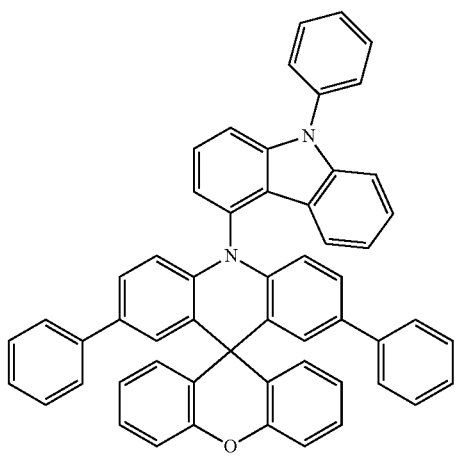

229
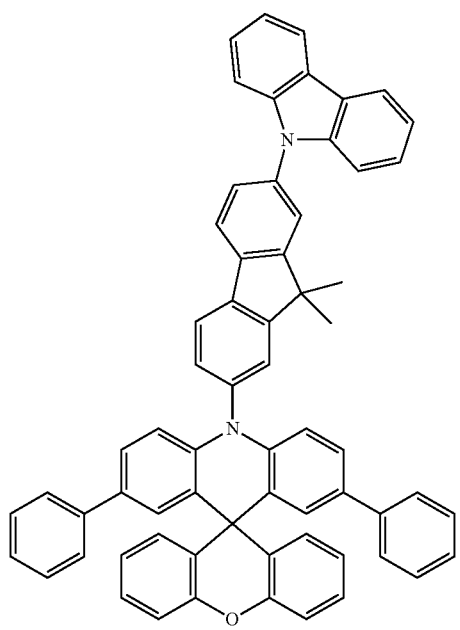
230
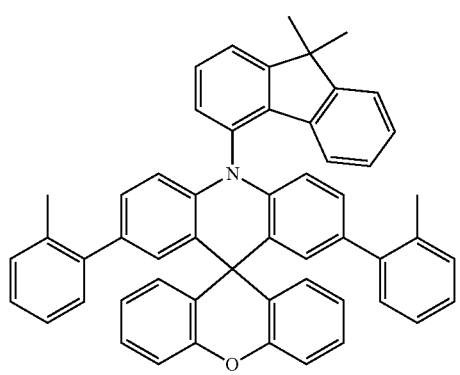
231
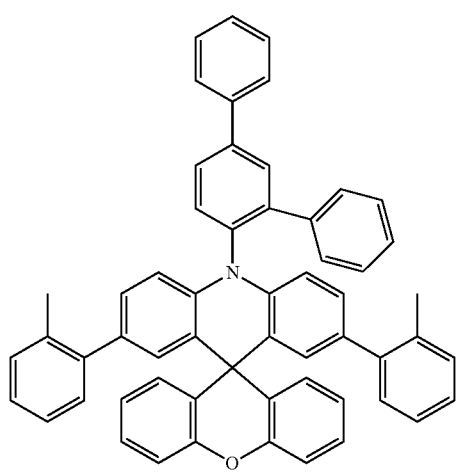
232
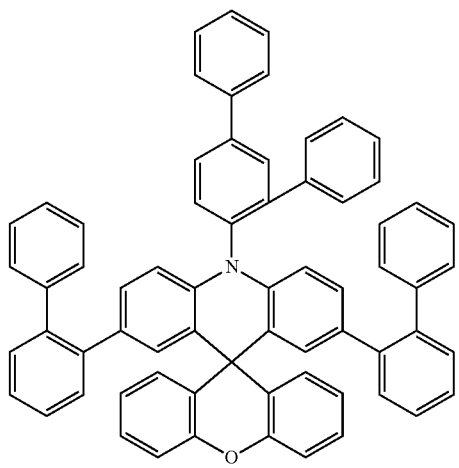
233
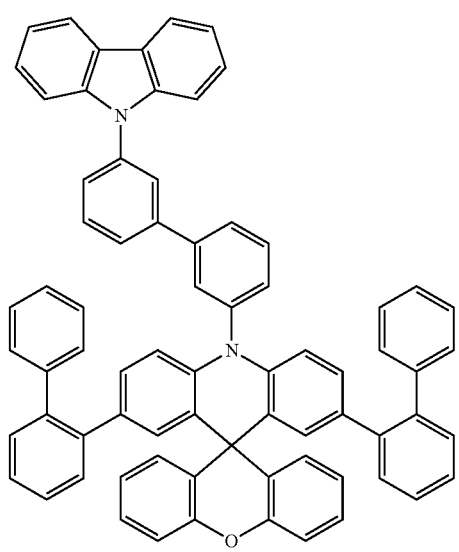
234
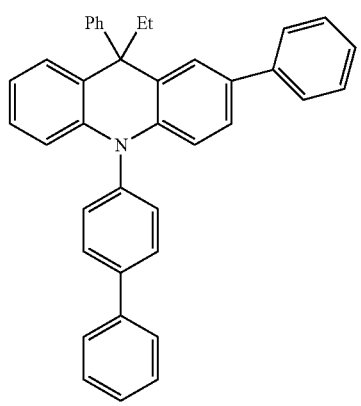

235 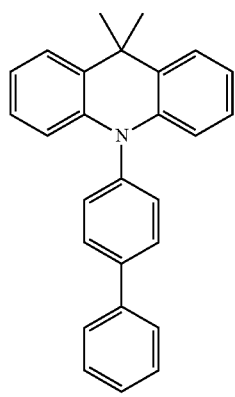
236 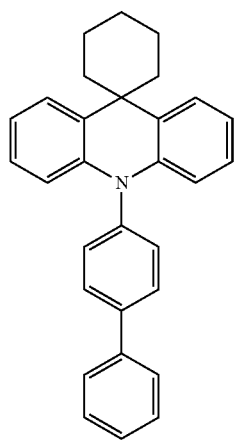
237 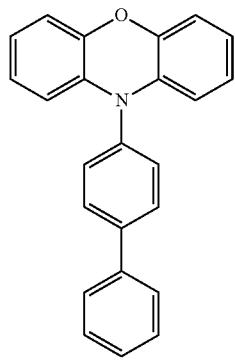
238 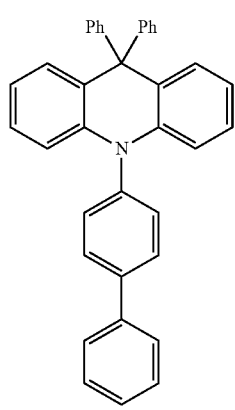
239 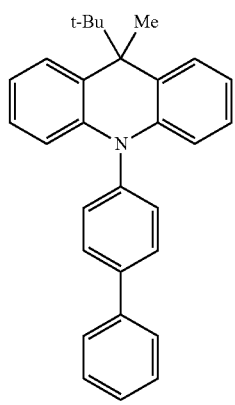
240 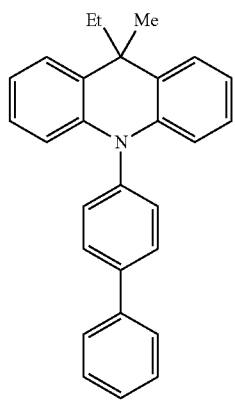
241 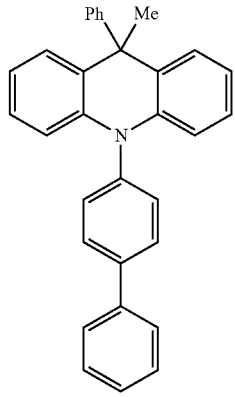
242 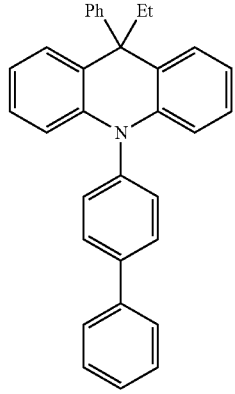

243
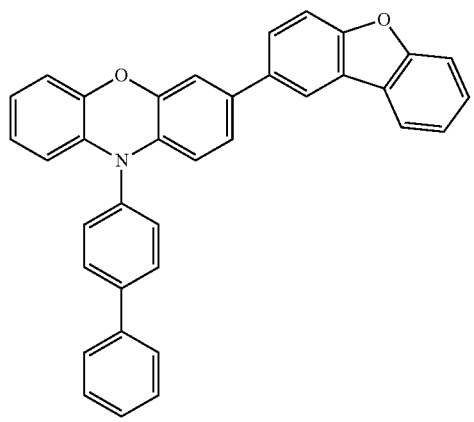
246
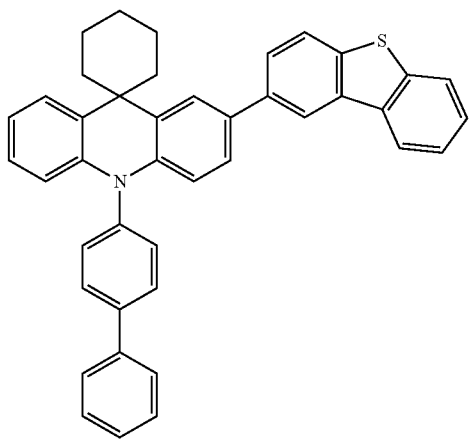
244
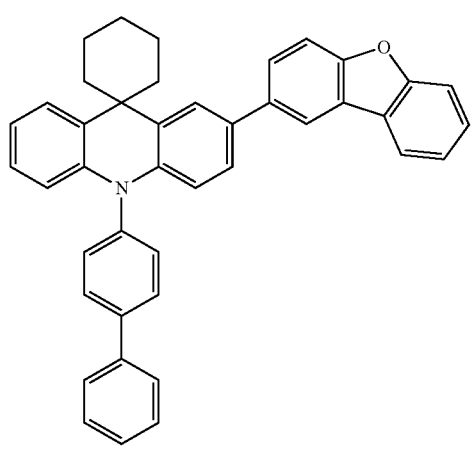
247
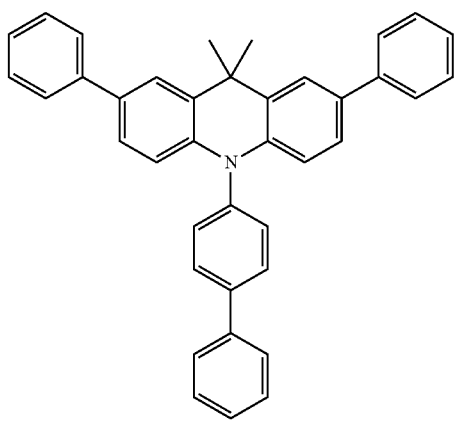
245
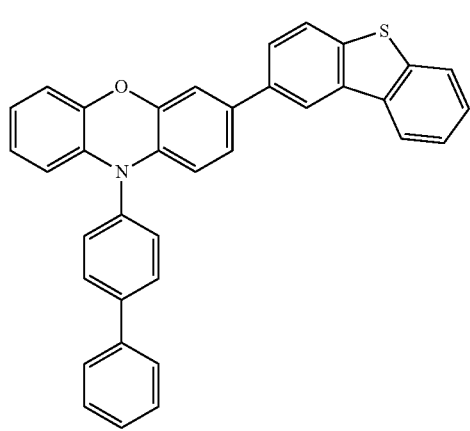
248
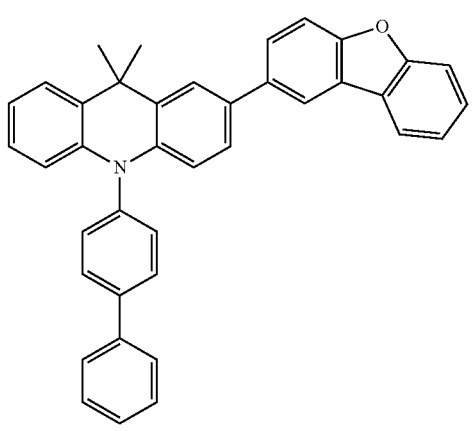

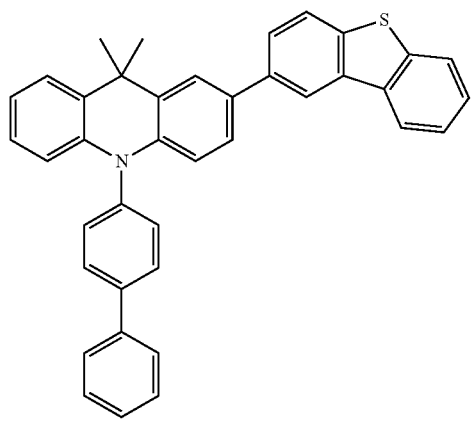
249
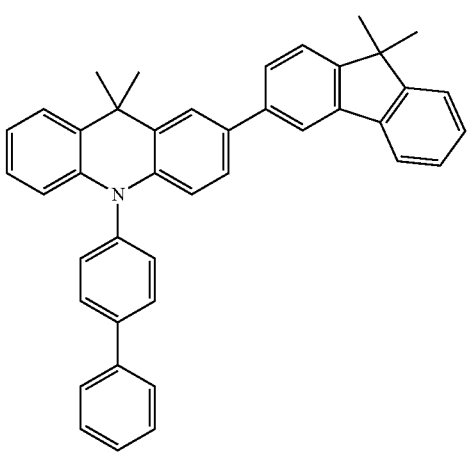
252
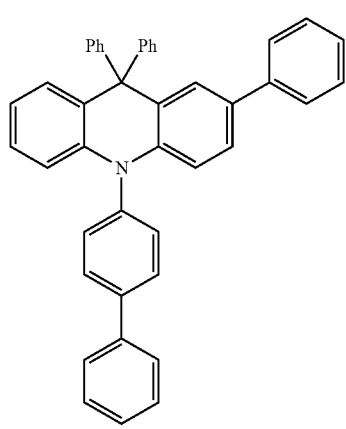
250
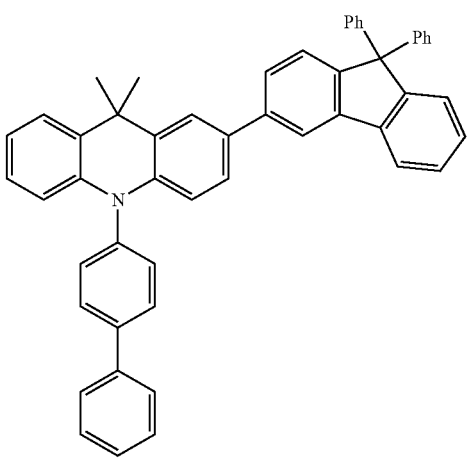
253
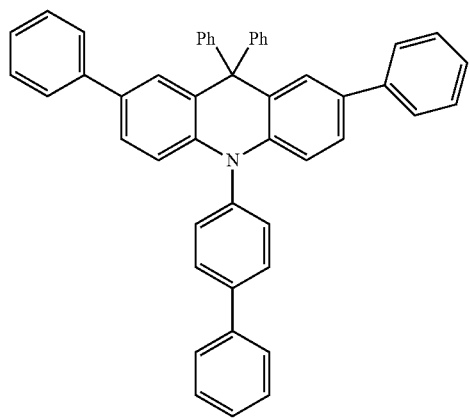
251
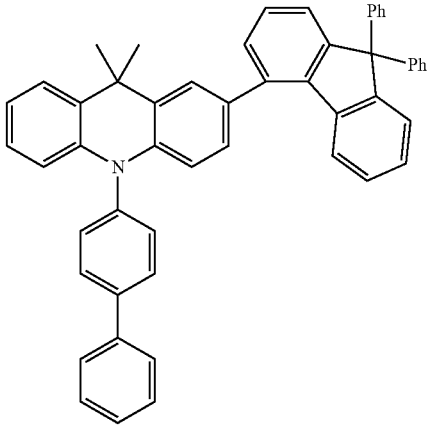
254

255
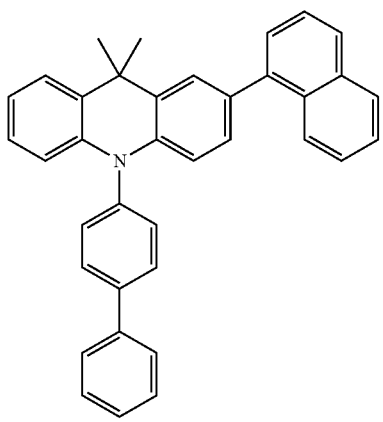
256
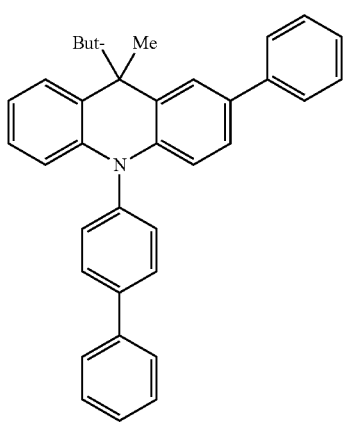
257
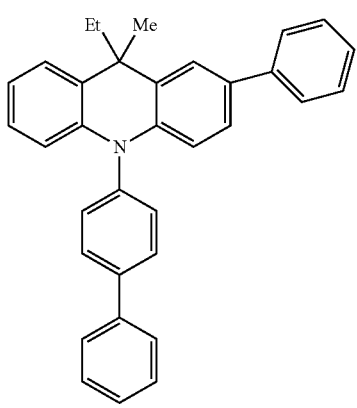
258
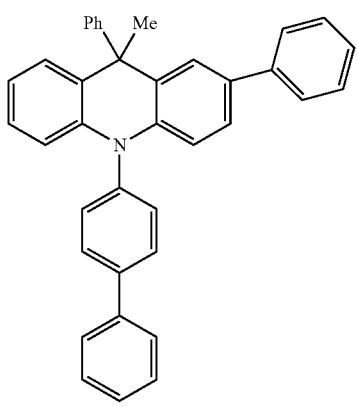
259
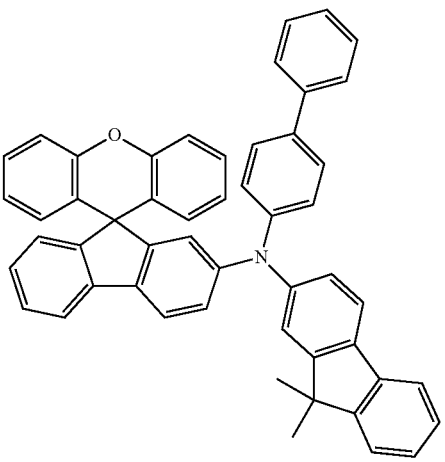
260
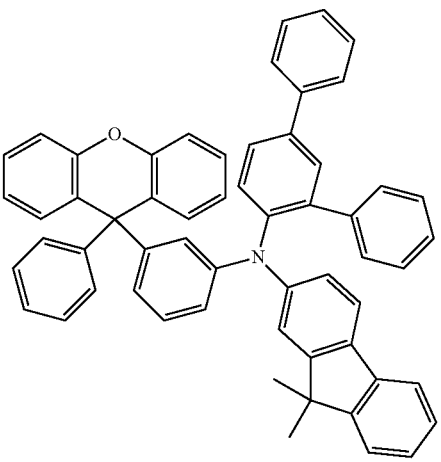
261

111
-continued
262
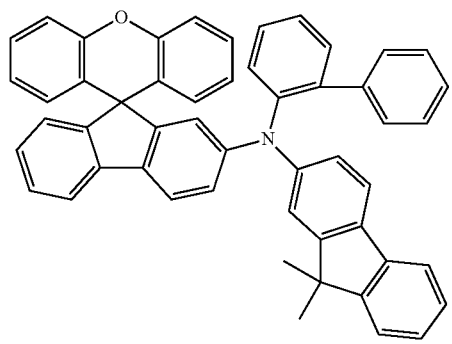
263
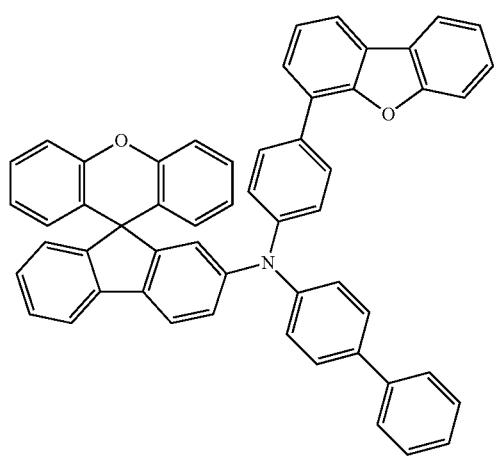
264
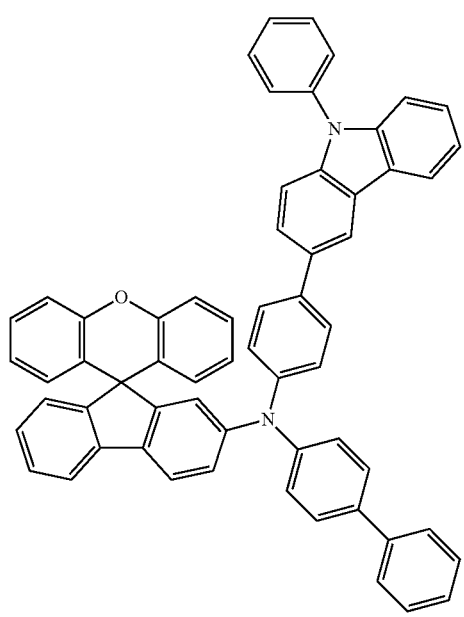
112
-continued
265
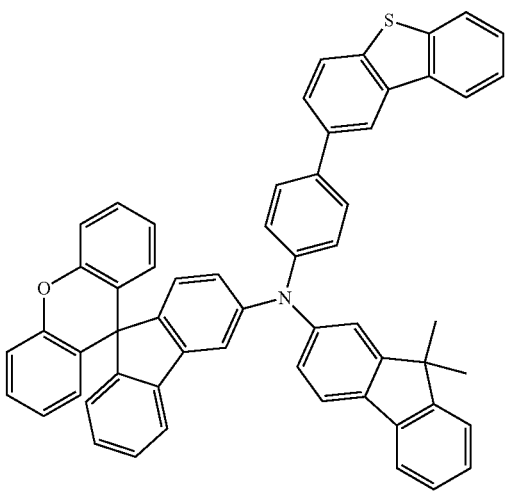
266
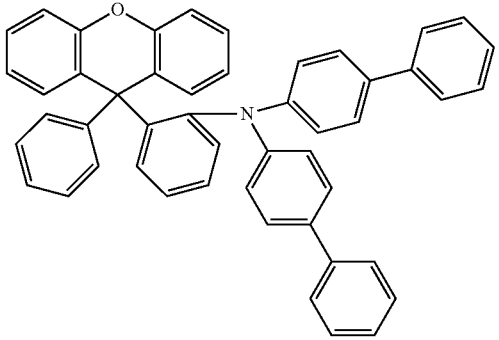
267
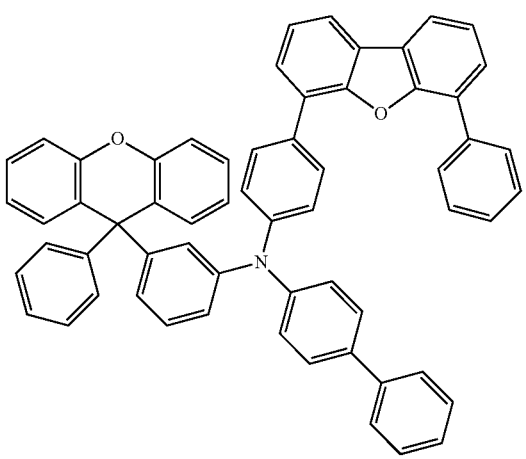

268 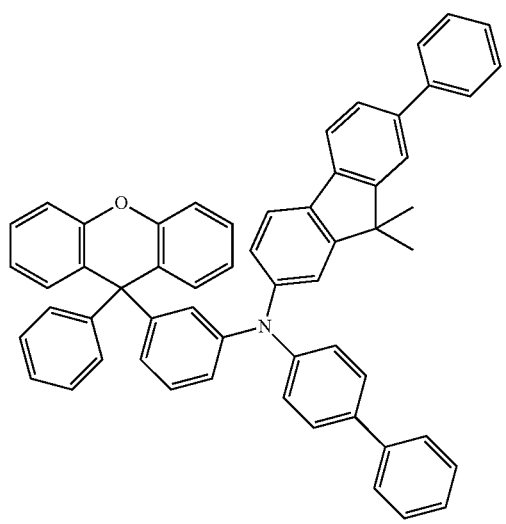
269 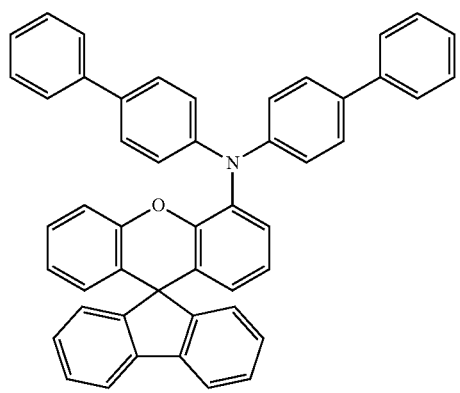
270 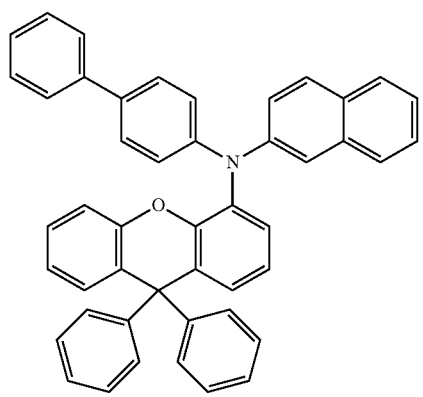
271 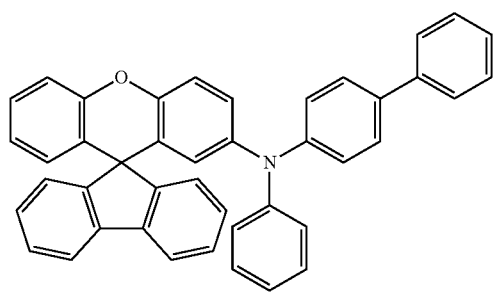
272 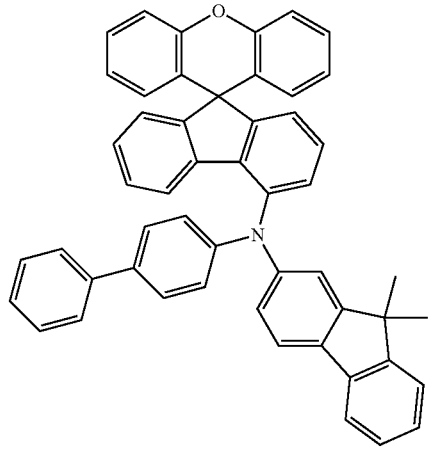
273 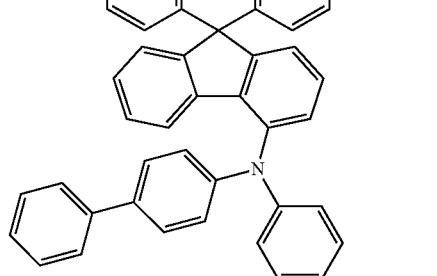
274 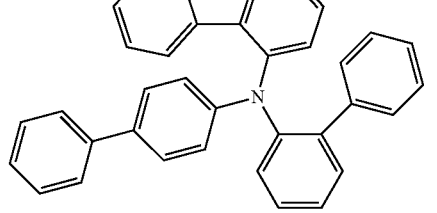

275
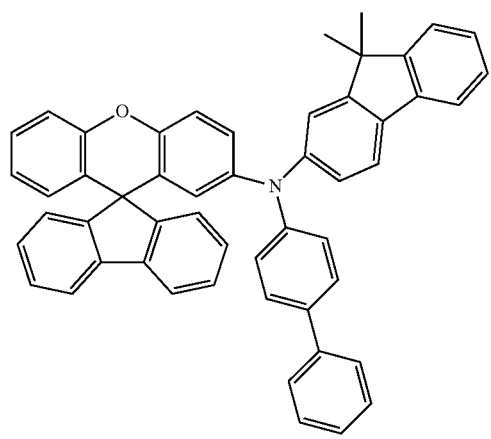
276
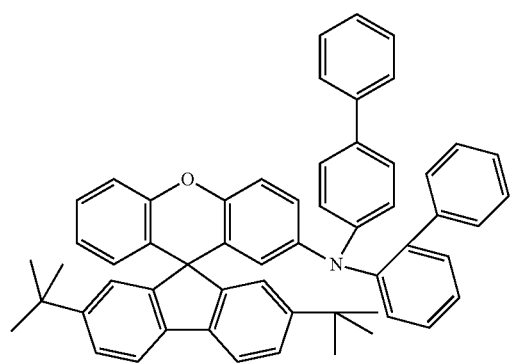
277
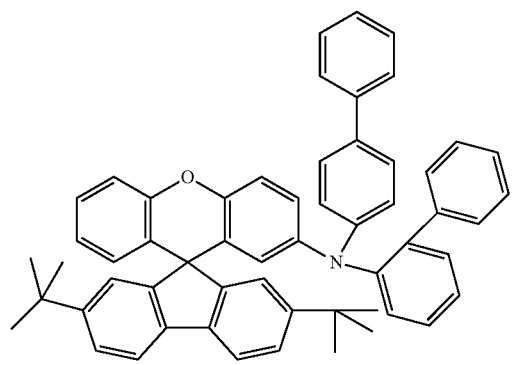
278
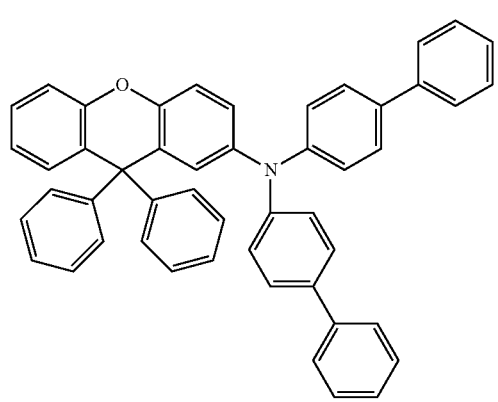
279
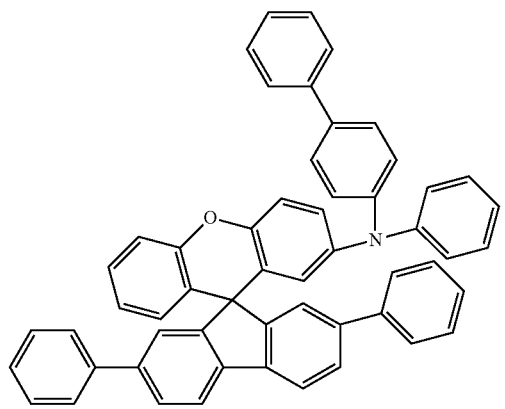
280
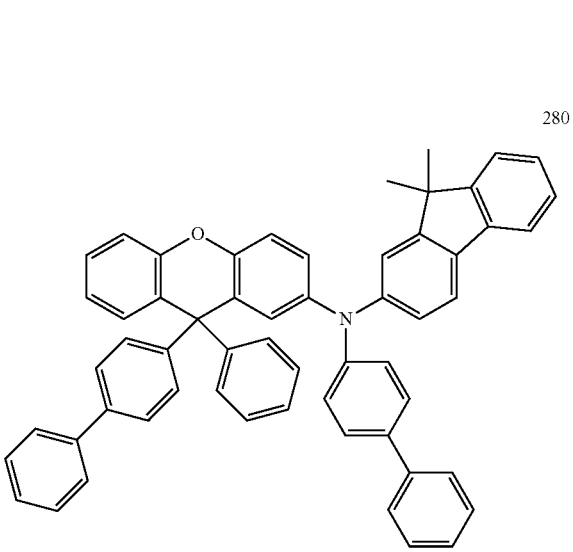
281
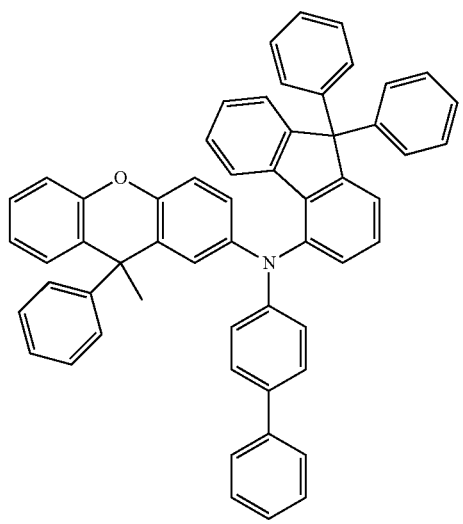

282
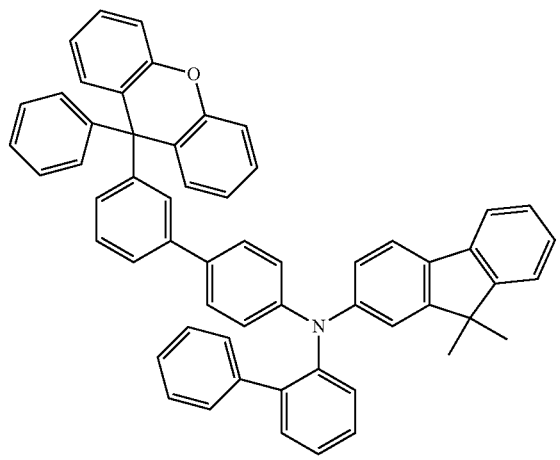
283
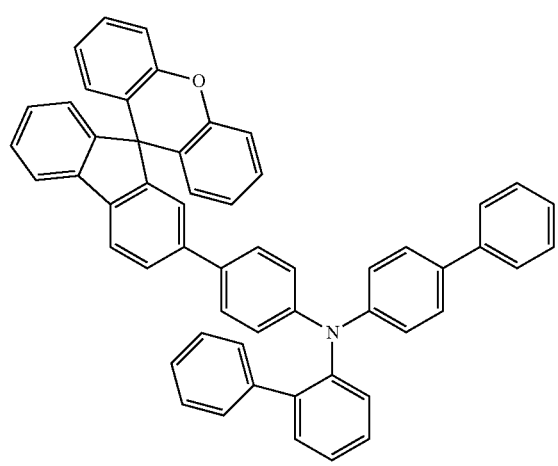
284
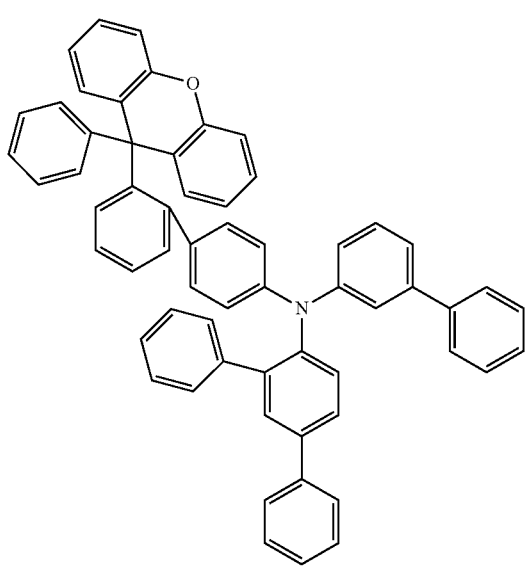
285
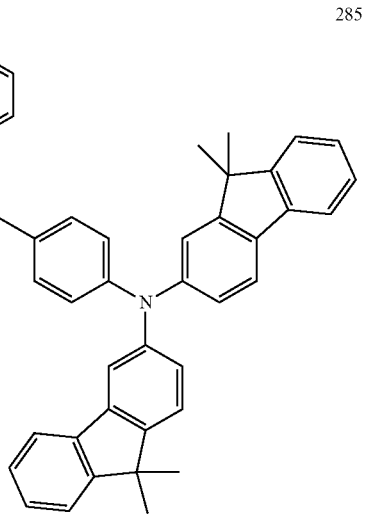
286
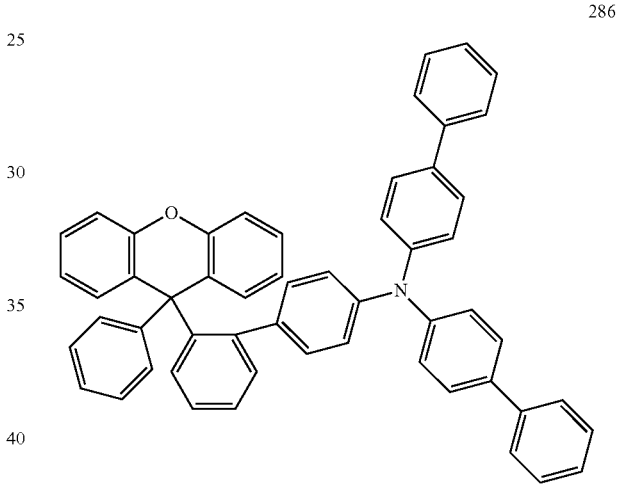
287
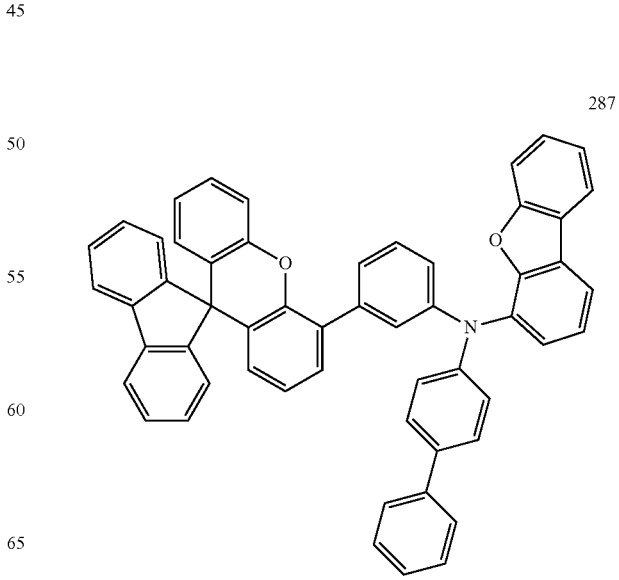

288
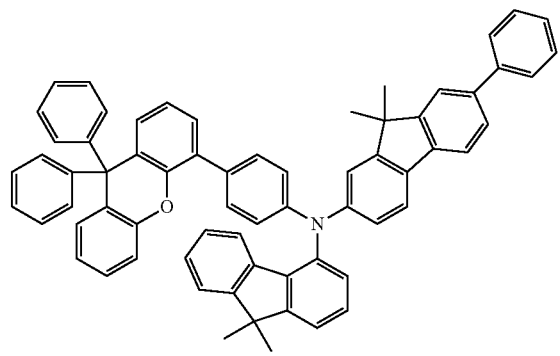
289
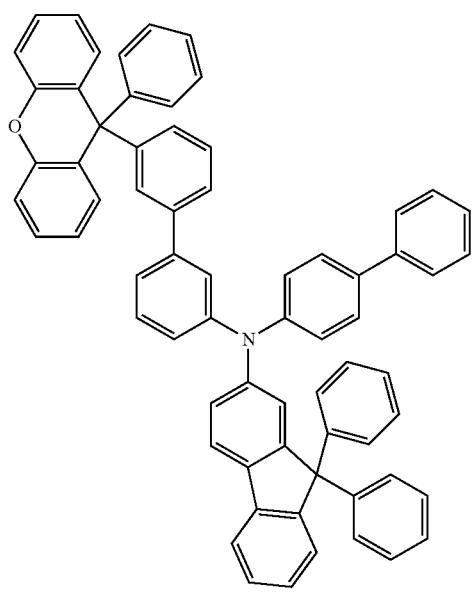
290
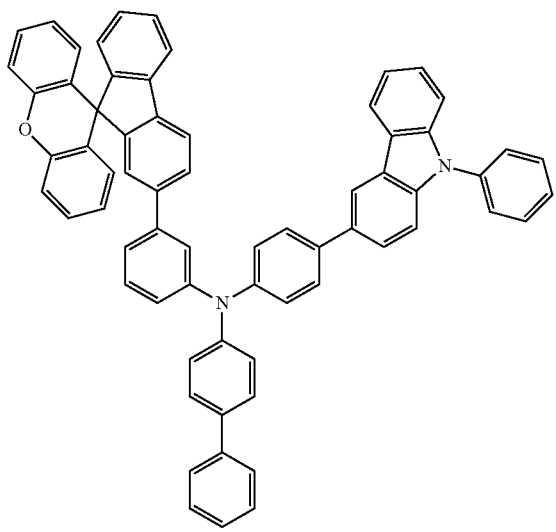
291
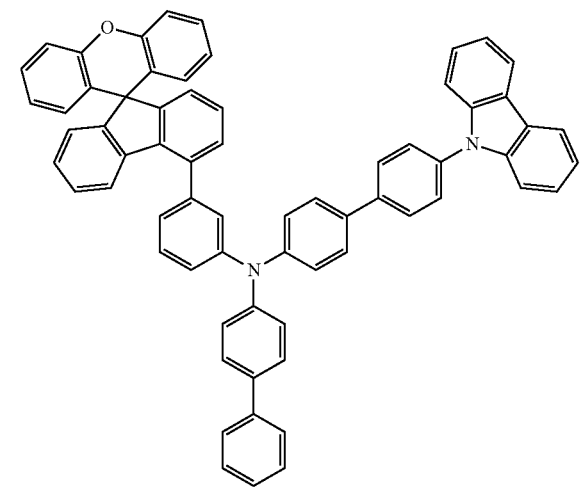
292
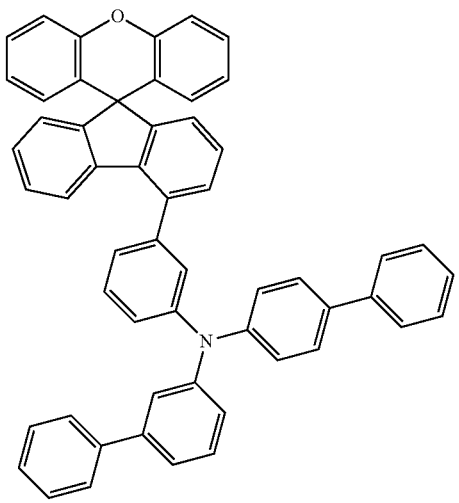
293
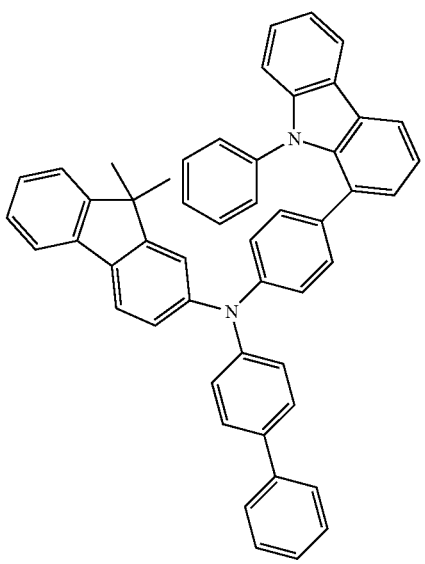

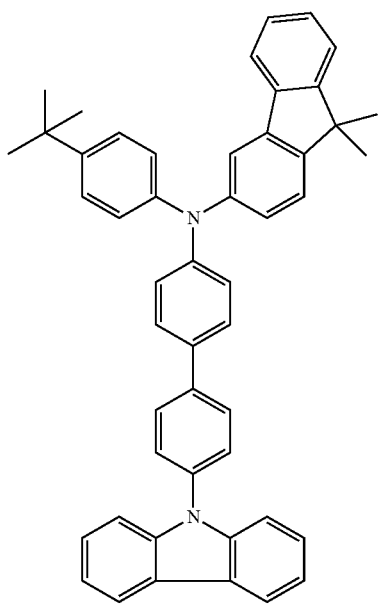
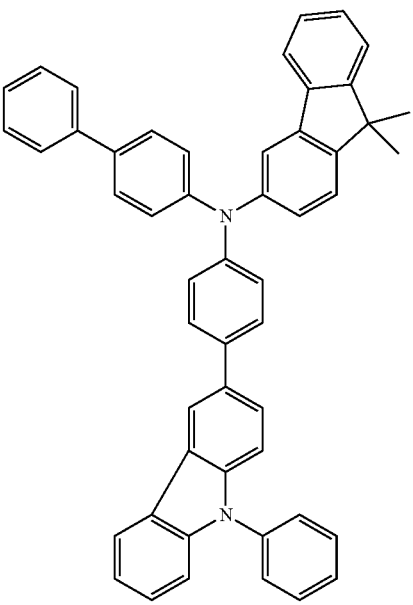
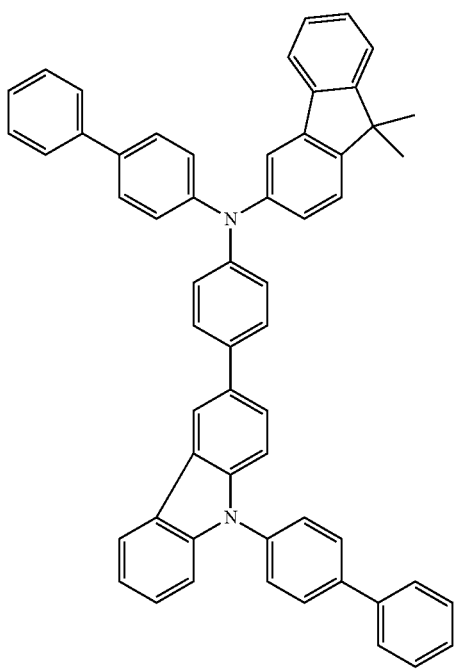
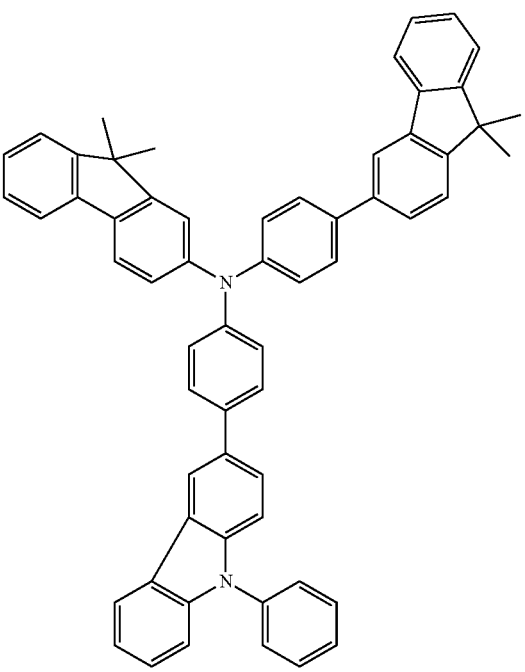

123
-continued
298
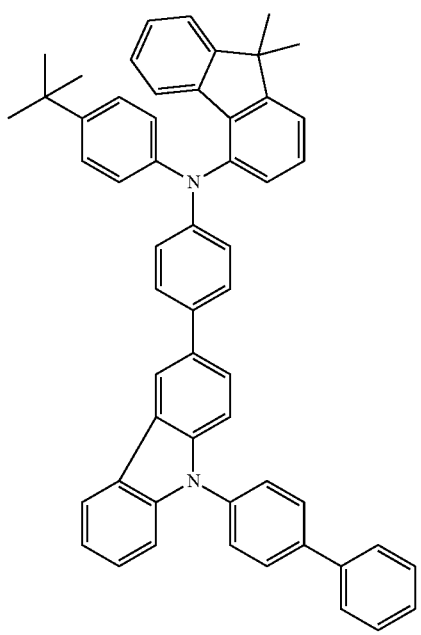
299
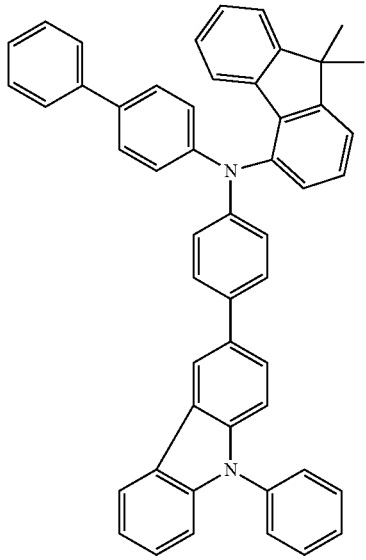
124
-continued
300
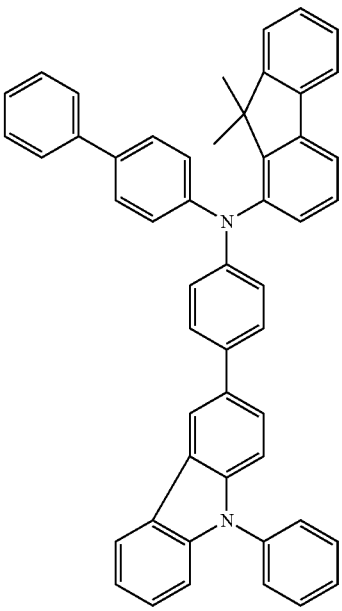
301
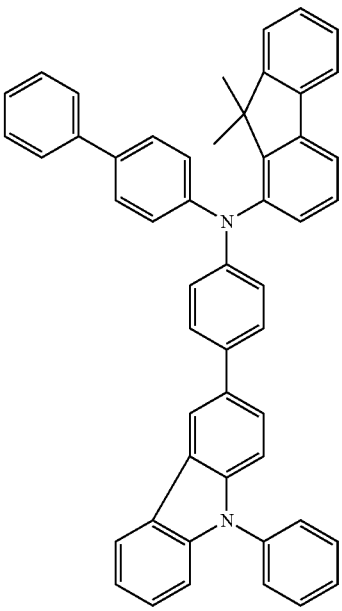

125
-continued
302
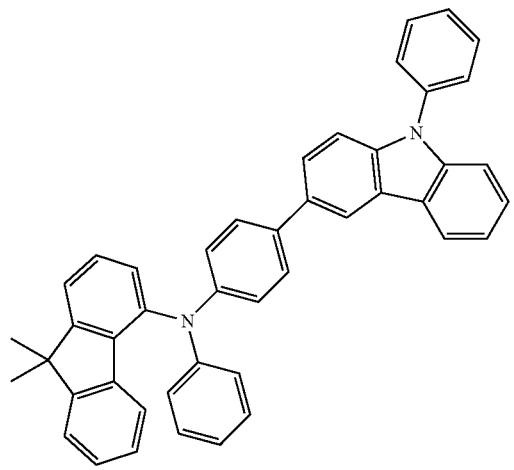
303
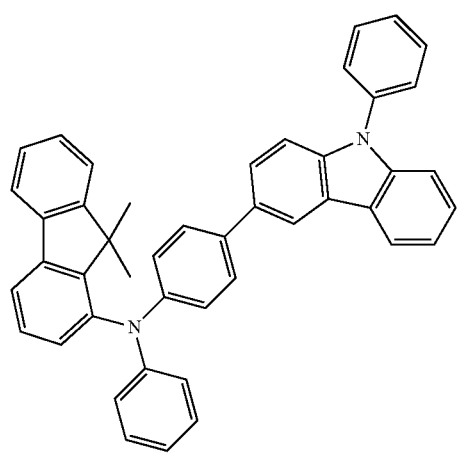
304
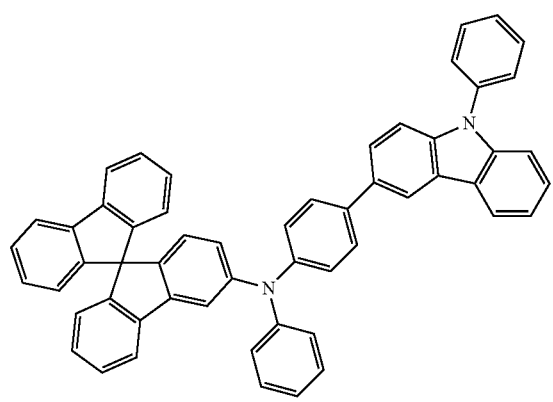
126
-continued
305
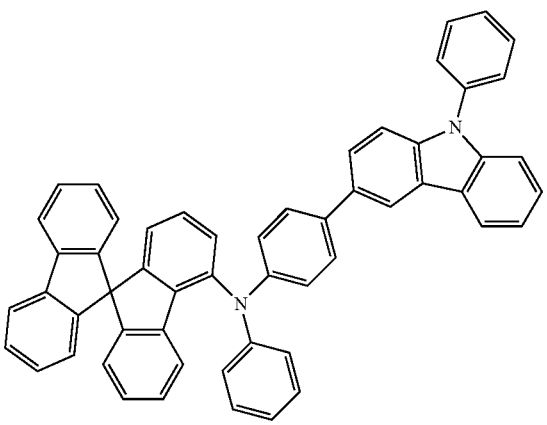
306
307
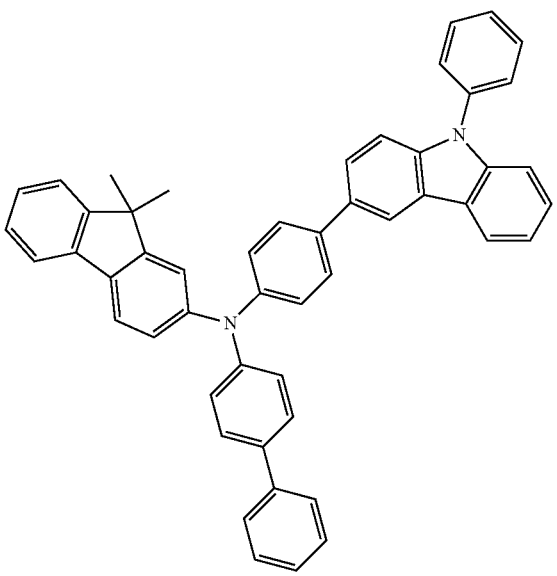

308
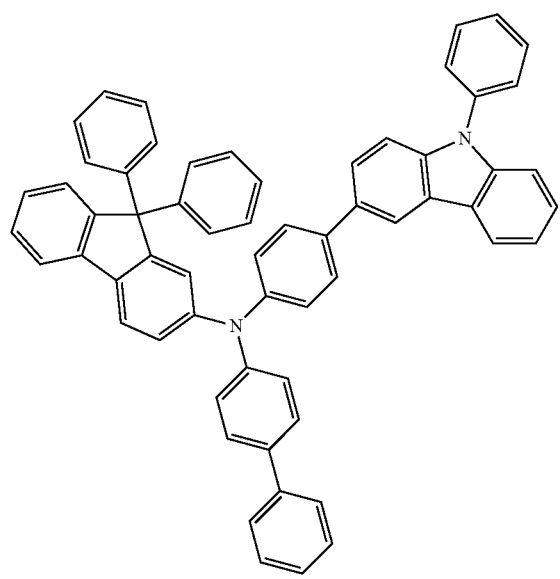
309
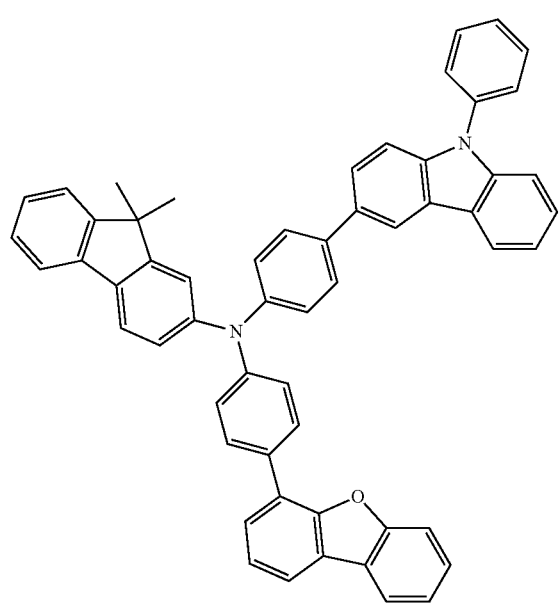
310
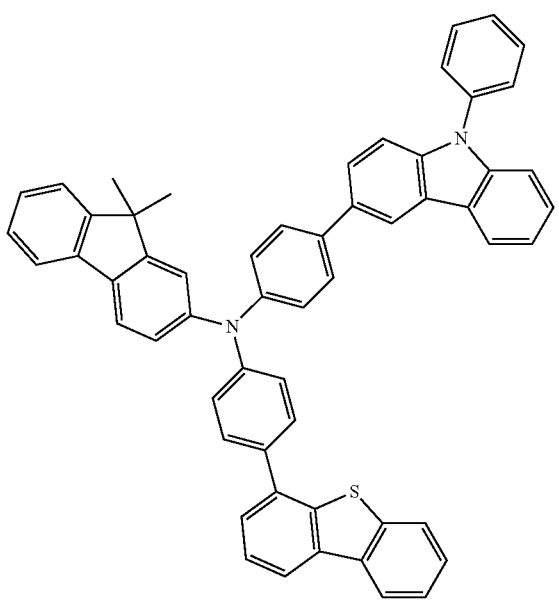
311
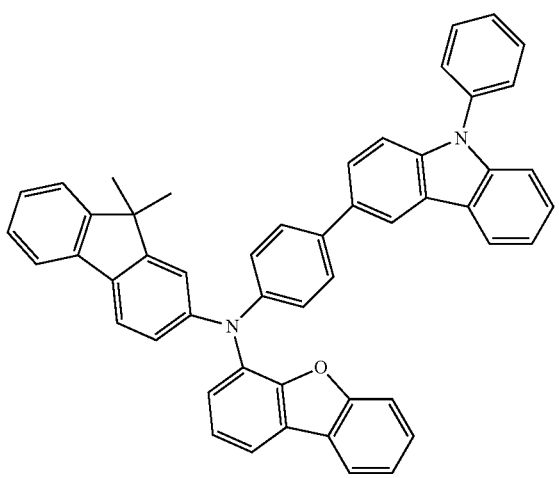
312

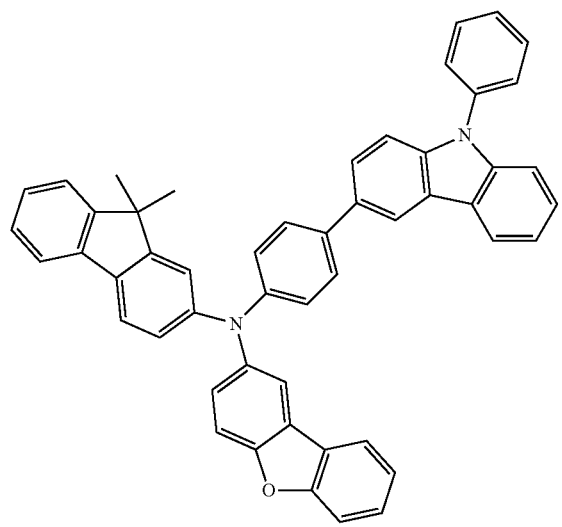
313
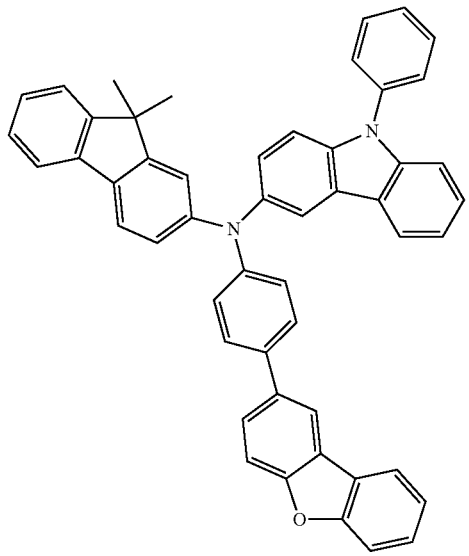
315
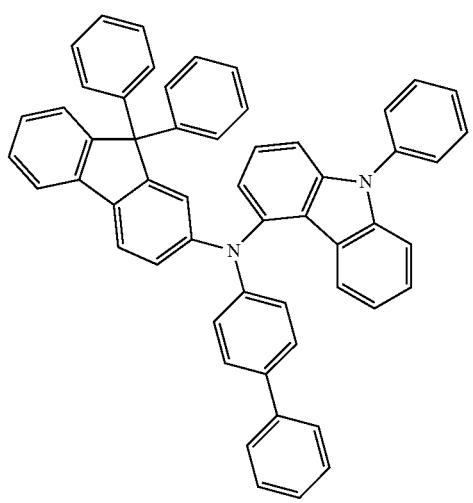
316
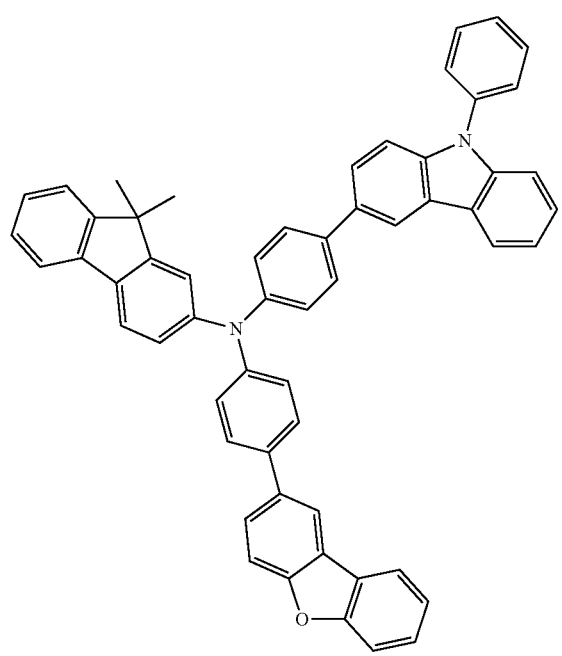
314
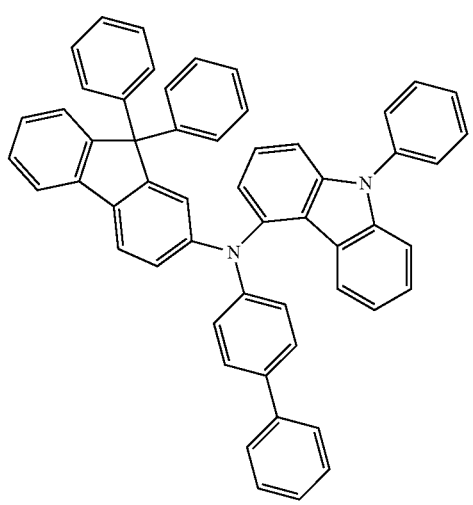
317

318
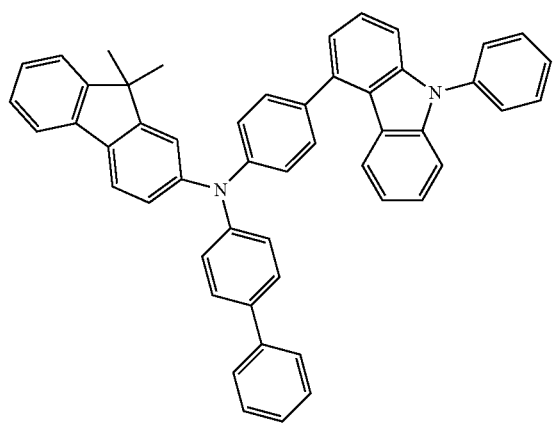
319
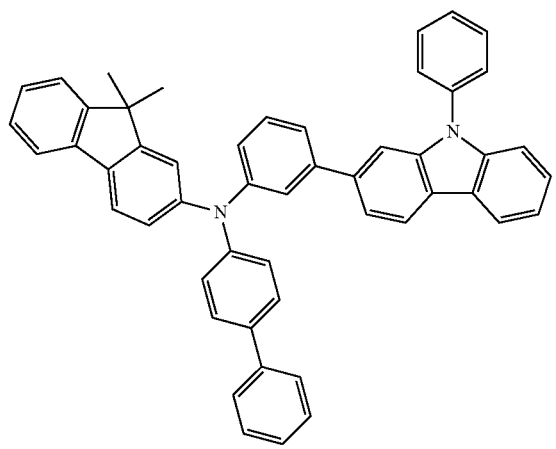
320
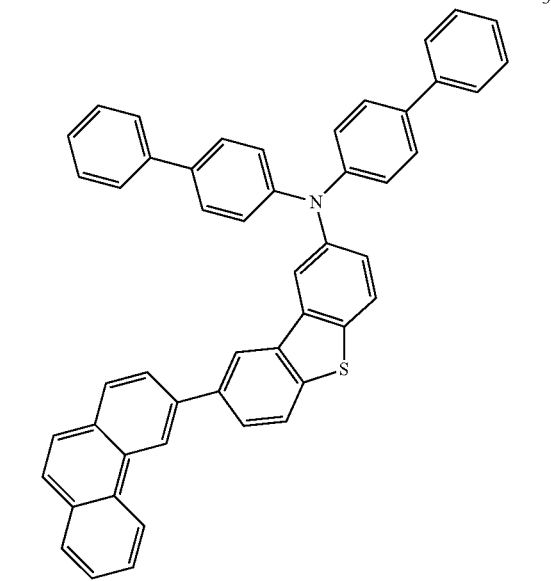
321
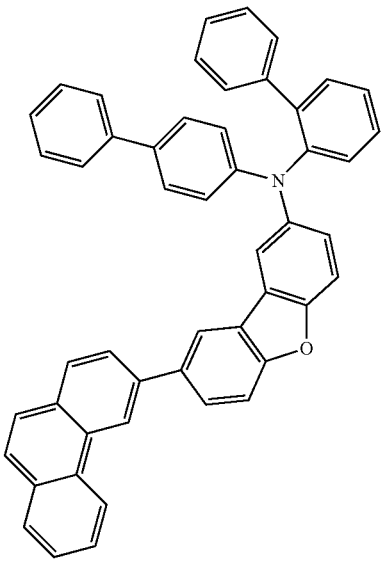
322
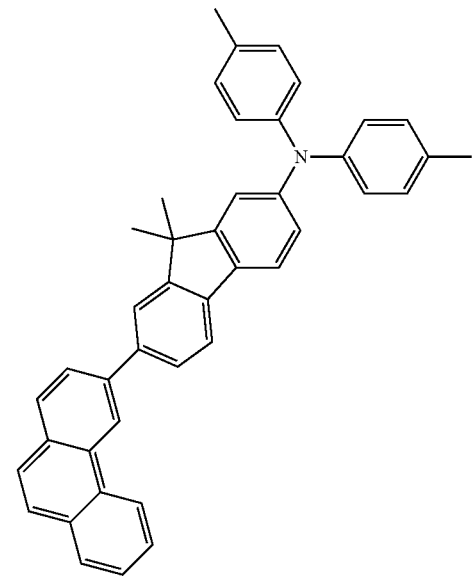
323
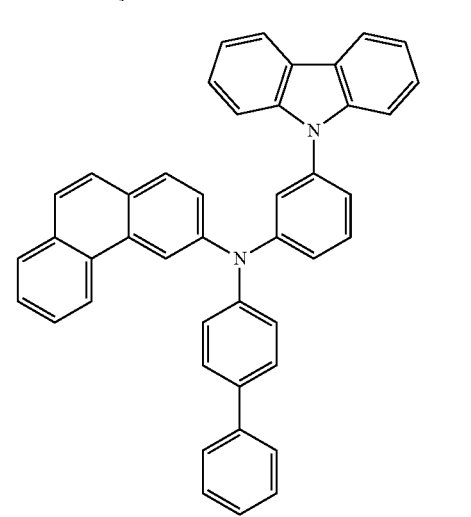

324
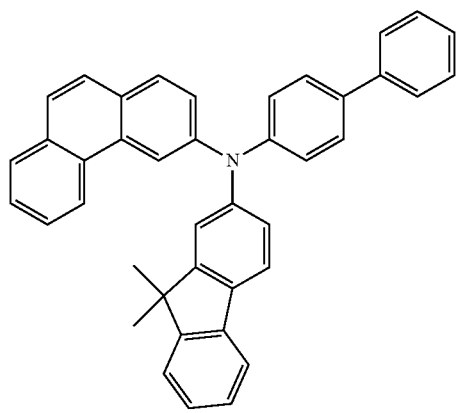
325
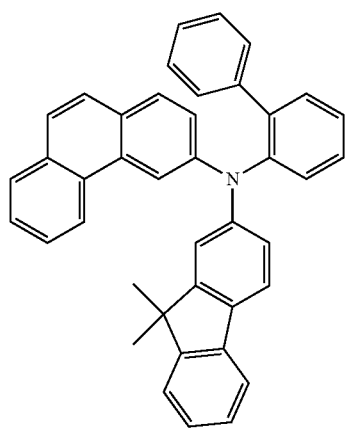
326
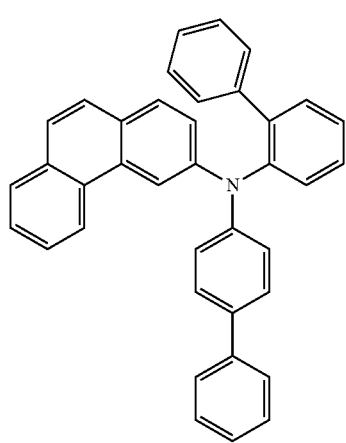
327
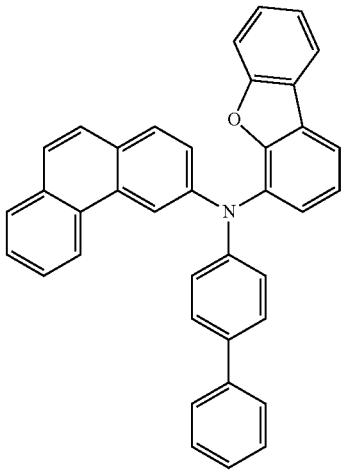
328
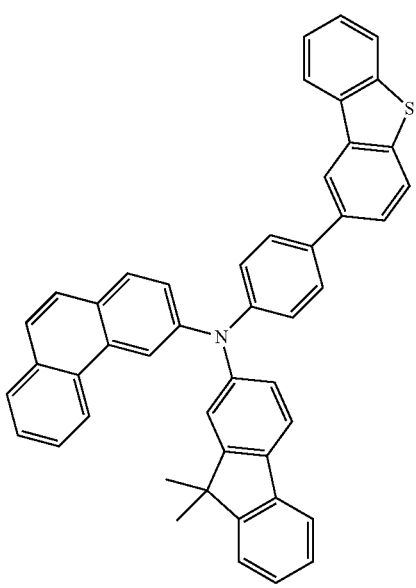
329
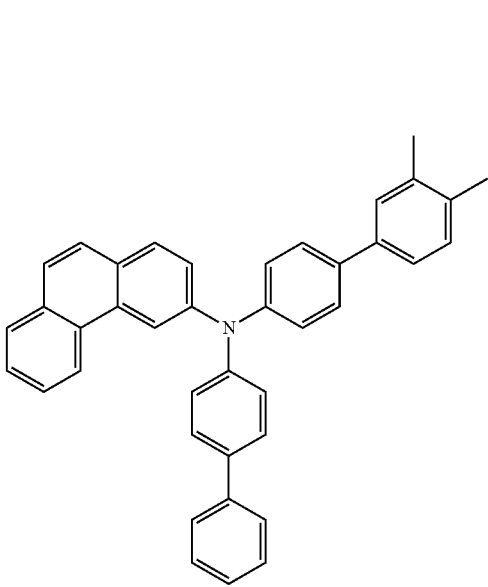

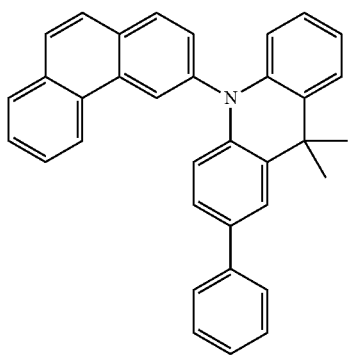
330
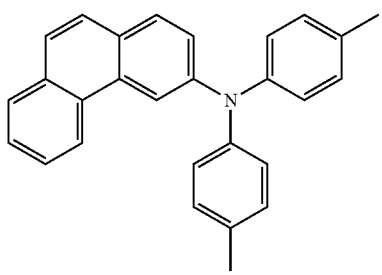
331
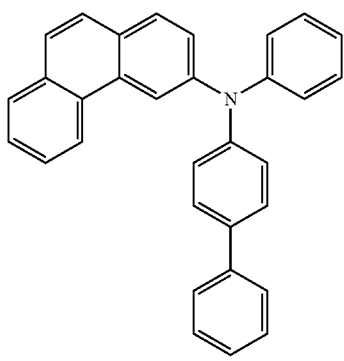
332
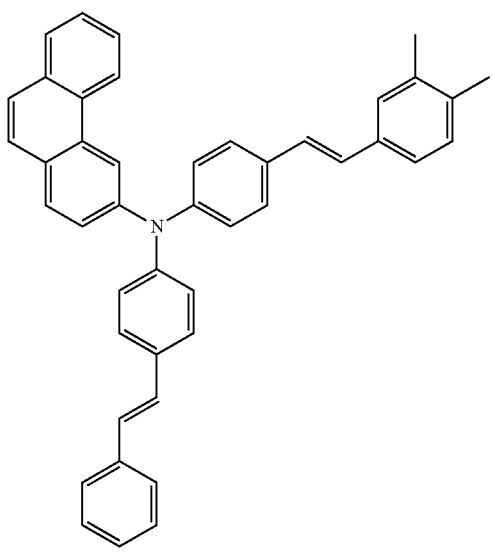
333
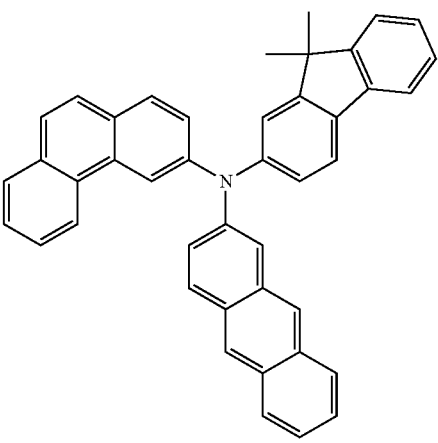
334
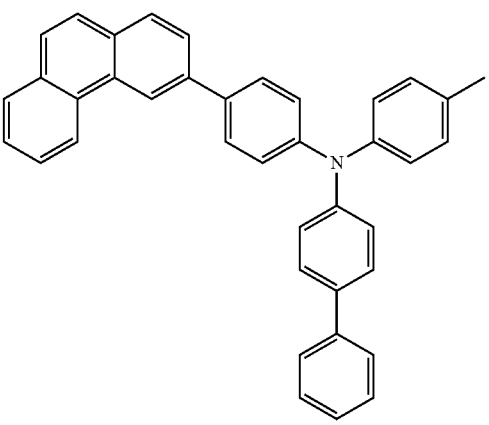
335
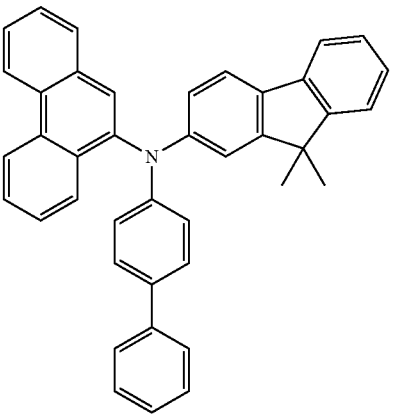
336

337
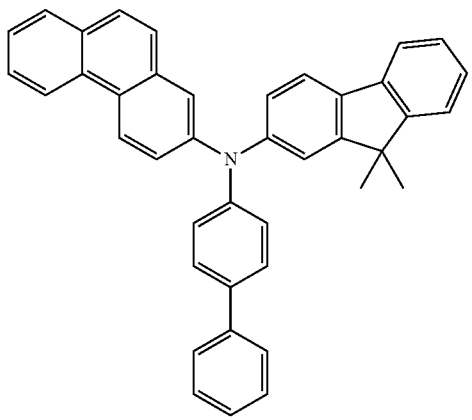
338
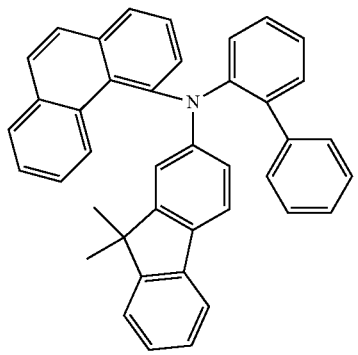
339
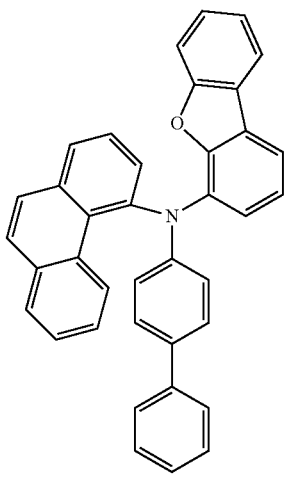
340
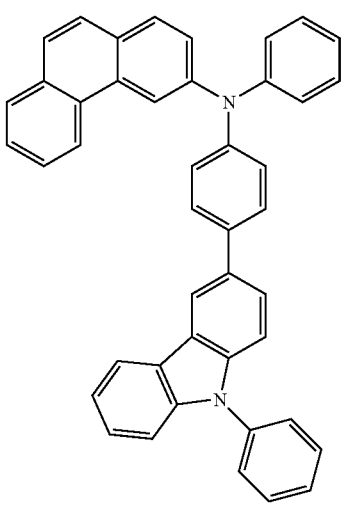
341
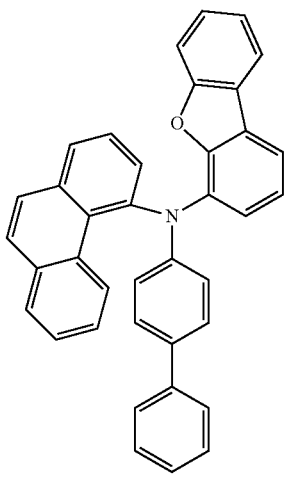
342
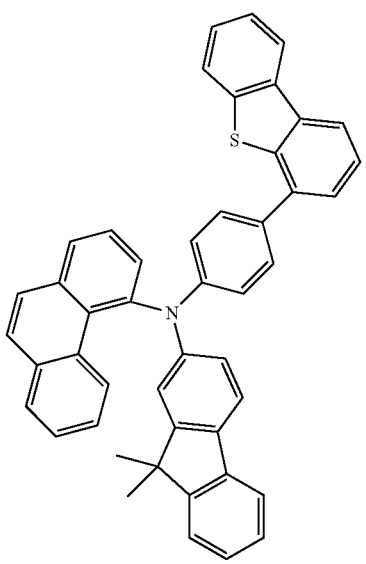
343
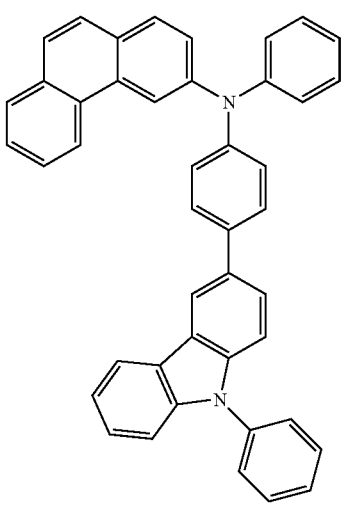

344
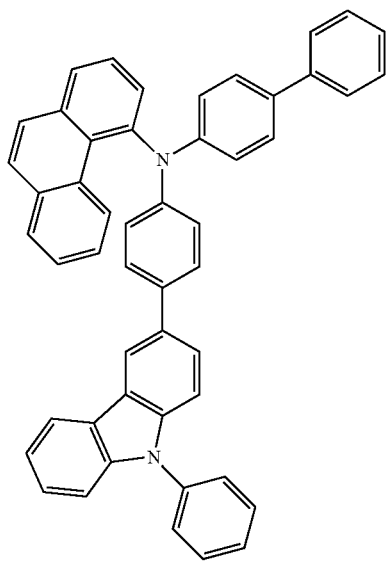
345
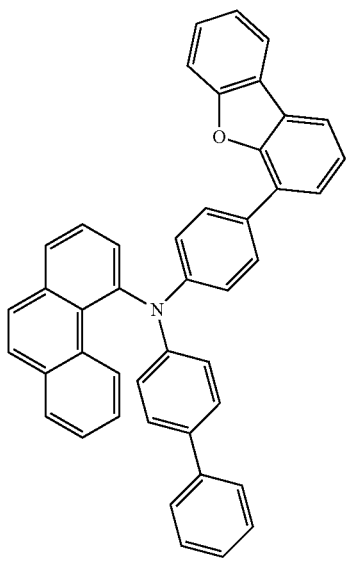
346
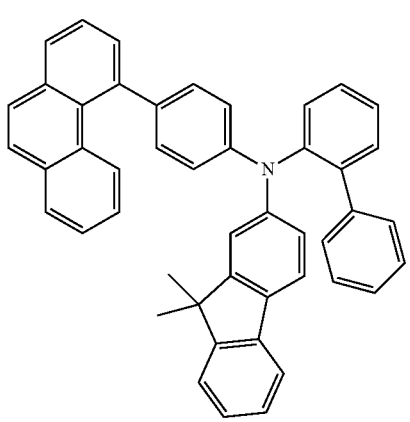
347
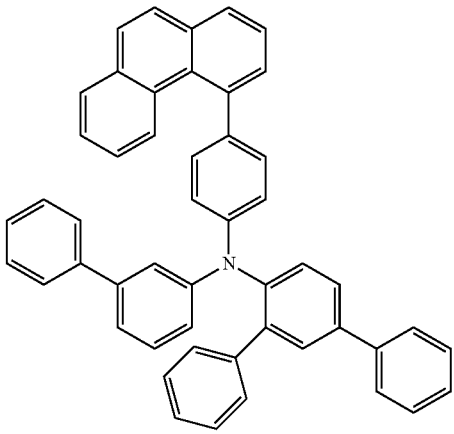
348
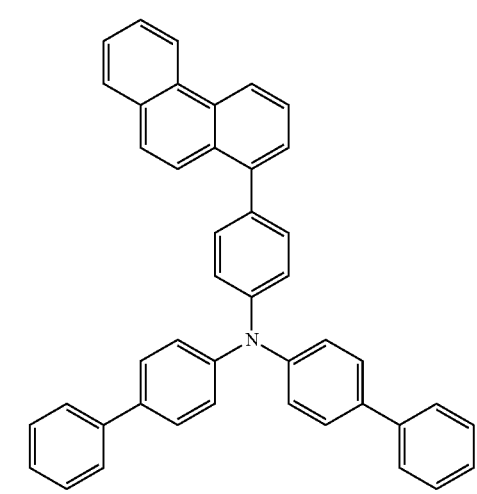
349
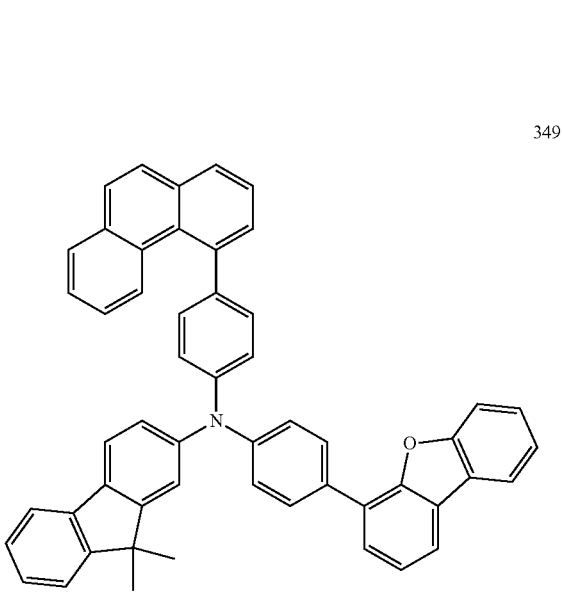

141
-continued
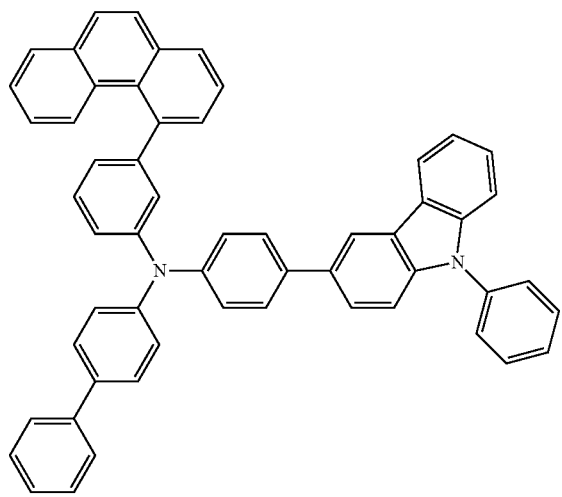
350
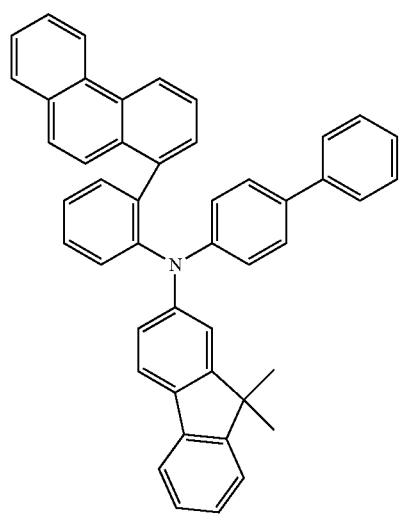
351
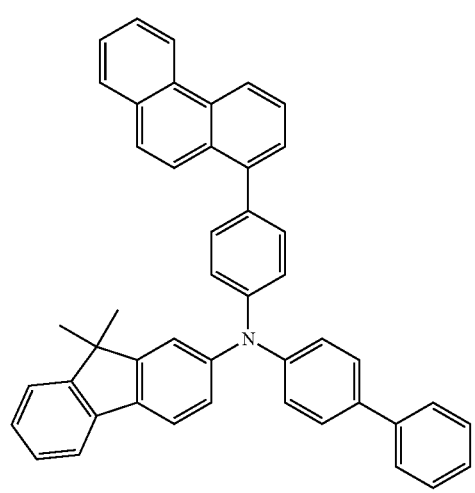
352
142
-continued
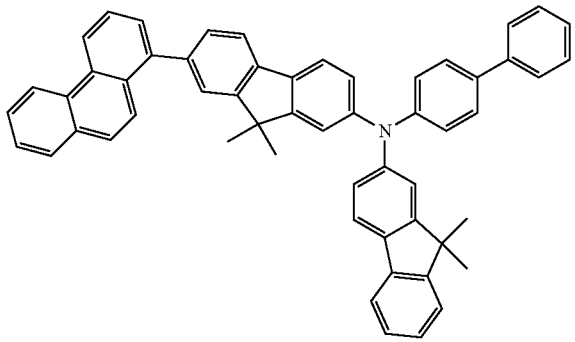
353
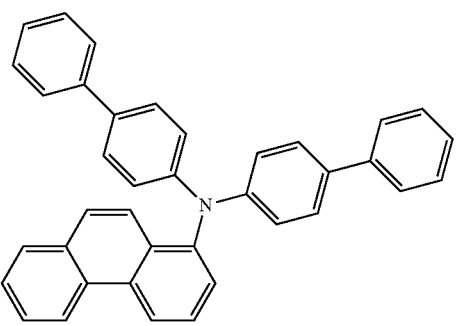
354
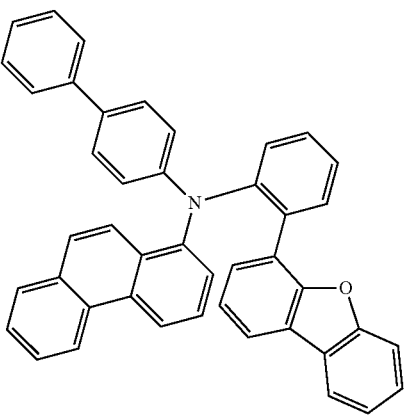
355
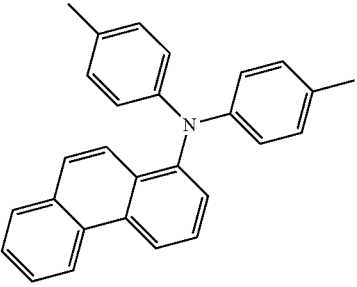
356

357
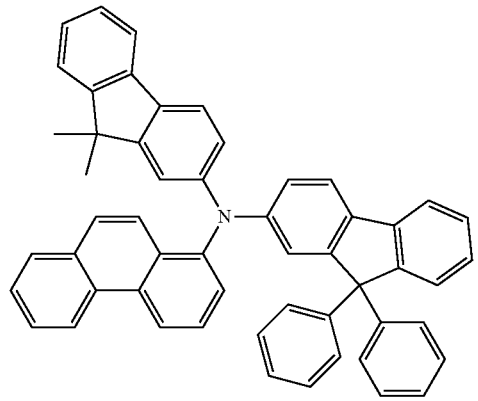
358
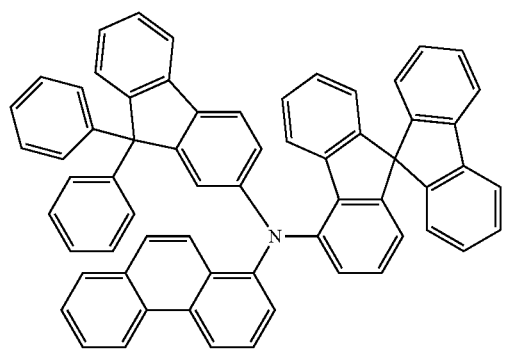
359
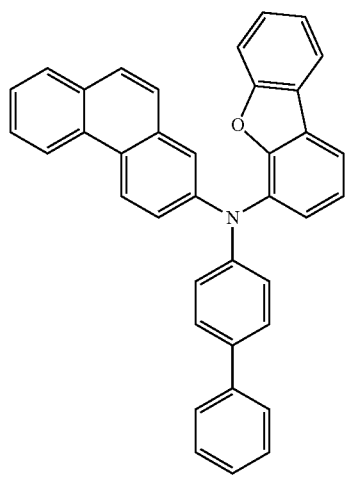
360
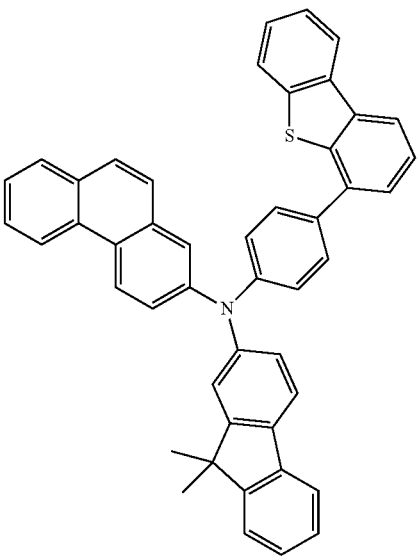
361
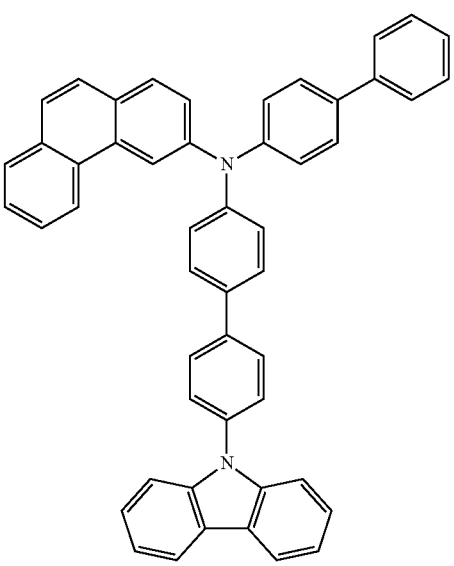

362
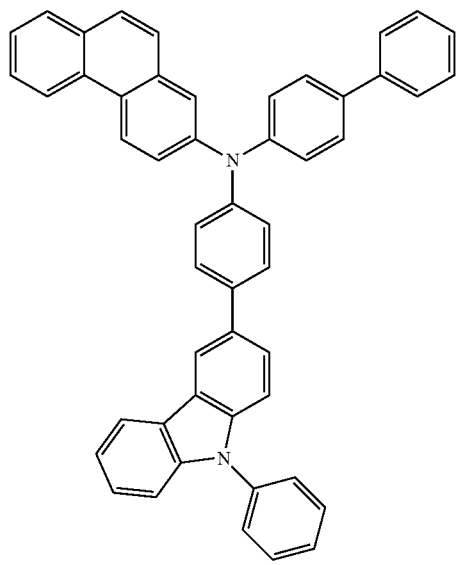
363
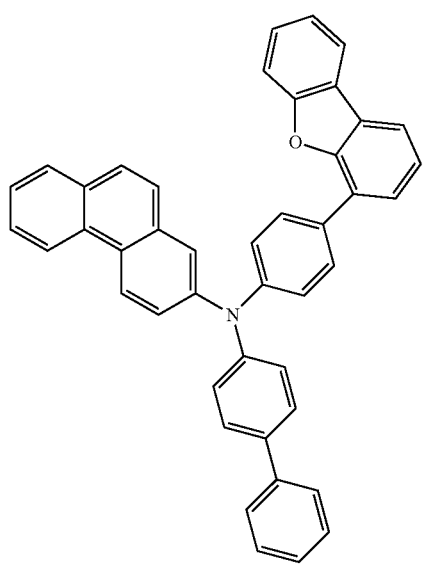
364
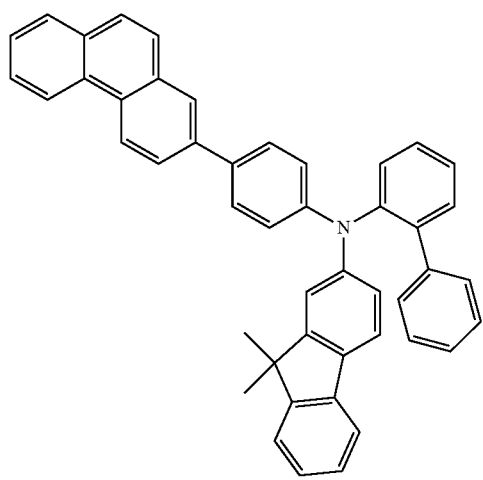
365
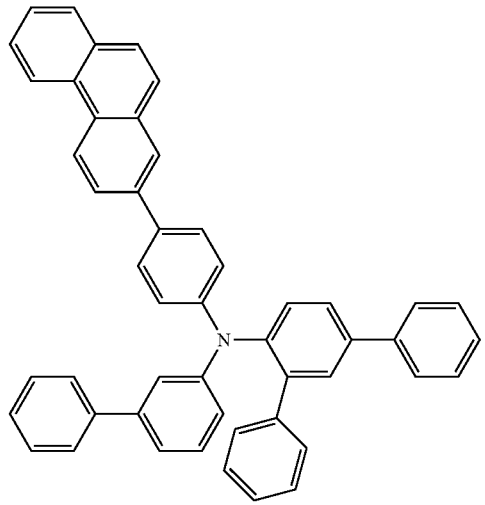
366
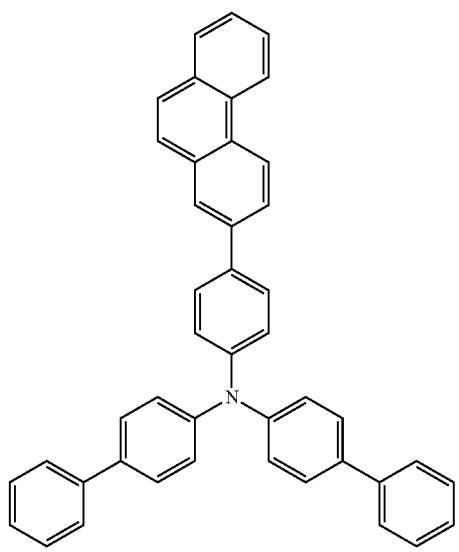
367
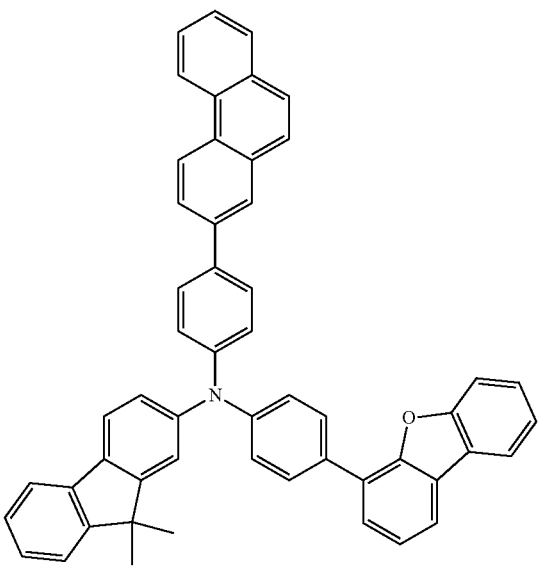

147
-continued
368
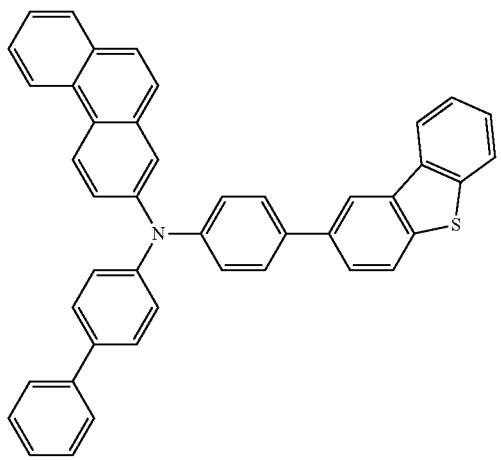
369
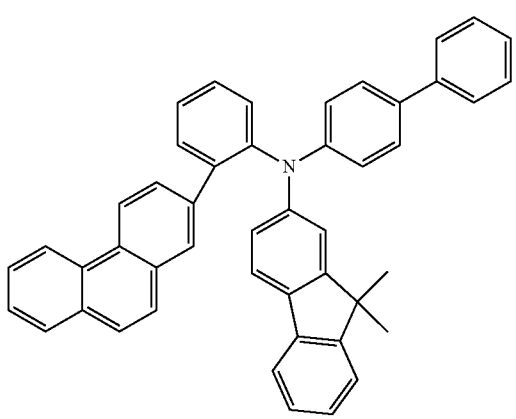
370
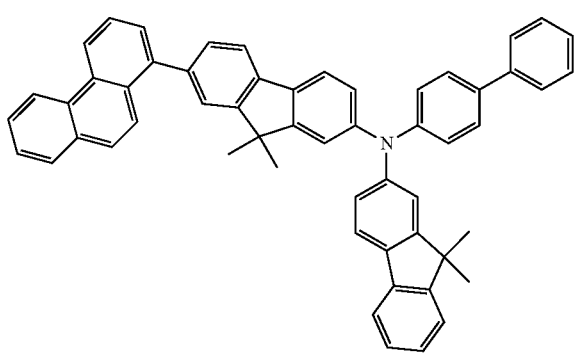
371
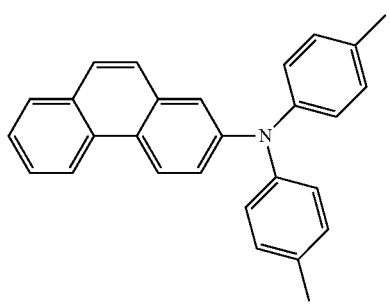
148
-continued
372
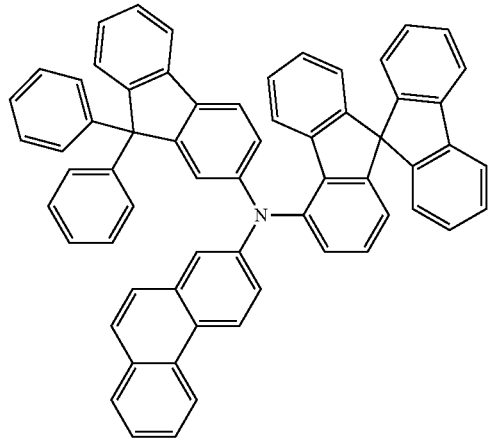
373
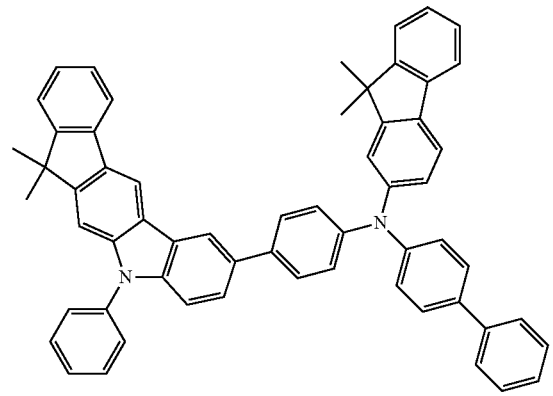
374
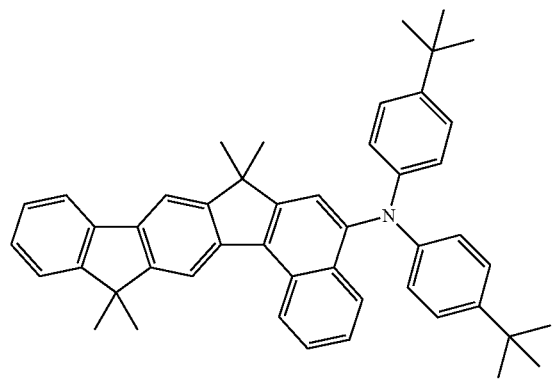
375
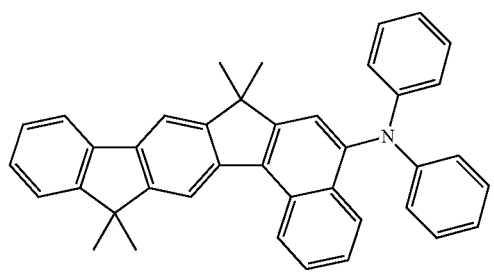

376
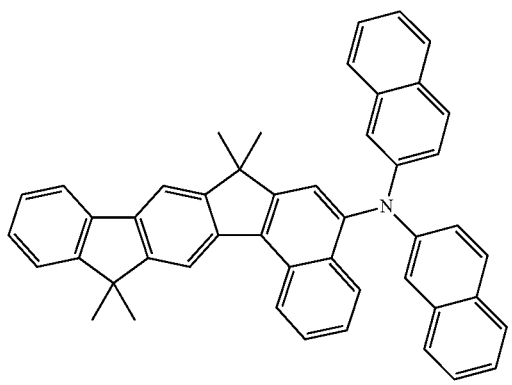
377
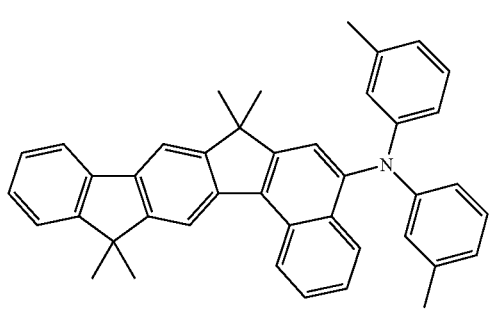
378
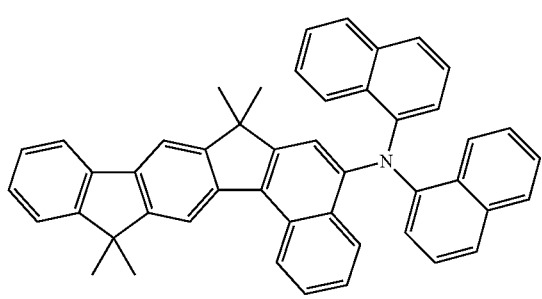
379
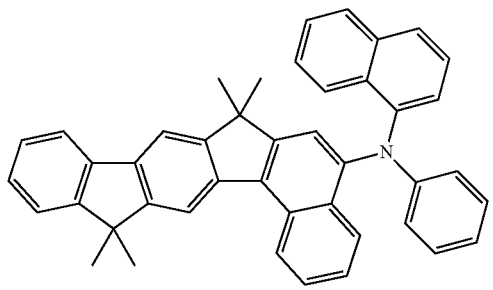
380
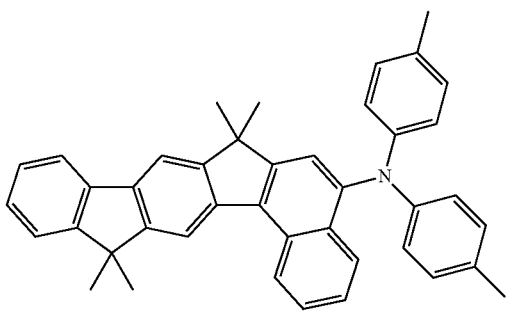
381
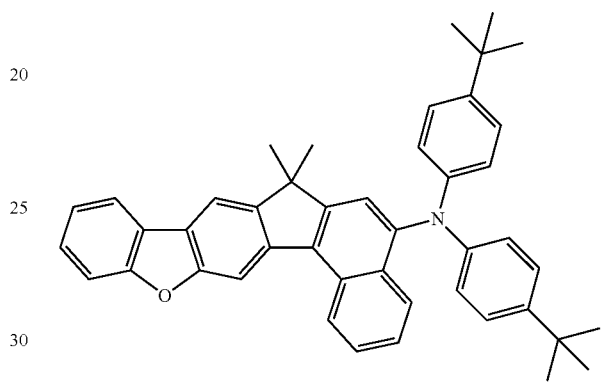
382
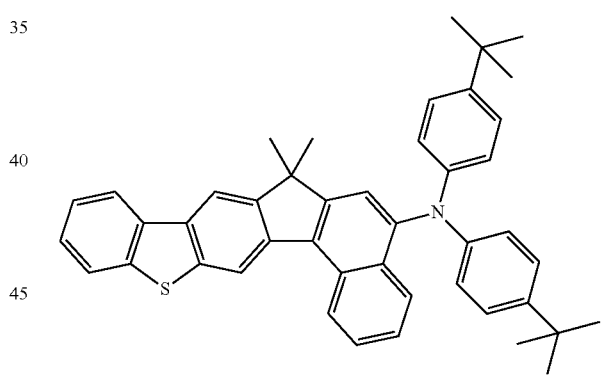
383
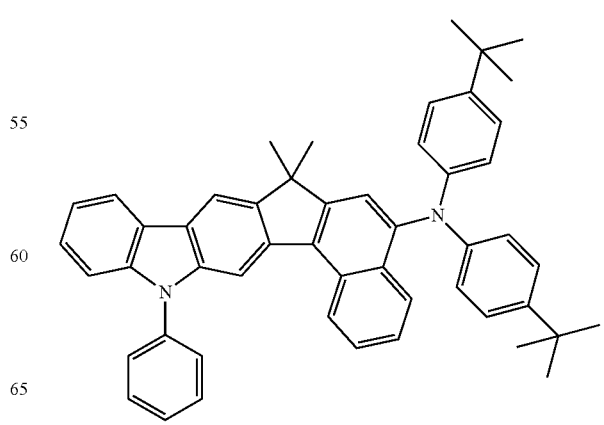

151
-continued
384
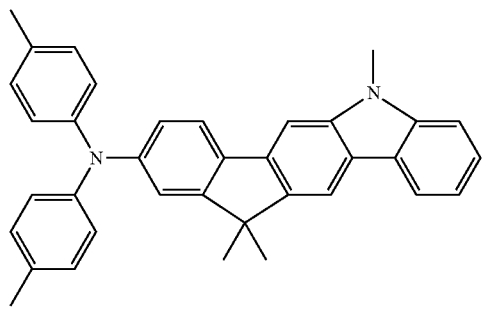
385
152
-continued
388
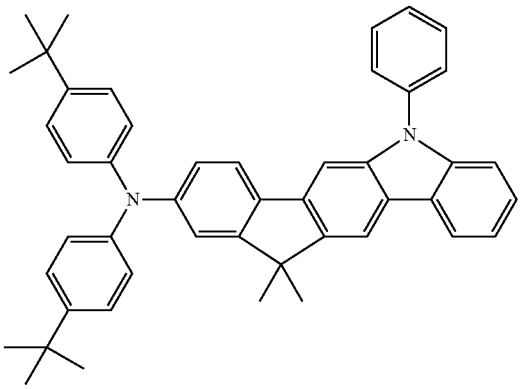
389
386
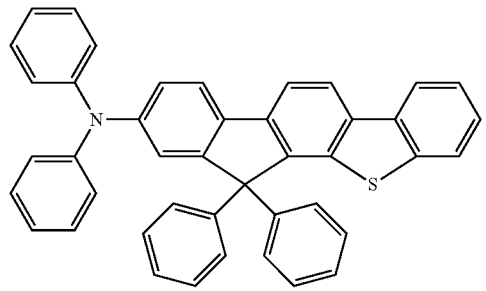
390
387
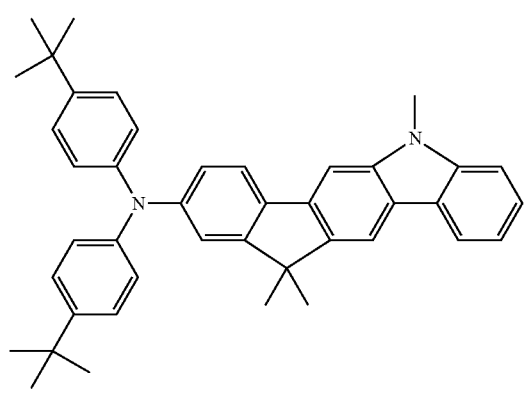
391
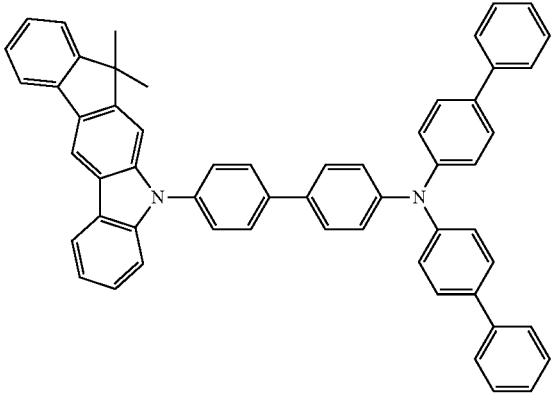

392

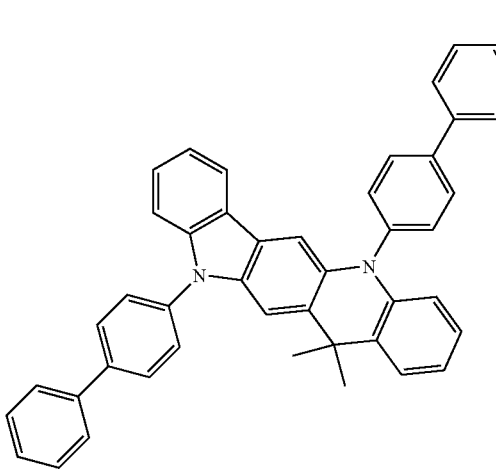

Preparation processes for the various embodiments of compound A are known in the prior art. Among other documents, the person skilled in the art may make reference to the disclosure of documents WO 2006/122630, WO 2006/100896, EP 1661888, WO 2012/034627, WO 2013/120577, WO 2014/015937, WO 2014/015938, WO 2014/015935, WO 2013/083216 and WO 2012/150001.

The compound P is a p-dopant in the sense of the abovementioned definition. Without being bound to this theory, it is assumed that the compound P is a Lewis acid which, when present mixed with the compound A, forms a complex with the compound A. The compound A acts here as a Lewis base. Without being bound to this theory, the complex is formed by virtue of a free electron pair in compound A interacting with the bismuth metal atom of compound P.

The compound P may be a mononuclear complex of bismuth, a binuclear complex of bismuth or a polynuclear complex of bismuth. It is possible that the compound P is a mononuclear complex of bismuth if it is present in the gas phase and a polynuclear complex of bismuth if it is in the solid phase. This means that the compound P may polymerize or depolymerize according to the state of matter.

The complex of bismuth is preferably a complex of bismuth in the (II), (III) or (V) oxidation state. It is more preferably a complex of bismuth in the (III) oxidation state.

Preferably, the complex of bismuth has at least one ligand L which is an organic compound. The ligand L is preferably selected from monodentate, bidentate and tridentate ligands, more preferably from monodentate ligands. Further preferably, the ligand L is negatively charged, preferably triply, doubly or singly negatively charged, more preferably singly negatively charged.

The group of the ligand L that binds to the bismuth atom is preferably selected from carboxylic acid groups, thiocarboxylic acid groups, in particular thiolic acid groups, thionic acid groups and dithiolic acid groups, carboxamide groups and carboximide groups, more preferably from carboxylic acid groups.

Preferably, the ligand L corresponds to one of the following formulae (L-I), (L-II), (L-III) and (L-IV)

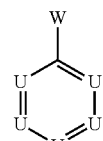
Formula (L-I)

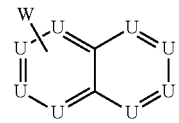
Formula (L-II)

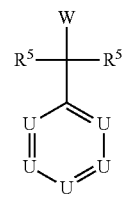
Formula (L-III)

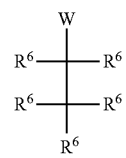
Formula (L-IV)

where;
W is selected from carboxylic acid groups, thiocarboxylic acid groups, in particular thiolic acid groups, thionic acid groups and dithiolic acid groups, carboxamide groups and carboximide groups, more preferably from carboxylic acid groups;
U is the same or different at each instance and is selected from N and $CR^3$ if no W group is bonded thereto, and U is C when a W group is bonded thereto; and
$R^3$ is the same or different at each instance and is selected from H, D, F, Cl, Br, I, CN, $NO_2$, $CF_3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by —$R^4C$=$CR^4$—, —C≡C—, $Si(R^4)_2$, C=O, C=$NR^4$, —C(=O)O—, —C(=O)$NR^4$—, P(=O)($R^4$), —O—, —S—, SO or $SO_2$; and
$R^4$ is the same or different at each instance and is selected from H, D, F, Cl, CN, $NO_2$, alkyl groups having 1 to 20 carbon atoms, aromatic ring systems having 6 to 40 aromatic ring atoms and heteroaromatic ring systems having 5 to 40 aromatic ring atoms; where two or more $R^4$ radicals may be joined to one another and may form a ring; and where the alkyl groups, aromatic ring systems and heteroaromatic ring systems mentioned may be substituted by F, Cl, CN and $NO_2$; and
$R^5$ is the same or different at each instance and is selected from H, D, F, C(=O)$R^4$, CN, $Si(R^4)_3$, P(=O)($R^4$)$_2$, $OR^4$, S(=O)$R^4$, S(=O)$_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by $—R^4C=CR^4—$, $—C≡C—$, $Si(R^4)_2$, $C=O$, $C=NR^4$, $—C(=O)O—$, $—C(=O)NR^4—$, $P(=O)(R^4)$, $—O—$, $—S—$, SO or $SO_2$; and $R^6$ is the same or different at each instance and is selected from H, D, F, Cl, Br, I, CN, $NO_2$, $CF_3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by $—R^4C=CR^4—$, $—C≡C—$, $Si(R^4)_2$, $C=O$, $C=NR^4$, $—C(=O)O—$, $—C(=O)NR^4—$, $P(=O)(R^4)$, $—O—$, $—S—$, SO or $SO_2$.

Preferably, in each of the formulae (L-I) to (L-III), at least one $R^3$ group is present, selected from F, Cl, Br, I, CN, $NO_2$ and alkyl groups which have 1 to 20 carbon atoms and at least one substituent selected from F, Cl, CN and $NO_2$. Among the groups mentioned, particular preference is given to F, Cl, CN and $CF_3$.

More preferably, one, two or three $R^3$ groups of this kind are present, most preferably three.

Preferably, in formula (L-IV), at least one $R^6$ group is present, selected from F, Cl, Br, I, CN, $NO_2$ and alkyl groups which have 1 to 20 carbon atoms and at least one substituent selected from F, Cl, CN and $NO_2$. Among the groups mentioned, particular preference is given to F, Cl, CN and $CF_3$.

More preferably, one, two or three $R^6$ groups of this kind are present, most preferably three.

Preferred ligands L are selected from fluorinated benzoic acid derivatives, fluorinated or non-fluorinated phenylacetic acid derivatives and fluorinated or non-fluorinated acetic acid derivatives.

Examples of preferred fluorinated benzoic acid derivatives are: 2-(trifluoromethyl)benzoic acid; 3,5-difluorobenzoic acid; 3-hydroxy-2,4,6-triiodobenzoic acid; 3-fluoro-4-methylbenzoic acid; 3-(trifluoromethoxy)benzoic acid; 4-(trifluoromethoxy)benzoic acid; 4-chloro-2,5-difluorobenzoic acid; 2-chloro-4,5-difluorobenzoic acid; 2,4,5-trifluorobenzoic acid; 2-fluorobenzoic acid; 4-fluorobenzoic acid; 2,3,4-trifluorobenzoic acid; 2,3,5-trifluorobenzoic acid; 2,3-difluorobenzoic acid; 2,4-bis(trifluoromethyl)benzoic acid; 2,4-difluorobenzoic acid; 2,5-difluorobenzoic acid; 2,6-bis(trifluoromethyl)benzoic acid; 2,6-difluorobenzoic acid; 2-chloro-6-fluorobenzoic acid; 2-fluoro-4-(trifluoromethyl)benzoic acid; 2-fluoro-5-(trifluoromethyl)benzoic acid; 2-fluoro-6-(trifluoromethyl)benzoic acid; 3,4,5-trifluorobenzoic acid; 3,4-difluorobenzoic acid; 3,5-bis(trifluoromethyl)benzoic acid; 3-(trifluoromethyl)benzoic acid; 3-chloro-4-fluorobenzoic acid; 3-fluoro-5-(trifluoromethyl)benzoic acid; 3-fluorobenzoic acid; 4-fluoro-2-(trifluoromethyl)benzoic acid; 4-fluoro-3-(trifluoromethyl)benzoic acid; 5-fluoro-2-methyl benzoic acid; 2-(trifluoromethoxy)benzoic acid; 2,3,5-trichlorobenzoic acid; 4-(trifluoromethyl)benzoic acid; pentafluorobenzoic acid; and 2,3,4,5-tetrafluorobenzoic acid.

Examples of fluorinated or non-fluorinated phenylacetic acid derivatives are: 2-fluorophenylacetic acid; 3-fluorophenylacetic acid; 4-fluorophenylacetic acid; 2,3-difluorophenylacetic acid; 2,4-difluorophenylacetic acid; 2,6-difluorophenylacetic acid; 3,4-difluorophenylacetic acid; 3,5-difluorophenylacetic acid; pentafluoro-phenylacetic acid; 2-chloro-6-fluorophenylacetic acid; 2-chloro-3,6-difluorophenylacetic acid; 3-chloro-2,6-difluorophenylacetic acid; 3-chloro-4-fluorophenylacetic acid; 5-chloro-2-fluorophenylacetic acid; 2,3,4-trifluorophenylacetic acid; 2,3,5-trifluorophenylacetic acid; 2,3,6-trifluorophenylacetic acid; 2,4,5-trifluorophenylacetic acid; 2,4,6-trifluorophenylacetic acid; 3,4,5-trifluorophenylacetic acid; 3-chloro-2-fluorophenylacetic acid; 6-fluorophenylacetic acid; 4-chloro-2-fluorophenylacetic acid; 2-chloro-4-fluorophenylacetic acid.

Examples of fluorinated or non-fluorinated acetic acid derivatives are: difluoroacetic acid; trifluoroacetic acid; chlorodifluoroacetic add; (3-chlorophenyl)difluoroacetic acid; (3,5-difluorophenyl)difluoroacetic acid; (4-butylphenyl) difluoroacetic acid; (4-tert-butylphenyl)difluoroacetic acid; (3,4-dimethylphenyl)difluoroacetic acid; (3-chloro-4-fluorophenyl)-difluoroacetic acid; (4-chlorophenyl)-difluoroacetic add; 2-biphenyl-3',5'-difluoroacetic acid; 3-biphenyl-3',5'-difluoroacetic acid; 4-biphenyl-3',5'-difluoroacetic acid; 2-biphenyl-3',4'-difluoroacetic acid; 3-biphenyl-3',4'-difluoroacetic acid; 4-biphenyl-3',4'-difluoroacetic acid and 2,2-difluoropropionic acid and higher homologues thereof.

The compounds mentioned in deprotonated form in the above list may also be present in protonated form in accordance with the invention. They are preferably in deprotonated form. The compounds mentioned in protonated form in the above list may also be present in deprotonated form, which is preferred in accordance with the invention.

The material of the invention may contain further compounds. It preferably contains essentially exclusively exactly one compound A and exactly one compound P. If further compounds are present, these are preferably compounds according to formula (A). In one possible embodiment of the invention, exactly two different compounds A and exactly one compound P are present in the material of the invention.

The compound P is preferably present as a dopant in the material of the invention. It is preferable that the material of the invention contains the compound P in a concentration of 0.1% to 20%, more preferably 0.5% to 12%, even more preferably 1% to 8% and most preferably of 2% to 6%.

Percentages in the context of the present application are stated such that they mean % by volume in the case of gas phase deposition and % by weight in the case of application from the liquid phase.

The material of the invention is preferably in the form of a thin layer, more preferably of a functional layer of an electronic device. The present invention therefore also provides a layer, preferably a semiconductor layer, comprising the material of the invention.

The layer comprising the material of the invention preferably has a thickness of 1 to 500 nm, more preferably of 5 to 300 nm and most preferably of 8 to 250 nm. It is preferably used as hole-transporting layer in an electronic device, preferably of an OLED, as laid out in detail further down.

The material of the invention can be applied in the form of a layer from the gas phase, for example by means of the OVPD (organic vapour phase deposition) method or with the aid of carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301). Alternatively, the material can also be produced from the liquid phase, for example by spin-coating, or by any printing method, for example screen printing, flexographic printing, nozzle printing or offset printing, preferably LITI (light-induced thermal imaging, thermal transfer printing) or inkjet printing.

For the processing of the material of the invention from the liquid phase, for example by the abovementioned methods, formulations are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising the material of the invention and at least one solvent, preferably an organic solvent. The way in which such a formulation, especially such solutions, can be prepared is known to those skilled in the art and is described, for example, in WO 2002/072714, WO 2003/019694 and the literature cited therein.

In the case of gas phase deposition, both compound P and compound A are coevaporated, preferably from different vapour deposition sources, and deposited as a layer. In the case of application from the liquid phase, the compound P and the compound A are dissolved in solvent and then applied by means of the abovementioned printing techniques. The layer comprising the material of the invention is finally obtained by evaporating the solvent.

The present application therefore also provides a process for producing a layer comprising the material of the invention, characterized in that compound A and compound P are applied together from the gas phase, or in that a formulation comprising the material of the invention is applied from the liquid phase.

The material of the invention is suitable for use in electronic devices, preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

This material may be used in different functions. Preference is given to the use of the material in a hole-transporting layer, for example a hole injection layer, a hole transport layer, an exciton blocker layer or an electron blocker layer. The above-described use of the material likewise forms part of the subject-matter of the invention.

A hole transport layer according to the present application is a layer having a hole-transporting function between the anode and emitting layer.

Hole injection layers and electron blocker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocker layer, in the case of a plurality of hole transport layers between the anode and emitting layer, is that hole transport layer which directly adjoins the emitting layer on the anode side.

The invention further provides an electronic device comprising the material of the invention, preferably in the form of a layer. This electronic device is preferably selected from the abovementioned devices. More preferably, the electronic device is an OLED comprising anode, cathode and at least one emitting layer, characterized in that at least one layer, preferably a hole-transporting layer, comprises the material of the invention.

Apart from the cathode, anode and emitting layer, the OLED preferably comprises still further functional layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the OLED comprising the material of the invention is preferably as follows:
  anode
  hole injection layer
  hole transport layer
  optionally further hole transport layer
  optionally electron blocker layer
  emitting layer
  optionally hole blocker layer
  electron transport layer
  electron injection layer
  cathode.

However, it is not necessary for all the layers mentioned to be present, and further layers may additionally be present.

The OLED of the invention may comprise several emitting layers. More preferably, these emission layers in this case have several emission maxima between 380 nm and 750 mm overall, such that the overall result is white emission; in other words, various emitting compounds which may fluoresce or phosphoresce and which emit blue, yellow, green, orange or red light are used in the emitting layers. Especially preferred are three-layer systems, i.e. systems having three emitting layers, where the three layers show blue, green and orange or red emission (for the basic construction see, for example, WO 2005/011013).

Preferably, the OLED comprises the material of the invention in a hole-transporting layer disposed between the anode and emitting layer, with one or more further layers preferably present between the layer comprising the material of the invention and the emitting layer. Preferably, these further layers are hole transport layers, more preferably electron blocker layers. The further layers mentioned may be p-doped or non-p-doped.

In a preferred embodiment of the invention, the HOMO levels of the hole-transporting layer (HTL) and the layer between the hole-transporting layer and emitting layer (EBL) meet the following condition:
HOMO(HTL)<=HOMO(EBL).

In this way, it is possible to avoid a hole barrier and hence a voltage drop between the hole transport layer and the emitting layer. This is advantageously possible, for example, through the use of the same material in the hole transport layer and the further layer between the hole transport layer and emitting layer.

However, it may also be preferable that the material of the invention is disposed in a hole-transporting layer directly adjoining the emitting layer.

The hole transport layers disposed between the layer comprising the material of the invention and the emitting layer preferably comprise one or more identical or different compounds of the formula (A), preferably different compounds of the formula (A).

The OLED of the invention may have a multitude of hole transport layers. There are preferably one, two, three, four or five hole transport layers, more preferably two, three or four hole transport layers, at least one of which comprises the material of the invention.

It is further preferable that the OLED comprises the material of the invention in a layer directly adjoining the anode.

More preferably, the OLED of the invention comprises one of the following layer structures:
a) anode—layer comprising the material of the invention—electron blocker layer—emitting layer;
b) anode—layer comprising the material of the invention—hole transport layer—electron blocker layer—emitting layer;
c) anode—first layer comprising the material of the invention—hole transport layer—second layer comprising the material of the invention—electron blocker layer—emitting layer.

Those layers that preferably adjoin the emitting layer on the cathode side correspond to the abovementioned preferred layers in these positions, namely one or more hole blocker layers, electron transport layers and electron injection layers.

In structure a), it is possible for both the layer comprising the material of the invention and the electron blocker layer to comprise the same compound of the formula (A). In structure c), both the layer comprising the material of the invention and the hole transport layer may comprise the same compound of the formula (A) and/or both the second layer comprising the material of the invention and the electron blocker layer may comprise the same compound of the formula (A).

It is additionally preferable that the electron blocker layer in the OLED of the invention, or that layer which directly adjoins the emitting layer on the anode side, comprises a compound of the formula (A), especially a compound of the formula (A) which is a monoarylamine.

It is preferable when the material of the invention is used in an OLED comprising one or more phosphorescent emitting compounds. The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preferred phosphorescent emitting compounds are compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the material of the invention in an OLED.

In an alternative embodiment, it is preferable that the material is used in an OLED comprising a fluorescent emitting compound in its emitting layer. Preferably, the emitting layer in this case comprises an arylamino compound as fluorescent emitting compound, more preferably in combination with a host material. The host material in this case is preferably selected from compounds comprising one or more anthracene groups.

Preferred embodiments of the different functional materials in the electronic device are listed hereinafter.

Preferred phosphorescent emitting compounds are the abovementioned compounds.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups in the pyrene are bonded preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522 and the extended benzoindenofluorenes disclosed in WO 2014/111269.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulphoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulphoxides. Very particularly preferred matrix materials are selected from the classes of the oligoarylenes comprising, anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and the pyrene compounds disclosed in EP 1749809, EP 1905754 and US 2012/0187826.

Preferred matrix materials for phosphorescent emitting compounds are aromatic ketones, aromatic phosphine oxides or aromatic sulphoxides or sulphones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the formula (A), for example, the compounds disclosed in Y. Shirota et al., Chem. Rev. 2007, 107(4), 953-1010, or other materials as used in these layers according to the prior art.

Examples of preferred materials which can be used in a hole transport, hole injection or electron blocker layer in the electroluminescent device of the invention are, as well as the compounds of the formula (A), indenofluorenamine derivatives (for example according to WO 06/122630 or WO 06/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 and WO 2013/120577), fluoreneamines (for example according to WO 2014/015937, WO 2014/015938 and WO 2014/015935), spirodibenzopyranamines (for example according to WO 2013/083216) and dihydroacridine derivatives (for example according to WO 2012/150001).

Materials used for the electron transport layer may be any materials as used according to the prior art as electron transport materials in the electron transport layer. Especially suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. On the other hand, metal/metal oxide electrodes (e.g. Al/Ni/NiO$_x$, Al/PtO$_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar. Preferred methods for application of layers from the gas phase are described further up, and apply generally to the production of layers in the OLEDs of the invention.

In an alternative embodiment, the electronic device is characterized in that one or more layers are applied from solution. Preferred methods for application of layers from solution are described further up, and apply generally to the production of layers in the OLEDs of the invention.

It is further preferable that an electronic device of the invention is produced by applying one or more layers from solution and one or more layers by a sublimation method.

The OLEDs of the invention can be used in displays, as light sources in lighting applications and as light sources in medical and/or cosmetic applications (for example light therapy).

WORKING EXAMPLES

A) Synthesis of bis[[3,5-bis(trifluoromethyl)benzoyl]oxy]bismuthanyl 3,5-bis(trifluoromethyl)benzoate

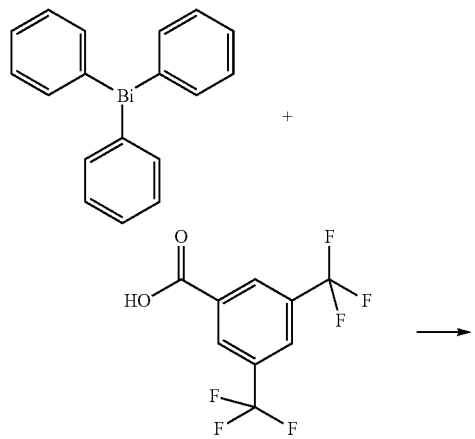

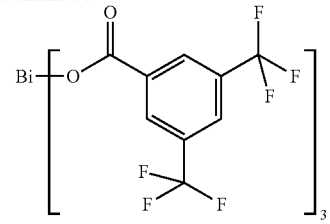

50 g (113.56 mmol) of triphenylbismuthane (CAS No.: 603-33-8) and 89.40 g of 3,5-bis(trifluoromethyl)benzoic acid (340.36 mmol) are initially charged in a flask inertized under argon and 1 l of dried toluene is added. The mixture is heated gradually to 80° C. and then stirred at this temperature for a further 12 hours. The mixture is subsequently cooled to room temperature and filtered through a protective gas frit, washed three times with toluene, dried at the vacuum pump and then sublimed under high vacuum.

B) Device Examples

In examples I1 to I8 and C1 to C2 which follow, the data of various OLEDs are presented. Examples C1 to C2 are comparative examples according to the prior art; examples I1 to I8 show data of OLEDs of the invention.

OLEDs of the invention and OLEDs according to the prior art are produced by a general method according to WO 2004/058911, which is adapted to the circumstances described here (variation in layer thickness, materials). Glass plaques which have been coated with structured ITO (indium tin oxide) in a thickness of 50 nm are the substrates for the OLEDs. The substrates are subjected to wet cleaning (cleaning machine, detergent: Merck Extran), then baked at 250° C. for 15 min and, prior to the coating, treated with an oxygen plasma.

Various layers are applied to the pretreated substrates: first hole transport layer (HTL1)/second hole transport layer (HTL2)/emission layer (EML)/electron transport layer (ETL)/electron injection layer (EIL) and finally a 100 nm-thick aluminium cathode. The exact structure of the OLEDs can be found in Table 1. The materials used for production of the OLEDs are shown in Table 2.

All materials are applied by thermal vapour deposition in a vacuum chamber. In this case, the emission layer always consists of at least one matrix material and an emitting compound which is added to the matrix material(s) in a particular proportion by volume by co-evaporation. Details given in such a form as M1:D1 (95%:5%) mean here that the material M1 is present in the layer in a proportion by volume of 95% and D1 in a proportion by volume of 5%. Analogously, the electron transport layer may also consist of a mixture of two materials.

The OLEDs are characterized in a standard manner. For this purpose, the electroluminescence spectra and the external quantum efficiency (EQE, measured in percent) are determined as a function of luminance, calculated from current-voltage-luminance characteristics (IUL characteristics) assuming Lambertian radiation characteristics, and the lifetime. The electroluminescence spectra are determined at a luminance of 1000 cd/m$^2$, and the CIE 1931 x and y color coordinates are calculated therefrom. The lifetime LT80 is defined as the time after which the luminance drops from the starting luminance to 80% of the start value in the course of operation with constant current density.

TABLE 1

Structure of the OLEDs

| Ex. | HTL1 thickness | HTL2 thickness | EML thickness | ETL thickness | EIL thickness |
|---|---|---|---|---|---|
| V1 | NPB:BiC (95%:5%) 20 nm | NPB 180 nm | M1:D1 (95%:5%) 20 nm | ST1:LiQ (50%:50%) 30 nm | LiQ 1 nm |
| V2 | DA1:BiC (95%:5%) 20 nm | DA1 180 nm | M1:D1 (95%:5%) 20 nm | ST1:LiQ (50%:50%) 30 nm | LiQ 1 nm |
| E1 | MA2:BiC (95%:5%) 20 nm | MA2 180 nm | M1:D1 (95%:5%) 20 nm | ST1:LiQ (50%:50%) 30 nm | LiQ 1 nm |
| E2 | MA4:BiC (95%:5%) 20 nm | MA4 180 nm | M1:D1 (95%:5%) 20 nm | ST1:LiQ (50%:50%) 30 nm | LiQ 1 nm |
| E3 | MA5:BiC (95%:5%) 20 nm | MA5 180 nm | M1:D1 (95%:5%) 20 nm | ST1:LiQ (50%:50%) 30 nm | LiQ 1 nm |
| E4 | MA6:BiC (95%:5%) 20 nm | MA6 180 nm | M1:D1 (95%:5%) 20 nm | ST1:LiQ (50%:50%) 30 nm | LiQ 1 nm |
| E5 | MA7:BiC (95%:5%) 20 nm | MA7 180 nm | M1:D1 (95%:5%) 20 nm | ST1:LiQ (50%:50%) 30 nm | LiQ 1 nm |
| E6 | MA8:BiC (95%:5%) 20 nm | MA8 180 nm | M1:D1 (95%:5%) 20 nm | ST1:LiQ (50%:50%) 30 nm | LiQ 1 nm |
| E7 | MA9:BiC (95%:5%) 20 nm | MA9 180 nm | M1:D1 (95%:5%) 20 nm | ST1:LiQ (50%:50%) 30 nm | LiQ 1 nm |
| E8 | DA2:BiC (95%:5%) 20 nm | DA2 180 nm | M1:D1 (95%:5%) 20 nm | ST1:LiQ (50%:50%) 30 nm | LiQ 1 nm |

TABLE 2

Structural formulae of the materials for the OLEDs

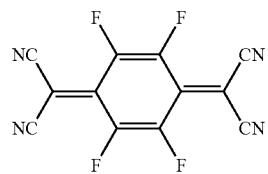 [SMILES: N#CC(C#N)=c1c(F)c(F)c(=C(C#N)C#N)c(F)c1F]

F4TCNQ

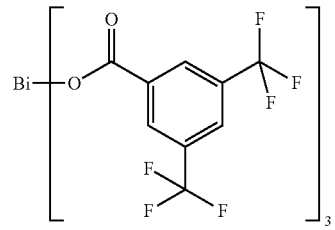

BiC

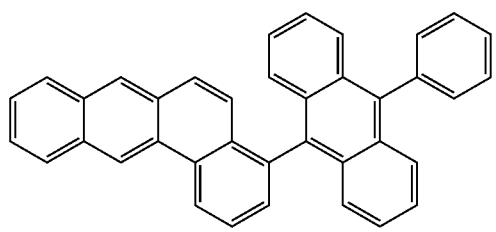 [SMILES: c1ccc(-c2c3ccccc3c(-c3cccc4c3ccc3cc5ccccc5cc34)c3ccccc23)cc1]

M1

TABLE 2-continued

Structural formulae of the materials for the OLEDs

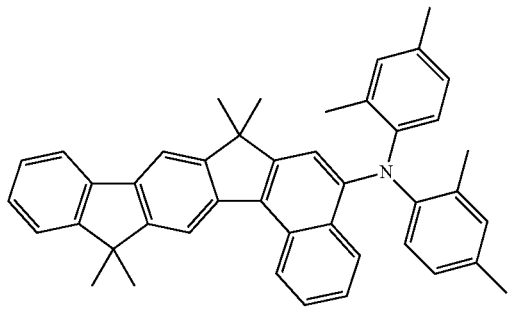 [SMILES: Cc1ccc(N(c2ccc(C)cc2C)c2cc3c(c4ccccc24)-c2cc4c(cc2C3(C)C)-c2ccccc2C4(C)C)c(C)c1]

D1

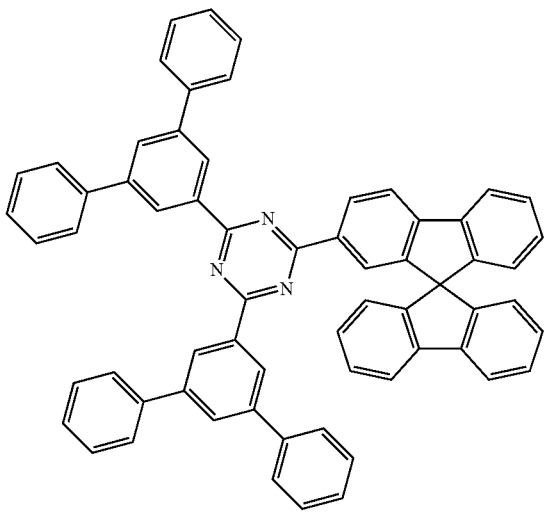 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ST1

TABLE 2-continued
Structural formulae of the materials for the OLEDs
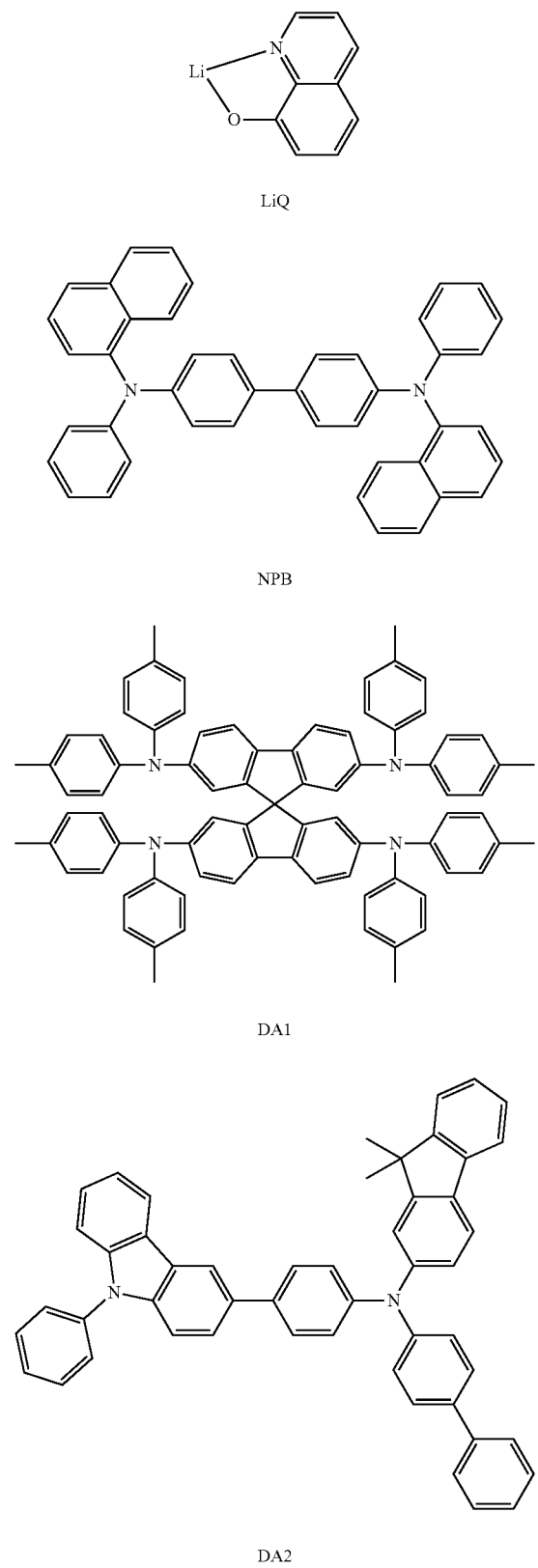
LiQ
NPB
DA1
DA2
TABLE 2-continued
Structural formulae of the materials for the OLEDs
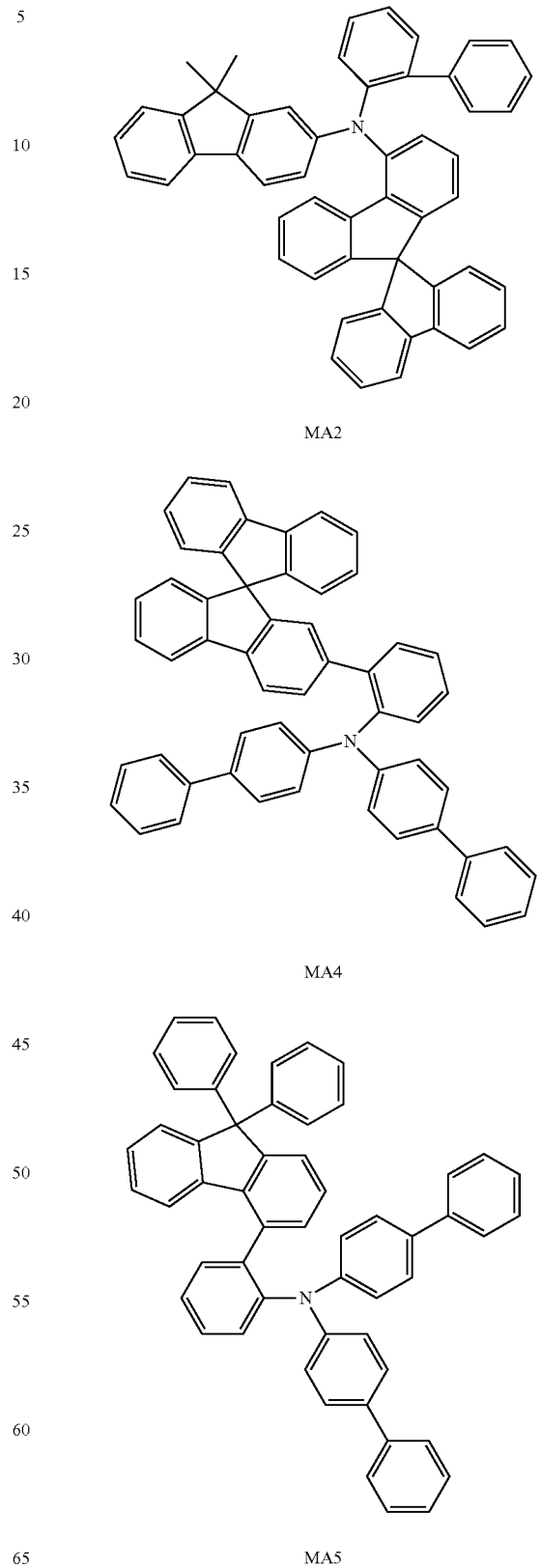
MA2
MA4
MA5

TABLE 2-continued

Structural formulae of the materials for the OLEDs

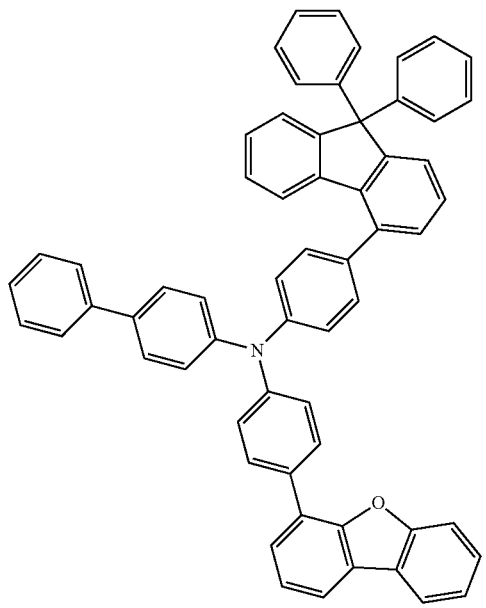 [SMILES: c1ccc(-c2ccc(N(c3ccc(-c4cccc5c4-c4ccccc4C5(c4ccccc4)c4ccccc4)cc3)c3ccc(-c4cccc5c4oc4ccccc45)cc3)cc2)cc1]

MA6

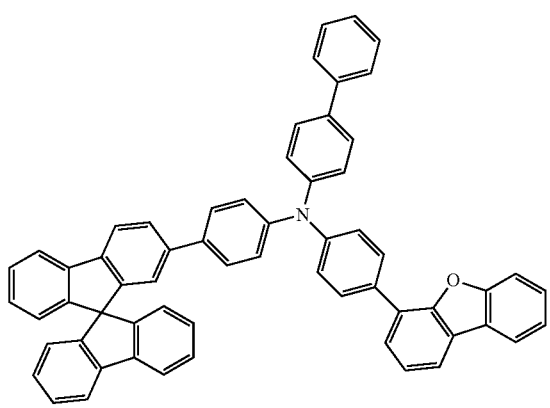 [SMILES: c1ccc(-c2ccc(N(c3ccc(-c4ccc5c(c4)C4(c6ccccc6-c6ccccc64)c4ccccc4-5)cc3)c3ccc(-c4cccc5c4oc4ccccc45)cc3)cc2)cc1]

MA7

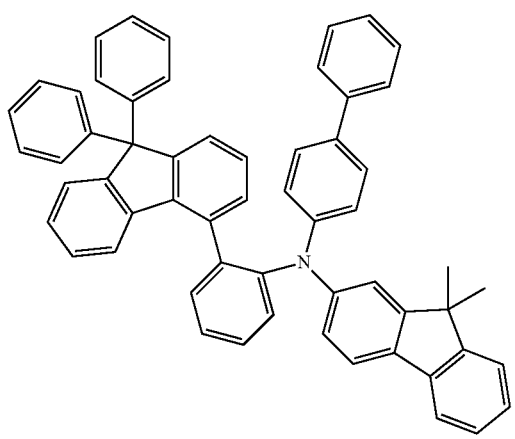 [SMILES: CC1(C)c2ccccc2-c2ccc(N(c3ccc(-c4ccccc4)cc3)c3ccccc3-c3cccc4c3-c3ccccc3C4(c3ccccc3)c3ccccc3)cc21]

MA8

TABLE 2-continued

Structural formulae of the materials for the OLEDs

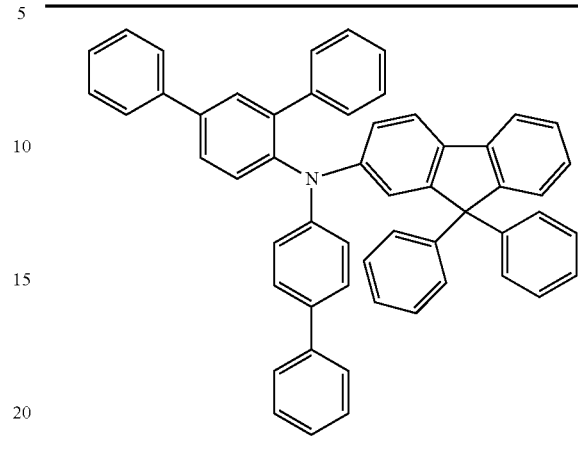

MA9

The examples are elucidated in detail hereinafter, in order to illustrate the advantages of the OLEDs of the invention.

The inventive samples I1 to I8 are compared with the comparative samples C1 and C2. The former differ from C1 and C2 in that they contain a monoarylamine as material for the HTL, and no diamine or tetraamine. In all cases, the p-dopant BiC is used in the first of the two hole-transporting layers present. All inventive samples I1 to I8 have a better lifetime and efficiency than the comparative samples C1 and C2 (Table 3), with similar values for voltage.

TABLE 3

Results for the OLEDs

| Ex. | U @ 10 mA/cm$^2$ | EQE @ 10 mA/cm$^2$ | LT80 @ 60 mA/cm$^2$ |
|---|---|---|---|
| C1 | 4.3 | 5.7 | 195 |
| C2 | 3.8 | 4.1 | 50 |
| I1 | 4.2 | 8.3 | 310 |
| I2 | 4.0 | 7.1 | 375 |
| I3 | 4.2 | 7.9 | 365 |
| I4 | 4.6 | 7.7 | 270 |
| I5 | 4.2 | 7.0 | 250 |
| I6 | 4.3 | 8.4 | 270 |
| I7 | 3.9 | 7.3 | 330 |
| I8 | 4.2 | 7.8 | 210 |

The examples shown illustrate the advantages of the inventive combination of bismuth complexes with monoarylamines of the formula (A) as hole transport materials in OLEDs. They should not be interpreted in a restrictive manner. The advantages of the inventive combination extend over the whole scope of the material combinations defined in the claims.

The invention claimed is:

1. A material comprising a compound P which is a complex of bismuth and a compound A of a formula (A-II) or (A-III)

formula (A-II)

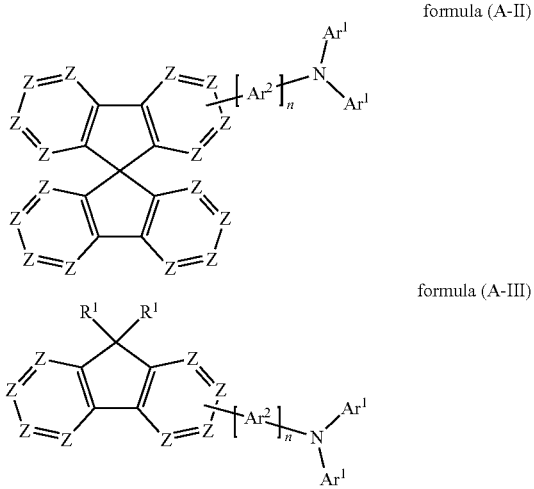

formula (A-III)

where the variables that occur are:
Z is the same or different at each instance and is $CR^1$;
$Ar^1$ is the same or different at each instance and is an aromatic ring system which has 6 to 60 aromatic ring atoms and is optionally substituted by one or more $R^1$ radicals, or a heteroaromatic ring system which has 5 to 60 aromatic ring atoms and is optionally substituted by one or more $R^1$ radicals; $Ar^1$ groups here are optionally bonded to one another via $R^1$ radicals;
$Ar^2$ is an aromatic ring system which has 6 to 20 aromatic ring atoms and may be substituted by one or more $R^1$ radicals, or a heteroaromatic ring system which has 5 to 20 aromatic ring atoms and is optionally substituted by one or more $R^1$ radicals;
$R^1$ is the same or different at each instance and is selected from H, D, F, CN, $Si(R^2)_3$, straight-chain alkyl or alkoxy groups having 1 to 10 carbon atoms, branched or cyclic alkyl or alkoxy groups having 3 to 10 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned may each be substituted by one or more $R^2$ radicals;
$R^2$ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; and where the alkyl groups, aromatic ring systems and heteroaromatic ring systems mentioned is optionally substituted by F or CN;
n is 0 or 1; and
where the scope of the formula (A-II) excludes compounds of the following formula (B)

Formula (B)

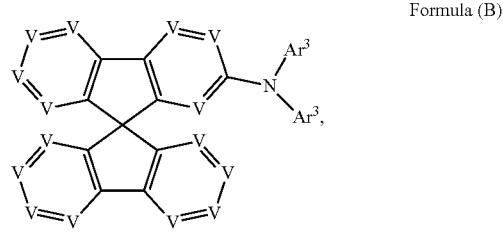

in which the new variables that occur are:
V is $CR^1$;
$Ar^3$ is the same or different at each instance and is an aromatic ring system which has 6 to 30 aromatic ring atoms and is optionally substituted by one or more $R^1$ radicals, or a heteroaromatic ring system which has 5 to 30 aromatic ring atoms and is optionally substituted by one or more $R^1$ radicals; $Ar^3$ groups here are optionally bonded to one another via $R^1$ radicals.

2. The material according to claim 1, wherein the compound A has a single amino group.

3. The material according to claim 1, wherein the compound A does not contain a fused aryl group having more than 10 aromatic ring atoms nor a fused heteroaryl group having more than 14 aromatic ring atoms.

4. The material according to claim 1, wherein, in the compound A, the $Ar^1$ group is the same or different at each instance and is an aromatic ring system which has 6 to 40 aromatic ring atoms and is optionally substituted by one or more $R^1$ radicals, or a heteroaromatic ring system which has 5 to 40 ring atoms and is optionally substituted by one or more $R^1$ radicals.

5. The material according to claim 1, wherein, in the compound A, the $Ar^1$ group is a group which is optionally substituted by one or more $R^1$ radicals and is selected from the group consisting of phenyl, biphenyl, terphenyl, quaterphenyl, naphthyl, phenanthryl, fluoranthenyl, fluorenyl, indenofluorenyl, spirobifluorenyl, dibenzofuranyl, dibenzothiophenyl, carbazolyl, acridyl and phenanthridyl.

6. The material according to claim 1, wherein the compound P is a complex of bismuth in the (III) oxidation state.

7. The material according to claim 1, wherein the compound P is a complex of bismuth having at least one ligand L which is an organic compound.

8. The material according to claim 7, wherein the ligand L is singly negatively charged.

9. The material according to claim 7, wherein the group in the ligand L that binds to the bismuth atom is selected from carboxylic acid groups, thiocarboxylic acid groups, carboxamide groups and carboximide groups.

10. The material according to claim 7, wherein the ligand L is selected from fluorinated benzoic acid derivatives, fluorinated or non-fluorinated phenylacetic acid derivatives and fluorinated or non-fluorinated acetic acid derivatives.

11. The material according to claim 1, wherein the compound P is present in the material as a dopant in a concentration of 0.1% to 20%.

12. A layer comprising the material according to claim 1.

13. A formulation comprising the material according to claim 1 and at least one solvent.

14. A process for producing the layer according to claim 12, which comprises applying the compound A and compound P together from the gas phase.

15. A process for producing a layer which comprises applying a formulation comprising the material according to claim 1 and a solvent from the liquid phase.

16. An electronic device which is an organic electroluminescent device, organic integrated circuits, organic field-effect transistor, organic thin-film transistor, organic light-emitting transistor, organic solar cell, organic optical detecor, organic photoreceptor, organic field-quench device, organic light-emitting electrochemical cell or organic laser diode, comprising the material according to claim 1.

17. The organic electroluminescent device according to claim 16, wherein the device includes the material in a hole-transporting layer disposed between anode and emitting layer, with one or more further layers present between the layer comprising the material and the emitting layer.

18. The organic electroluminescent device according to claim 17, wherein the HOMO levels of the hole-transporting layer (HTL) and the one layer between hole-transporting layer and emitting layer (EBL) meet the following condition:

HOMO(HTL)<=HOMO(EBL).

19. The organic electroluminescent device according to claim 17, wherein the one or more further layers disposed between the layer comprising the material and the emitting layer comprise one or more identical or different compounds of the formula (A).

20. The organic electroluminescent device according to claim 16, wherein the device comprises the material in a layer directly adjoining the anode.

21. The material according to claim 1, wherein the compound A is of the formula (A-II).

22. The material according to claim 1, wherein the compound A is of the formula (A-III).

23. The material according to claim 1, wherein the group $Ar^1$ is selected from one of the formulae ($Ar^1$-1) to ($Ar^1$-88)

($Ar^1$-1)

($Ar^1$-2)

($Ar^1$-3)

($Ar^1$-4)

($Ar^1$-5)

-continued

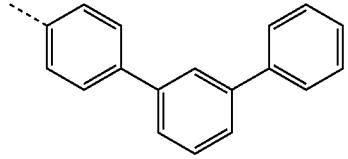
($Ar^1$-6)

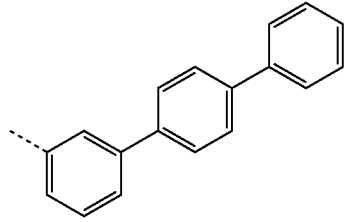
($Ar^1$-7)

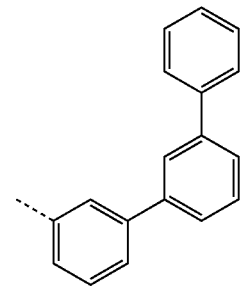
($Ar^1$-8)

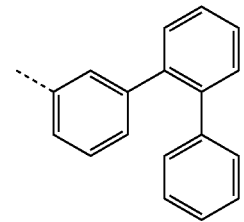
($Ar^1$-9)

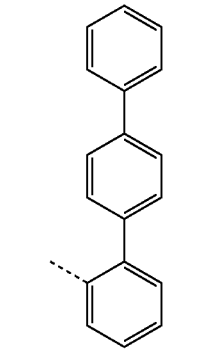
($Ar^1$-10)

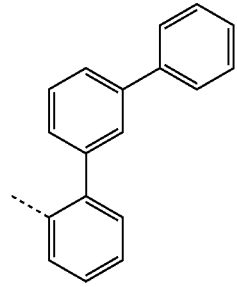
($Ar^1$-11)

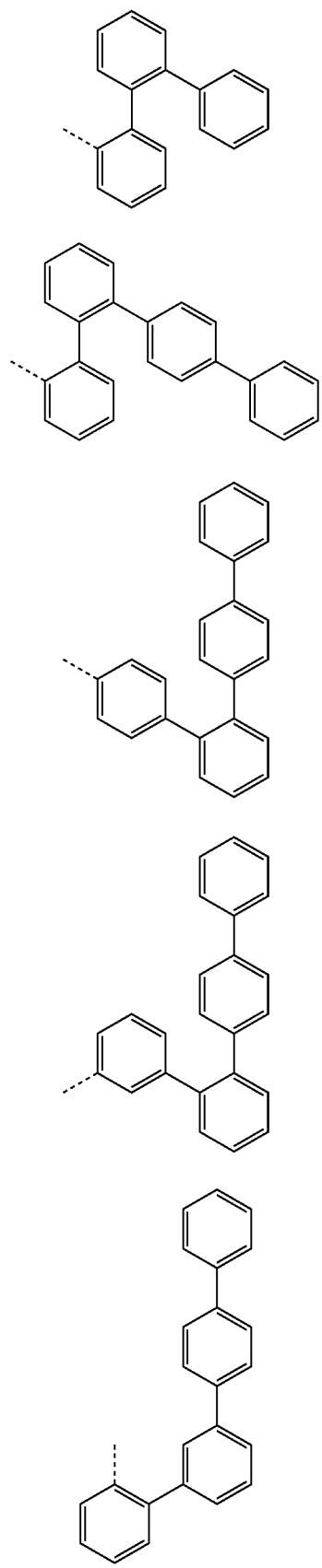

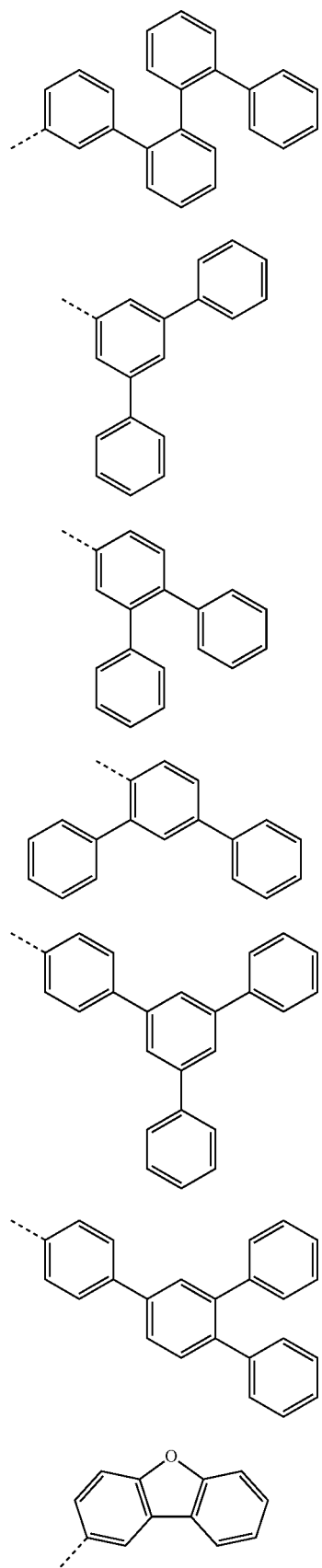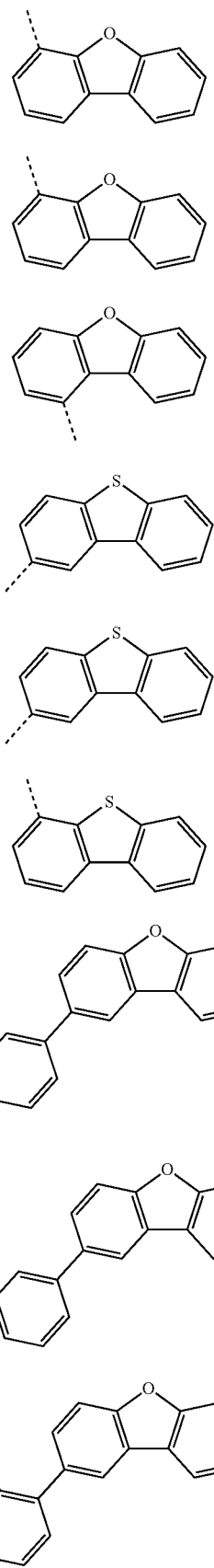

(Ar¹-38)
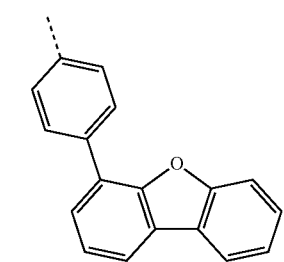
(Ar¹-39)
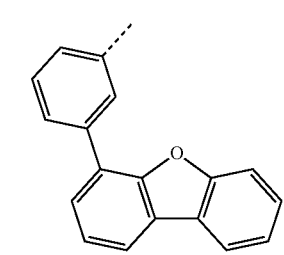
(Ar¹-40)
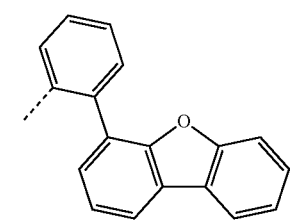
(Ar¹-41)
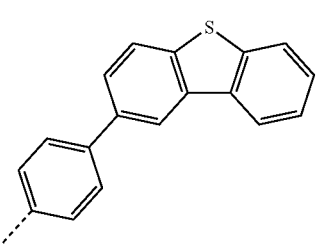
(Ar¹-42)
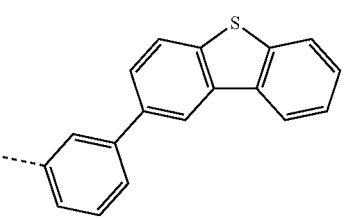
(Ar¹-43)
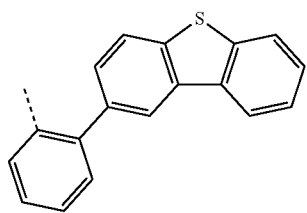
(Ar¹-44)
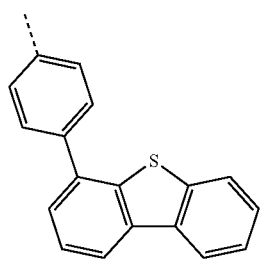
(Ar¹-45)
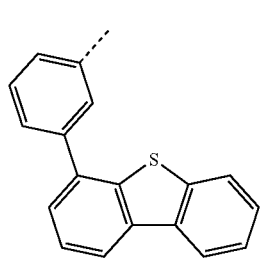
(Ar¹-46)
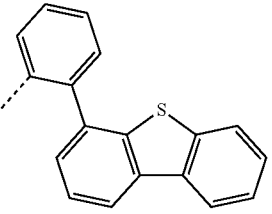
(Ar¹-47)
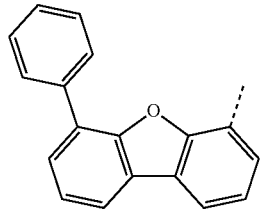
(Ar¹-48)
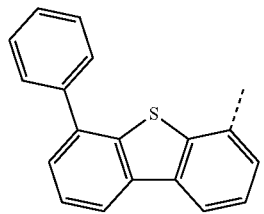
(Ar¹-49)
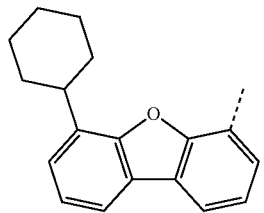

-continued
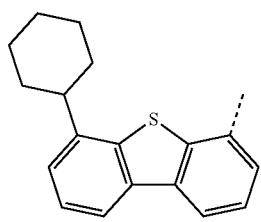 (Ar¹-50)
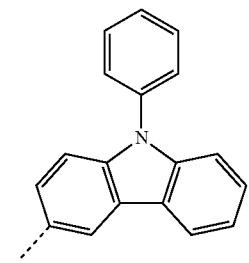 (Ar¹-51)
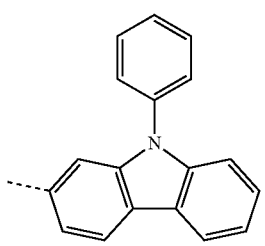 (Ar¹-52)
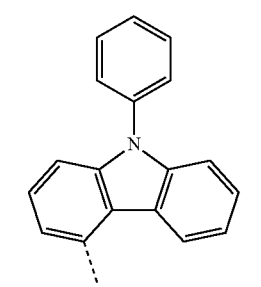 (Ar¹-53)
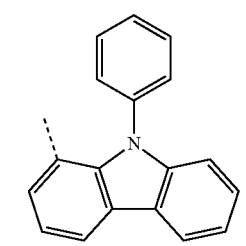 (Ar¹-54)
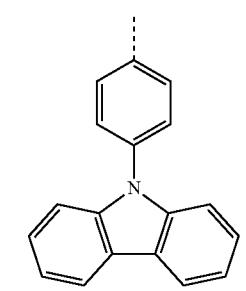 (Ar¹-55)
-continued
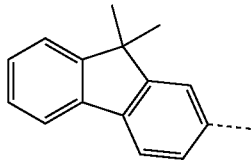 (Ar¹-56)
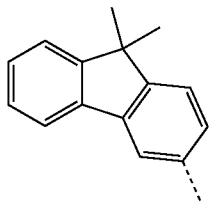 (Ar¹-57)
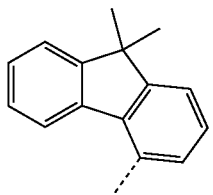 (Ar¹-58)
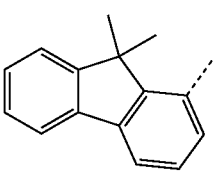 (Ar¹-59)
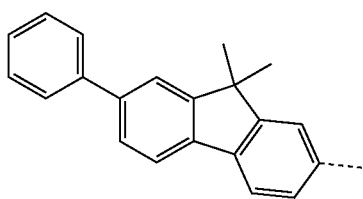 (Ar¹-60)
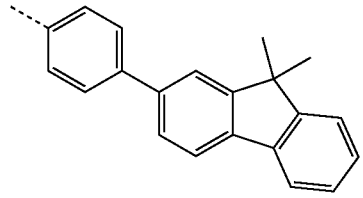 (Ar¹-61)
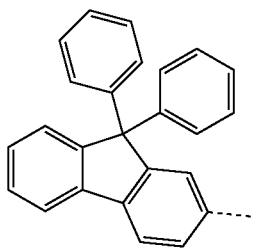 (Ar¹-62)

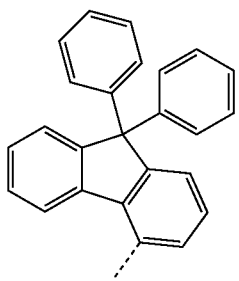 (Ar¹-63)
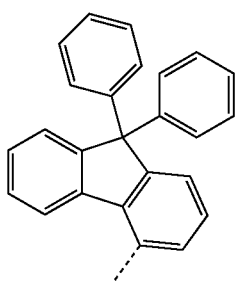 (Ar¹-64)
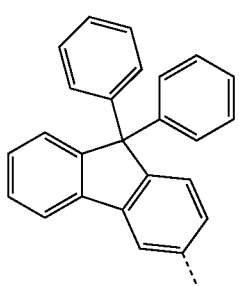 (Ar¹-65)
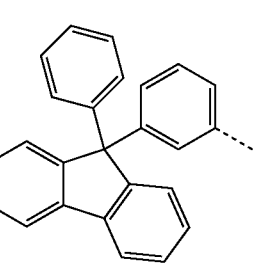 (Ar¹-66)
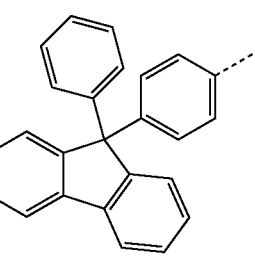 (Ar¹-67)
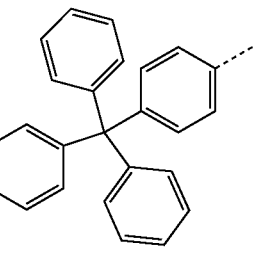 (Ar¹-68)
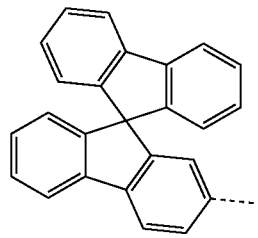 (Ar¹-69)
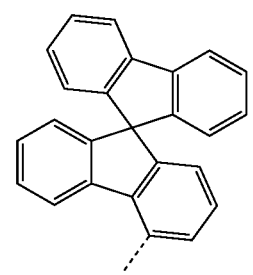 (Ar¹-70)
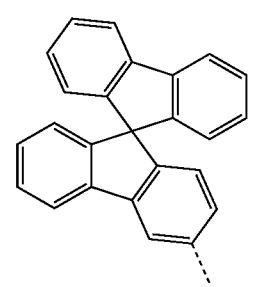 (Ar¹-71)
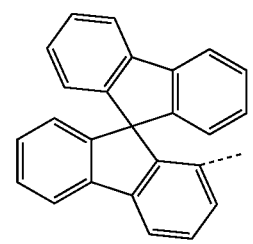 (Ar¹-72)
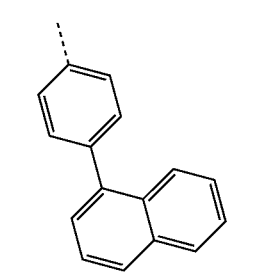 (Ar¹-73)

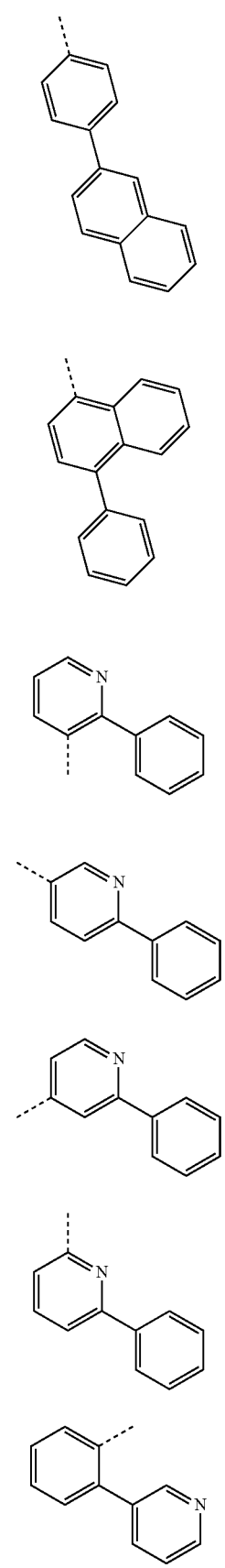
24. The material according to claim 21, wherein the group Ar¹ is selected from one of the formulae (Ar¹-1) to (Ar¹-88)

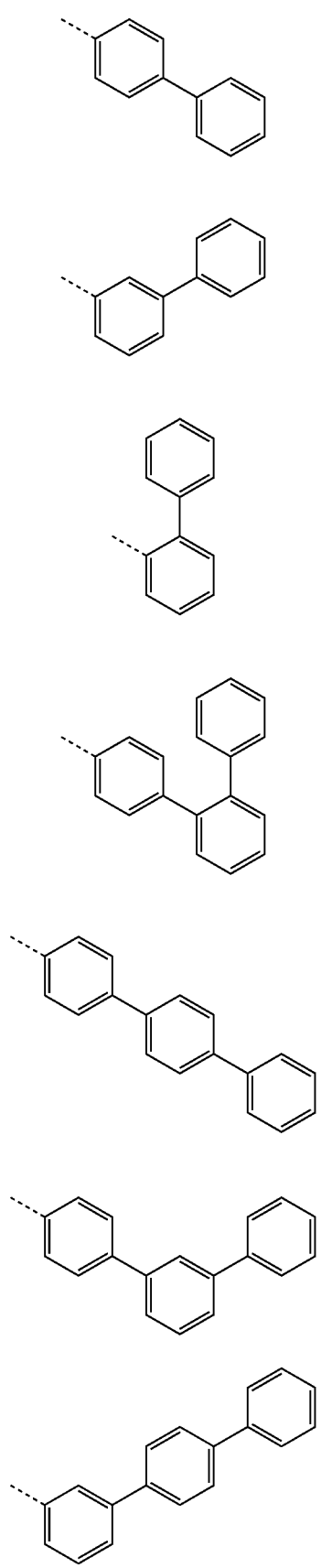

(Ar¹-13)
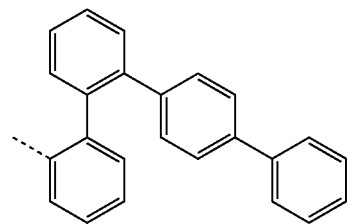
(Ar¹-14)
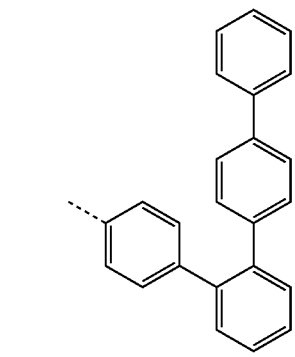
(Ar¹-15)
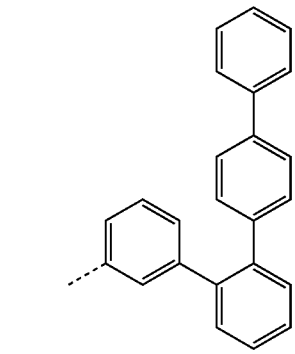
(Ar¹-16)
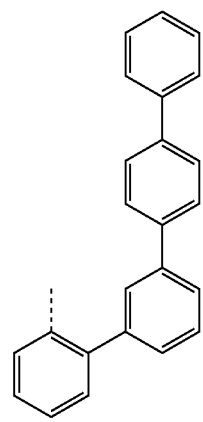
(Ar¹-17)
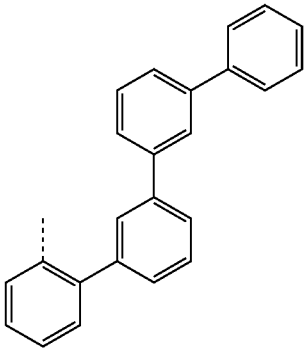
(Ar¹-18)
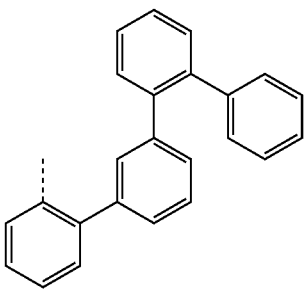
(Ar¹-19)
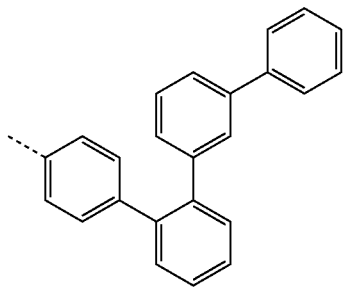
(Ar¹-20)
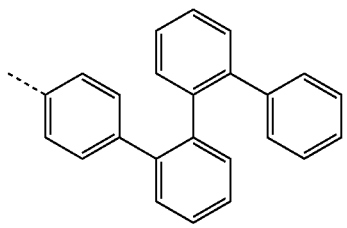
(Ar¹-21)
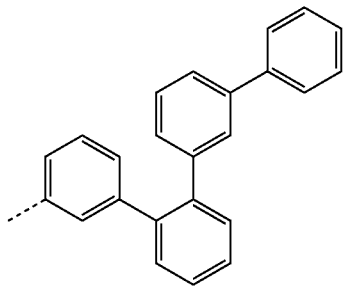

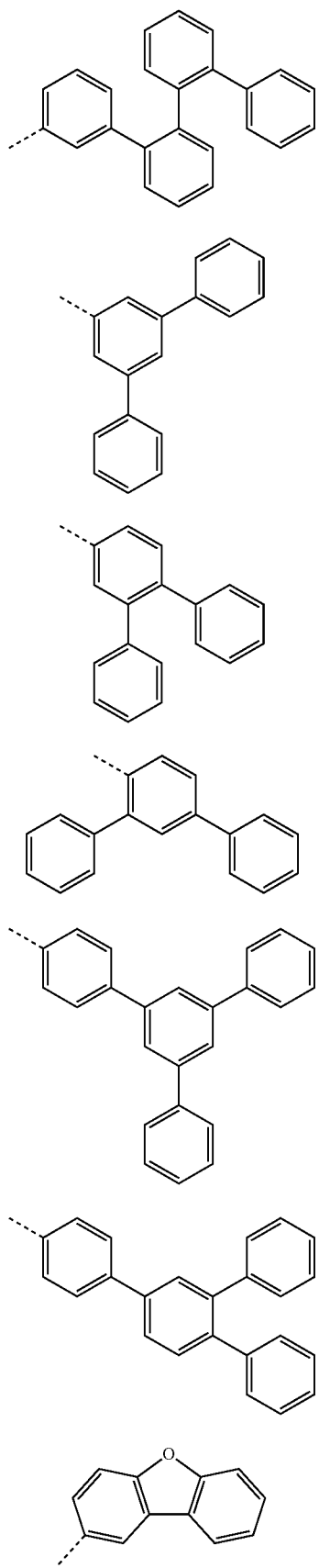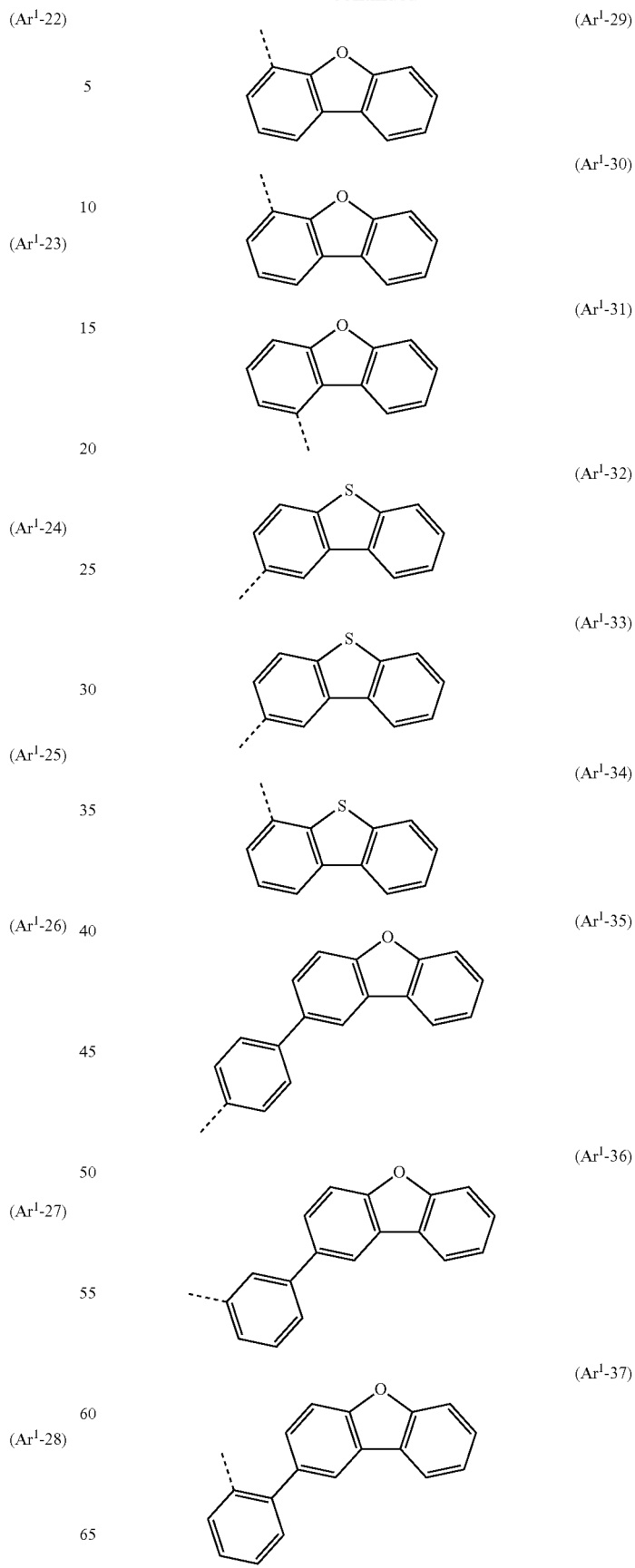

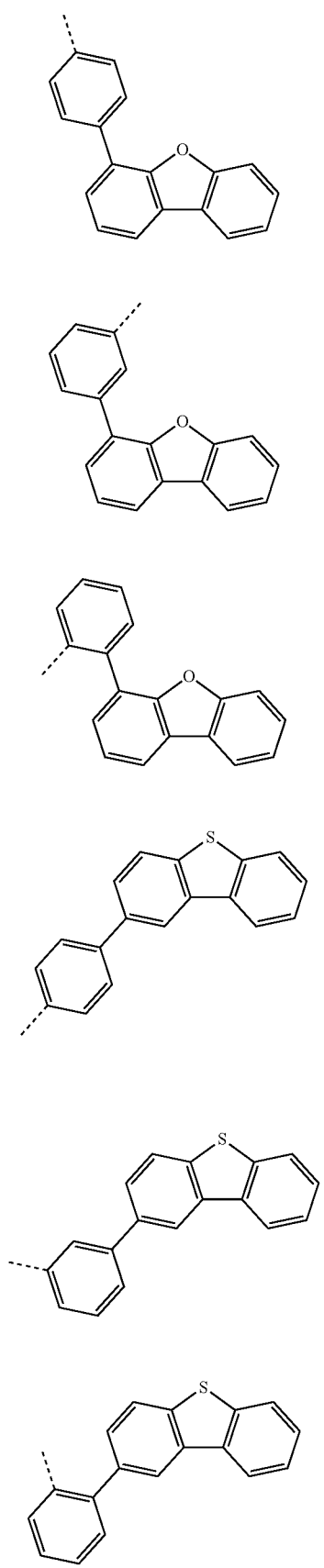
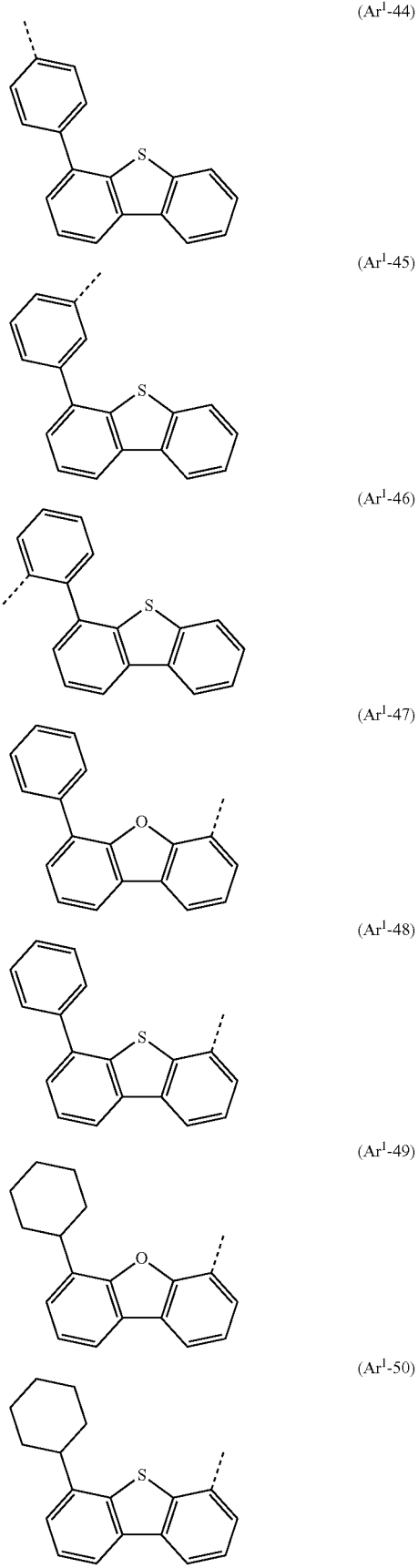

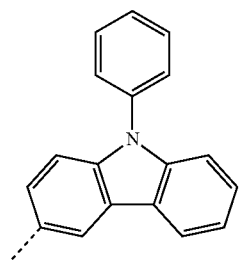 (Ar¹-51)
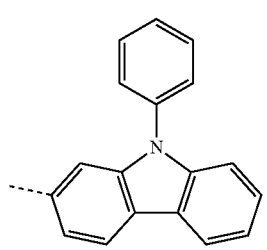 (Ar¹-52)
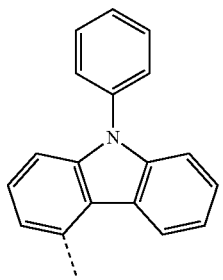 (Ar¹-53)
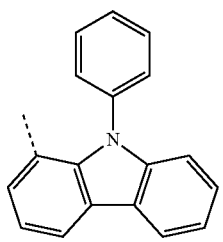 (Ar¹-54)
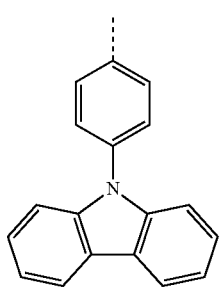 (Ar¹-55)
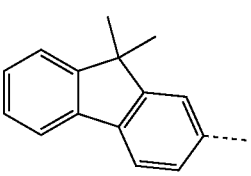 (Ar¹-56)
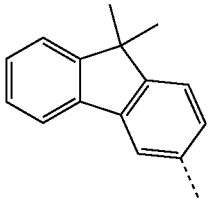 (Ar¹-57)
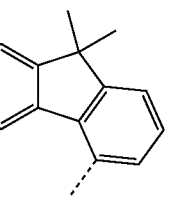 (Ar¹-58)
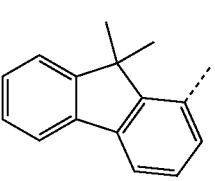 (Ar¹-59)
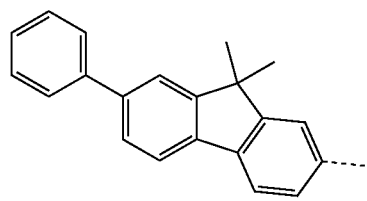 (Ar¹-60)
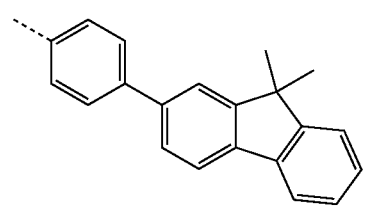 (Ar¹-61)
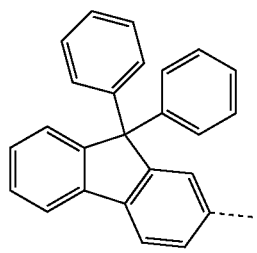 (Ar¹-62)
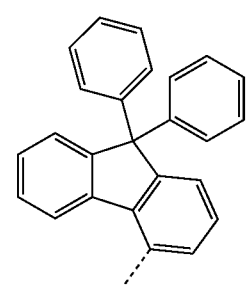 (Ar¹-63)

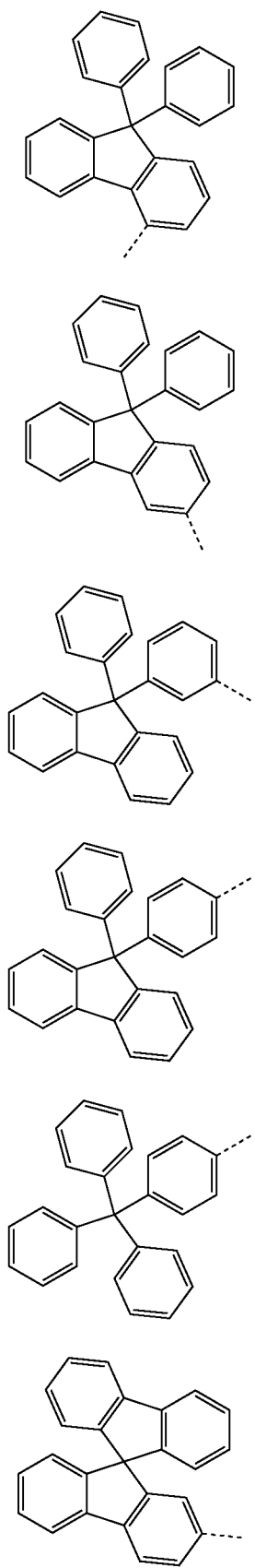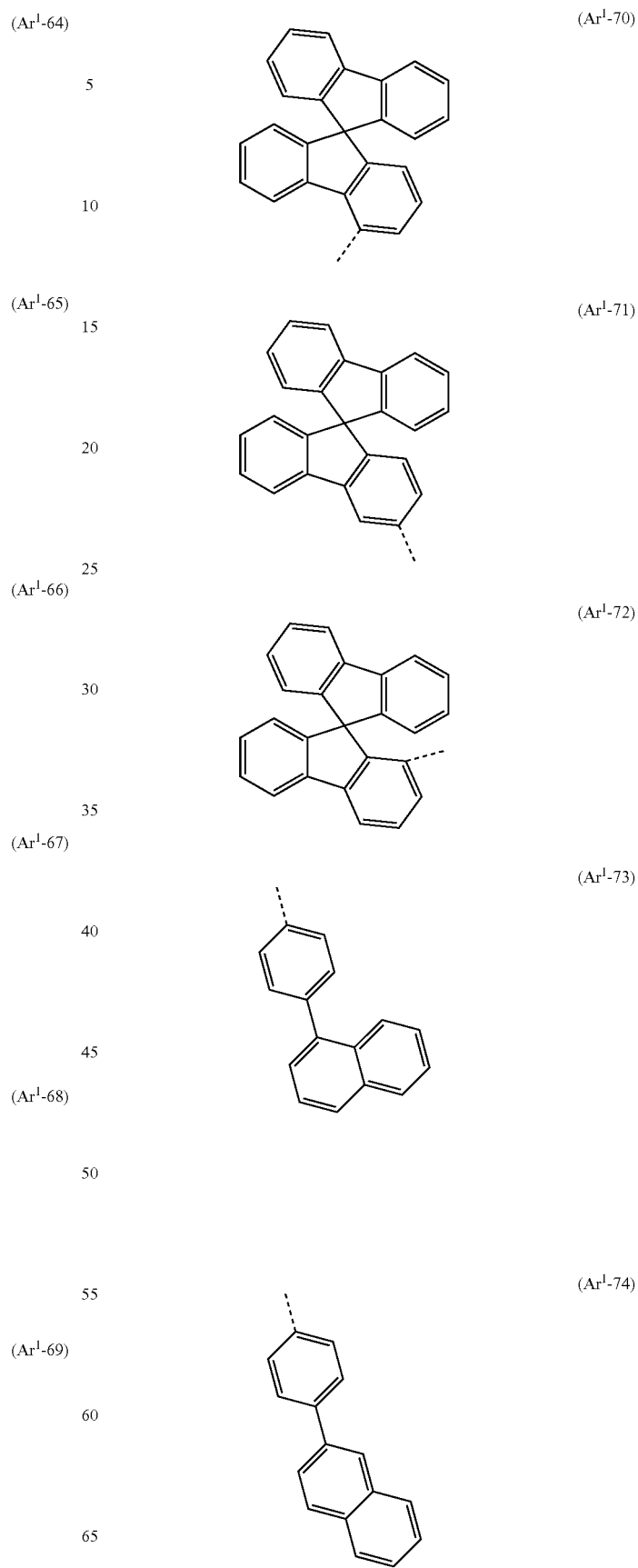

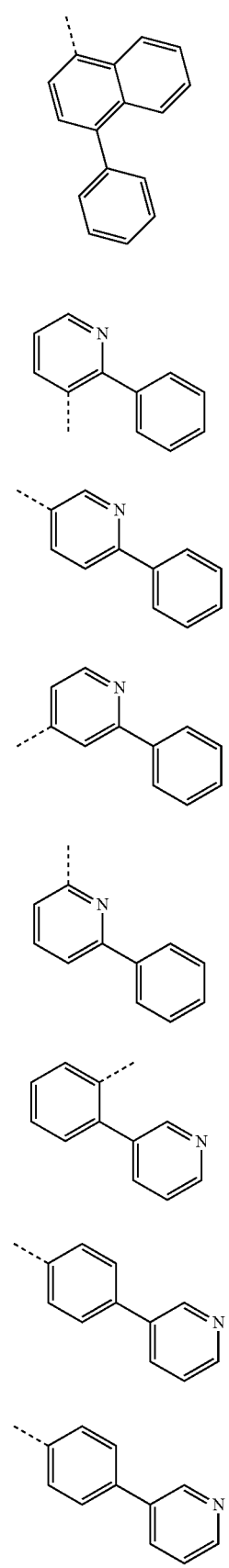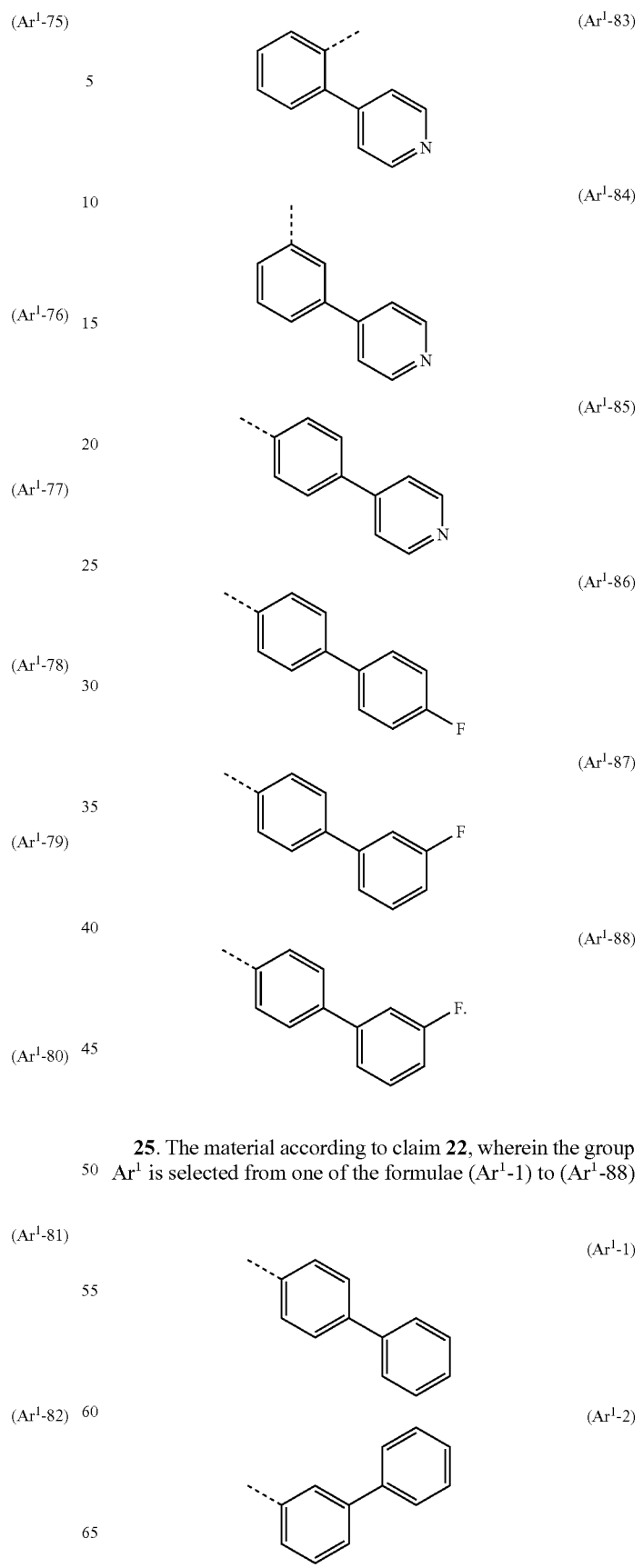
25. The material according to claim 22, wherein the group $Ar^1$ is selected from one of the formulae $(Ar^1-1)$ to $(Ar^1-88)$ -continued
(Ar¹-3)
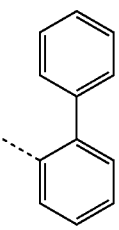
(Ar¹-4)
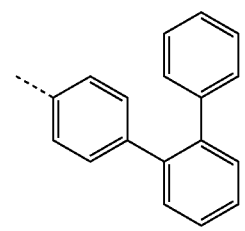
(Ar¹-5)
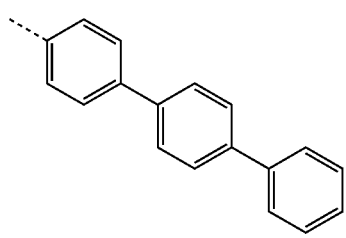
(Ar¹-6)
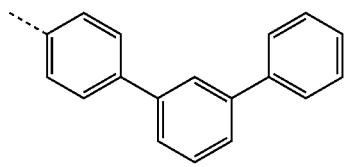
(Ar¹-7)
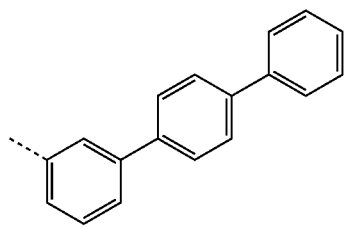
(Ar¹-8)
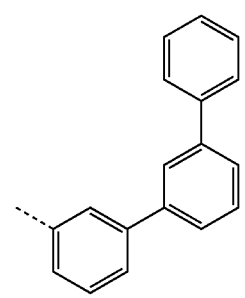
-continued
(Ar¹-9)
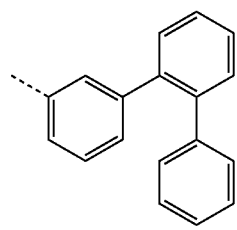
(Ar¹-10)
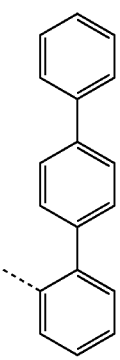
(Ar¹-11)
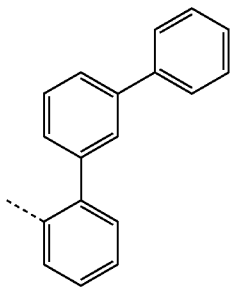
(Ar¹-12)
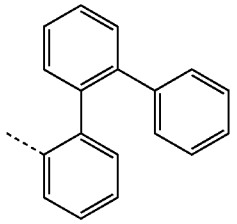
(Ar¹-13)
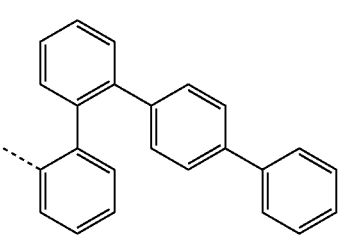

-continued
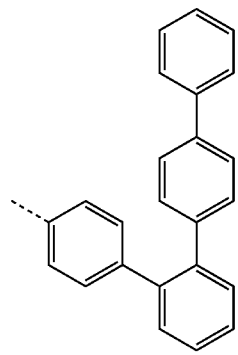
(Ar¹-14)
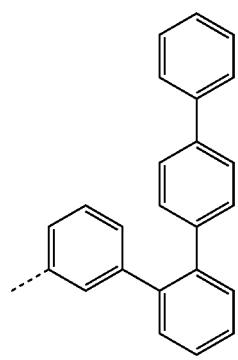
(Ar¹-15)
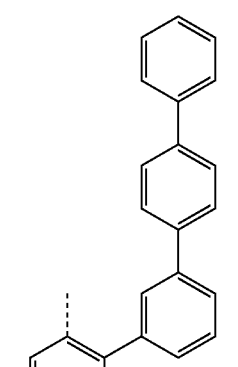
(Ar¹-16)
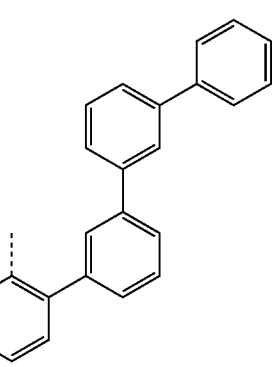
(Ar¹-17)
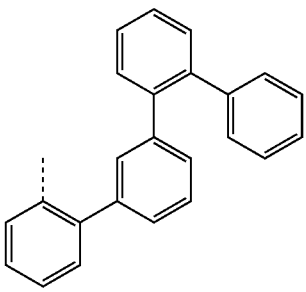
(Ar¹-18)
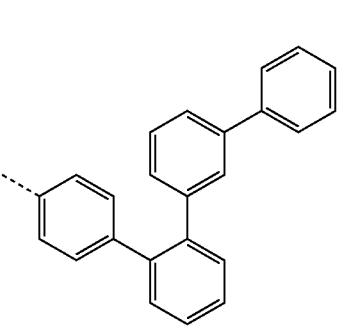
(Ar¹-19)
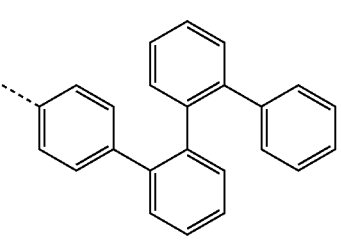
(Ar¹-20)
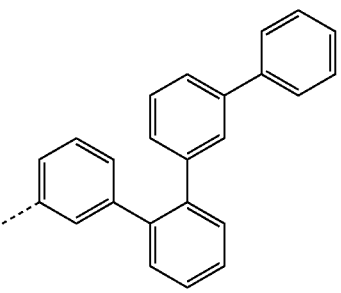
(Ar¹-21)
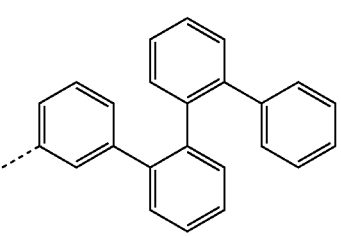
(Ar¹-22)

(Ar¹-23)
(Ar¹-24)
(Ar¹-25)
(Ar¹-26)
(Ar¹-27)
(Ar¹-28)
(Ar¹-29)
(Ar¹-30)
(Ar¹-31)
(Ar¹-32)
(Ar¹-33)
(Ar¹-34)
(Ar¹-35)
(Ar¹-36)
(Ar¹-37)

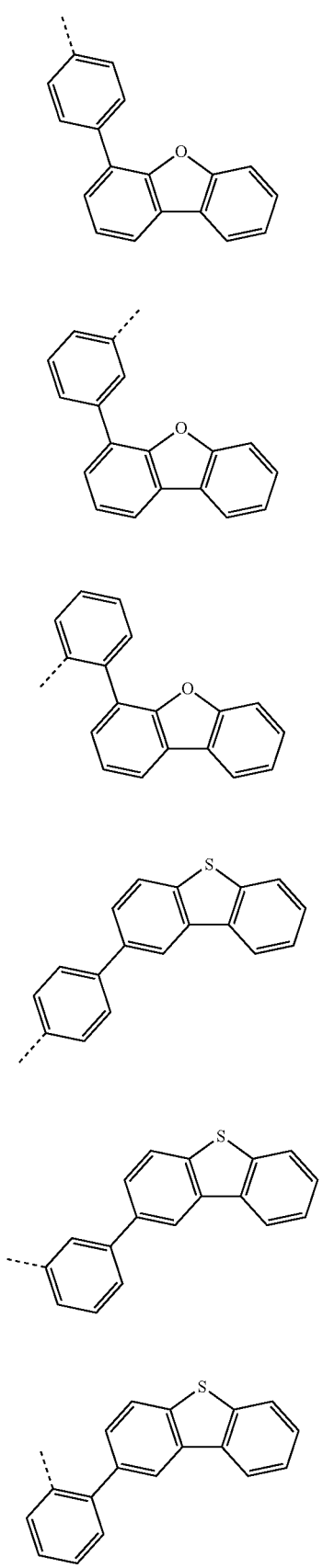
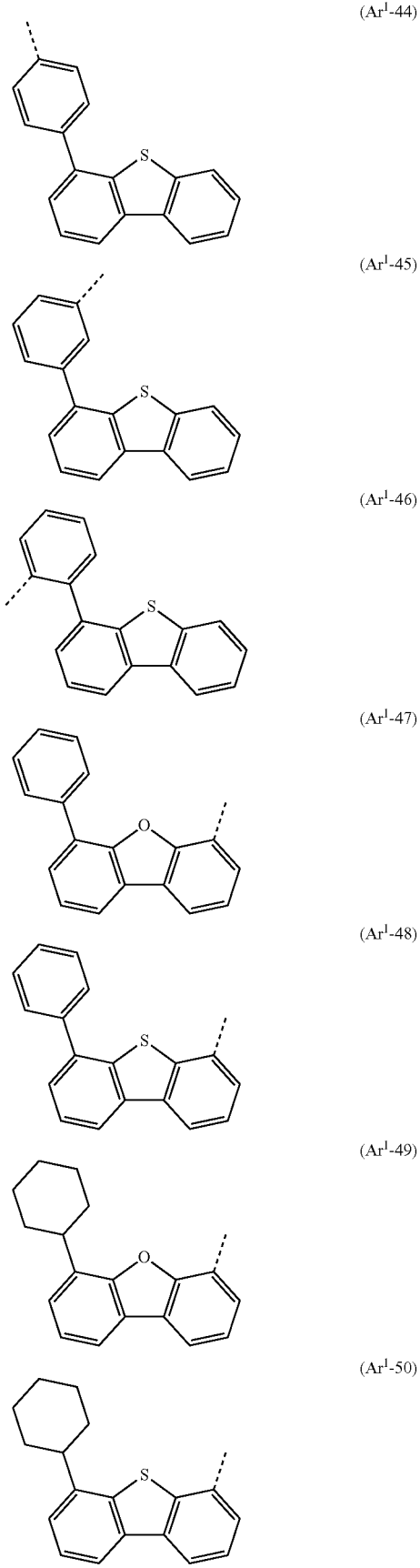

(Ar¹-51)
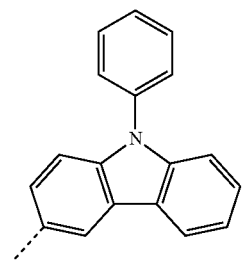
(Ar¹-52)
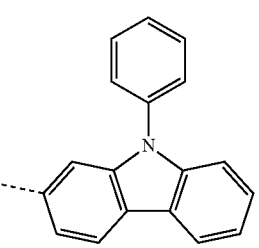
(Ar¹-53)
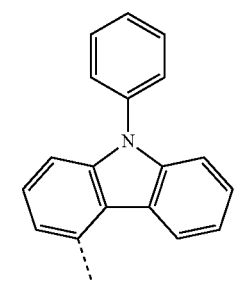
(Ar¹-54)
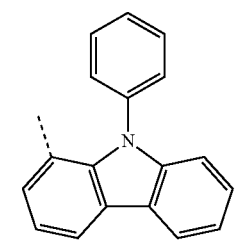
(Ar¹-55)
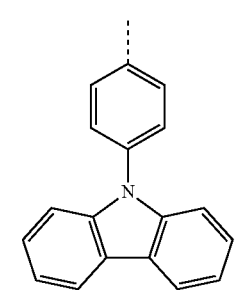
(Ar¹-56)
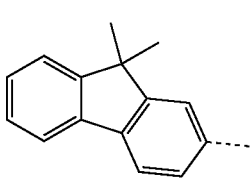
(Ar¹-57)
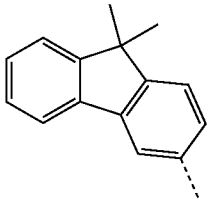
(Ar¹-58)
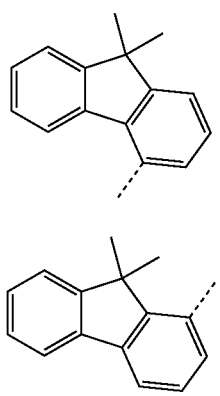
(Ar¹-59)
(Ar¹-60)
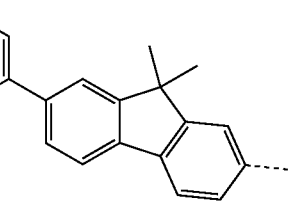
(Ar¹-61)
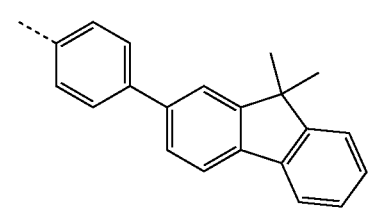
(Ar¹-62)
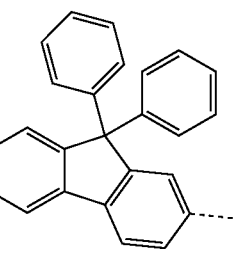
(Ar¹-63)
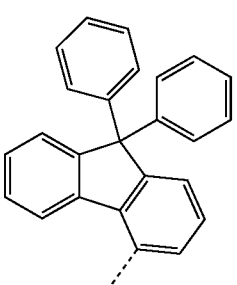

-continued
(Ar¹-64)
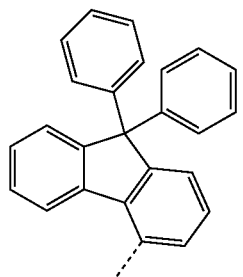
(Ar¹-65)
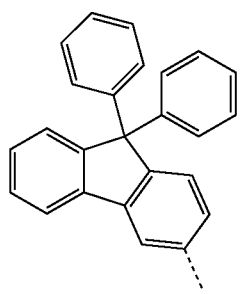
(Ar¹-66)
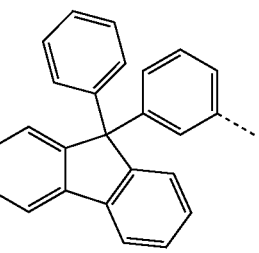
(Ar¹-67)
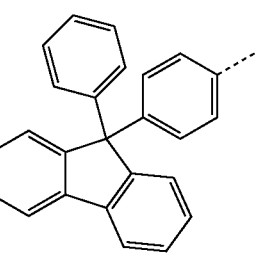
(Ar¹-68)
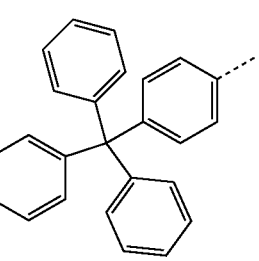
(Ar¹-69)
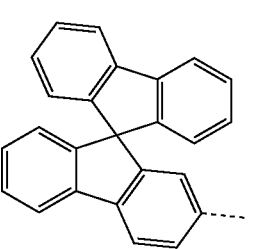
-continued
(Ar¹-70)
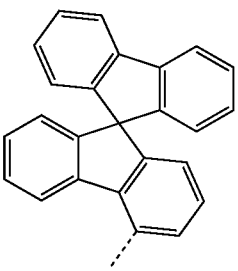
(Ar¹-71)
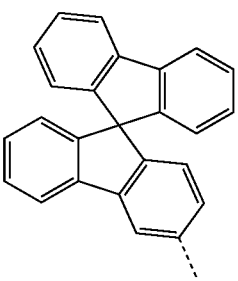
(Ar¹-72)
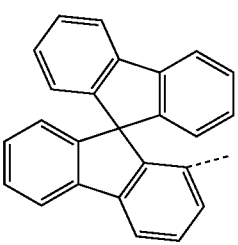
(Ar¹-73)
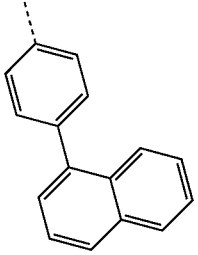
(Ar¹-74)
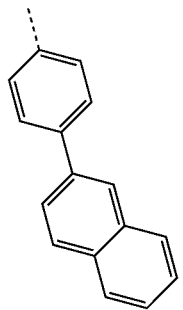

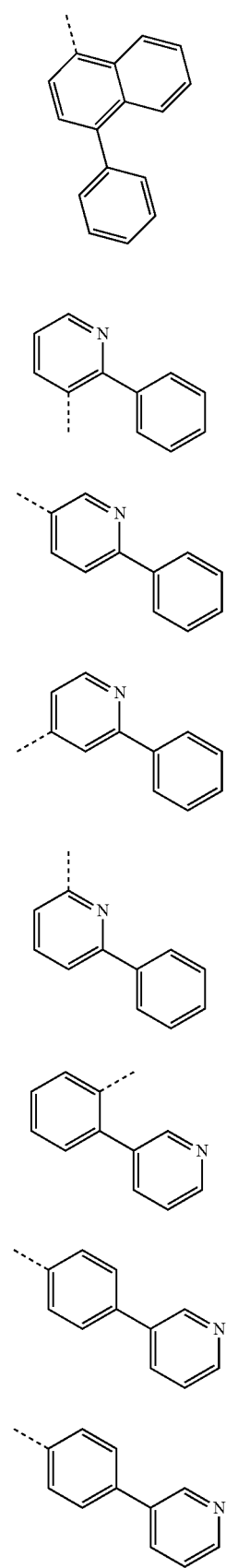
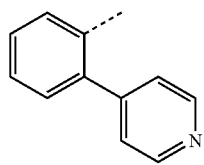
26. The material according to claim 1, wherein the group $Ar^2$ is selected from one of the formulae ($Ar^2$-1) to ($Ar^2$-26)

-continued
(Ar²-3)
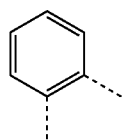
(Ar²-4)
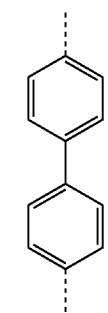
(Ar²-5)
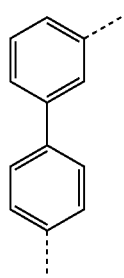
(Ar²-6)
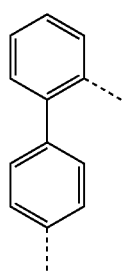
(Ar²-7)
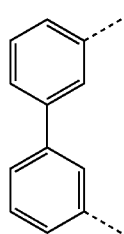
(Ar²-8)
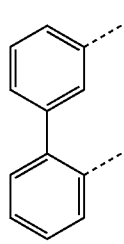
-continued
(Ar²-9)
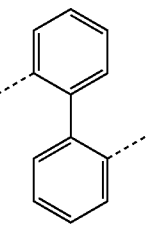
(Ar²-10)
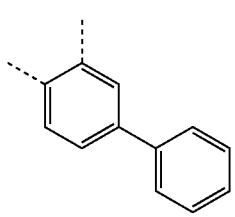
(Ar²-11)
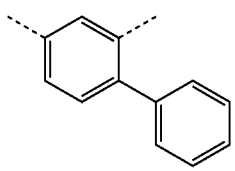
(Ar²-12)
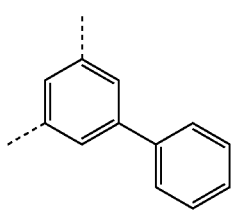
(Ar²-13)
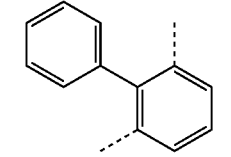
(Ar²-14)
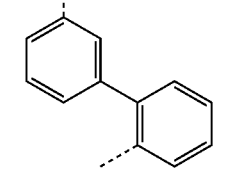
(Ar²-15)
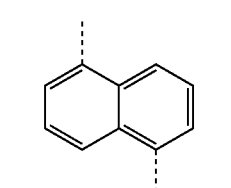
(Ar²-16)
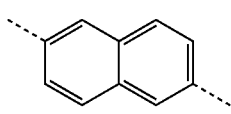

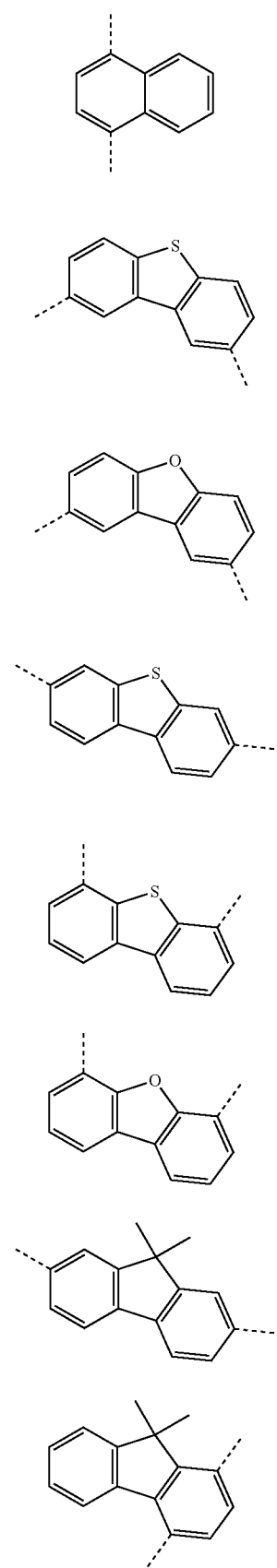
(Ar²-17)
(Ar²-18)
(Ar²-19)
(Ar²-20)
(Ar²-21)
(Ar²-22)
(Ar²-23)
(Ar²-24)
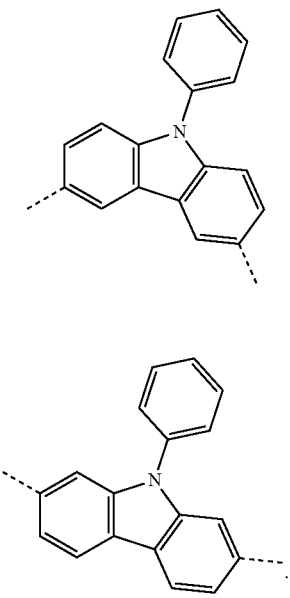
(Ar²-25)
(Ar²-26)
27. The material according to claim 21, wherein the group Ar² is selected from one of the formulae (Ar²-1) to (Ar²-26)
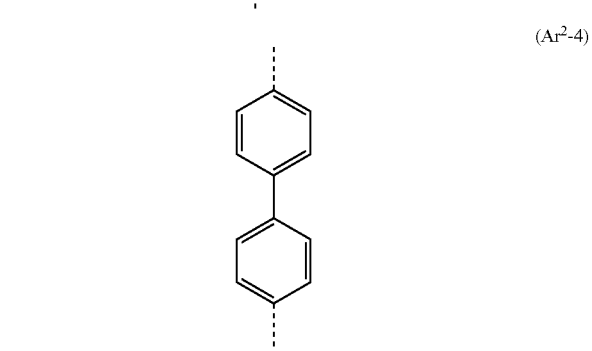
(Ar²-1)
(Ar²-2)
(Ar²-3)
(Ar²-4)

-continued
(Ar²-5) 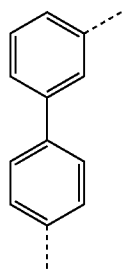
(Ar²-6) 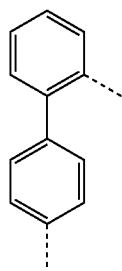
(Ar²-7) 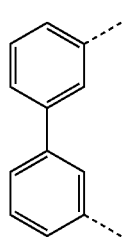
(Ar²-8) 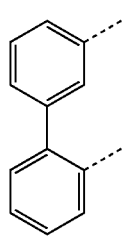
(Ar²-9) 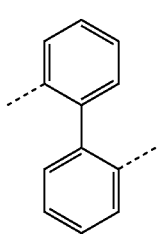
(Ar²-10) 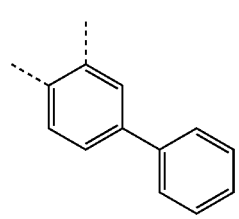
-continued
(Ar²-11) 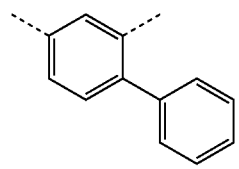
(Ar²-12) 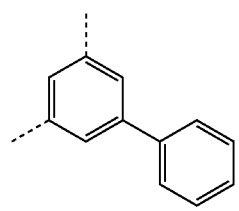
(Ar²-13) 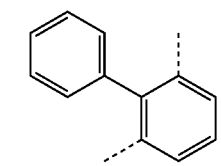
(Ar²-14) 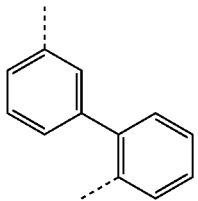
(Ar²-15) 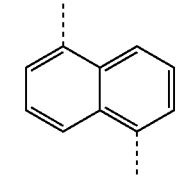
(Ar²-16) 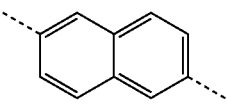
(Ar²-17) 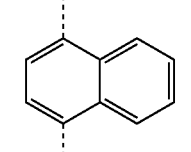
(Ar²-18) 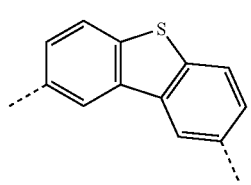

221
-continued
(Ar²-19)
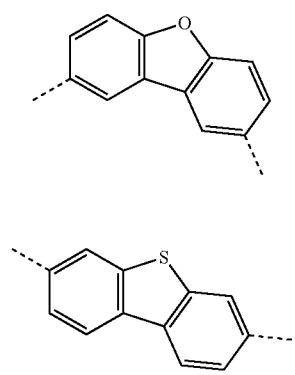
(Ar²-20)
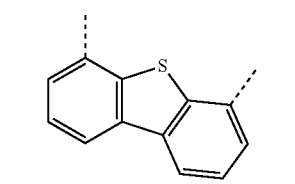
(Ar²-21)
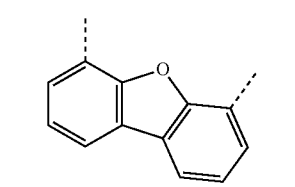
(Ar²-22)
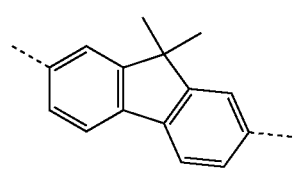
(Ar²-23)
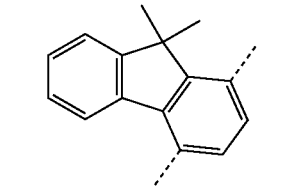
(Ar²-24)
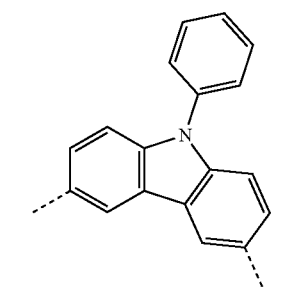
(Ar²-25)
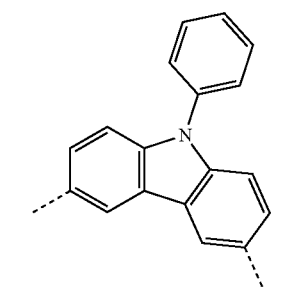
222
-continued
(Ar²-26)
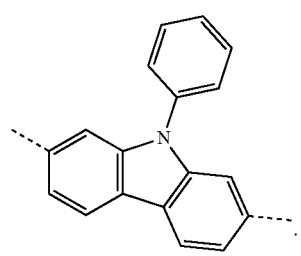
28. The material according to claim 22, wherein the group Ar² is selected from one of the formulae (Ar²-1) to (Ar²-26)
(Ar²-1)
(Ar²-2)
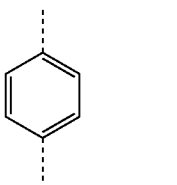
(Ar²-3)
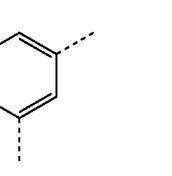
(Ar²-4)
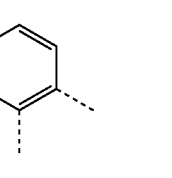
(Ar²-5)
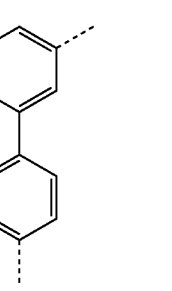

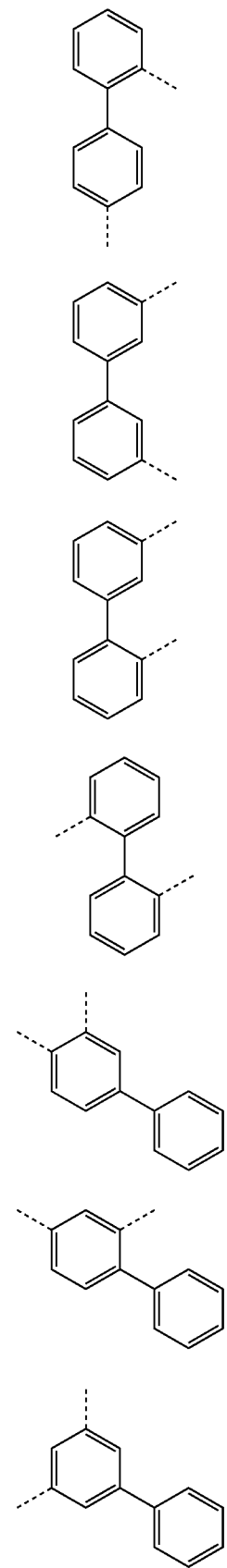
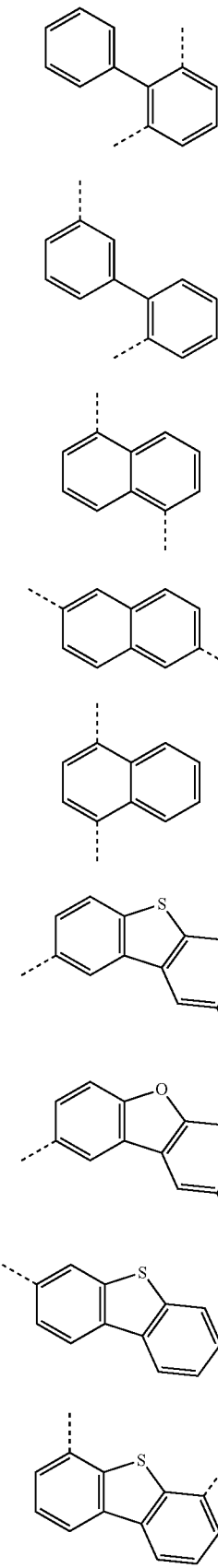

-continued
(Ar²-22)
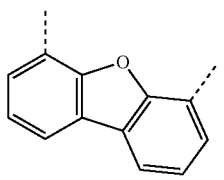
(Ar²-23)
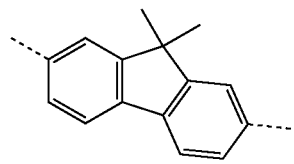
(Ar²-24)
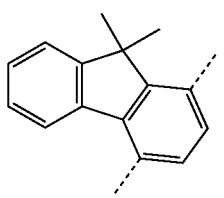
-continued
(Ar²-25)
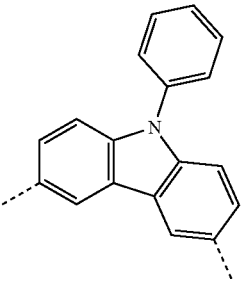
(Ar²-26)
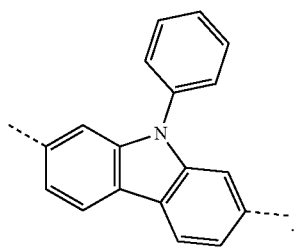
* * * * *